US012653980B2

(12) United States Patent　　(10) Patent No.: US 12,653,980 B2
Valiyambath et al.　　(45) Date of Patent:　Jun. 16, 2026

(54) INFLATABLE HEADGEAR AND PATIENT INTERFACE

(71) Applicant: ResMed Asia Pte. Ltd., Singapore (SG)

(72) Inventors: Mohankumar Krishnan Valiyambath, Singapore (SG); Adrian Jeffrey Lowry, Singapore (SG); Bangzheng Tan, Singapore (SG); Thontira Supaopasphun, Singapore (SG); Angelene Marie Ozolins, Bella Vista (AU); Jing Chen, Singapore (SG); R. Nithya, Singapore (SG); Maximilian Aji Wijoyoseno, Singapore (SG)

(73) Assignee: ResMed Asia Pte. Ltd., Singapore (SG)

( * ) Notice: Subject to any disclaimer, the term of this patent is extended or adjusted under 35 U.S.C. 154(b) by 755 days.

(21) Appl. No.: 18/013,862

(22) PCT Filed: Jun. 30, 2021

(86) PCT No.: PCT/SG2021/050382
　§ 371 (c)(1),
　(2) Date: Dec. 29, 2022

(87) PCT Pub. No.: WO2022/005402
　PCT Pub. Date: Jan. 6, 2022

(65) Prior Publication Data
　US 2023/0149648 A1　May 18, 2023

(30) Foreign Application Priority Data

Jun. 30, 2020　(SG) ............................ 10202006317V
　Nov. 6, 2020　(SG) ............................ 10202011064U

(51) Int. Cl.
　A61M 16/06　　(2006.01)

(52) U.S. Cl.
　CPC ..... *A61M 16/0683* (2013.01); *A61M 16/0616* (2014.02); *A61M 2205/0216* (2013.01)

(58) Field of Classification Search
　CPC .......... A61M 16/0488; A61M 16/0683; A61M 2205/0216; A62B 18/084; B63C 2011/128
　See application file for complete search history.

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| CN | 206080615 U | 4/2017 |
| CN | 206760821 U | 12/2017 |

(Continued)

OTHER PUBLICATIONS

Notice of Reasons for Refusal with English Translation issued in corresponding Japanese Application No. 2022-580987, eight pages, dated Apr. 15, 2025.

(Continued)

*Primary Examiner* — Joseph D. Boecker
(74) *Attorney, Agent, or Firm* — Nixon & Vanderhye P.C.

(57) ABSTRACT

The present technology relates to one or more of the screening, diagnosis, monitoring, treatment, prevention and amelioration of respiratory-related disorders. The present technology also relates to medical devices or apparatus, and their use. In particular, the present technology a headgear for supplying pressurised air to a patient, comprising a headgear tubing which is inflatable from a collapsed state to an inflated state to form a conduit for supplying pressurised air to the patient, and when the headgear tubing is in the collapsed state, the headgear tubing is elastically deformable (Continued)

and foldable on itself. The headgear may further comprise a rigidiser.

27 Claims, 45 Drawing Sheets

(56) References Cited

U.S. PATENT DOCUMENTS

| | | | |
|---|---|---|---|
| 5,687,715 | A | 11/1997 | Landis |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 2009/0044808 | A1 | 2/2009 | Guney et al. |
| 2009/0050156 | A1 | 2/2009 | Ng et al. |
| 2009/0223518 | A1* | 9/2009 | Kwok .................... A61M 16/06 128/205.25 |
| 2010/0000534 | A1 | 1/2010 | Kooij et al. |
| 2012/0325219 | A1* | 12/2012 | Smith ............... A61M 16/0875 128/205.25 |
| 2014/0102456 | A1* | 4/2014 | Ovizinsky ......... A61M 16/0066 128/205.25 |
| 2014/0158136 | A1* | 6/2014 | Romagnoli ....... A61M 16/0605 128/206.24 |
| 2014/0261440 | A1 | 9/2014 | Chodkowski |
| 2015/0128949 | A1* | 5/2015 | Jablonski .......... A61M 16/0875 128/205.25 |
| 2019/0091435 | A1* | 3/2019 | Steed .................. A61M 16/208 |
| 2019/0111227 | A1 | 4/2019 | Veliss et al. |
| 2019/0175861 | A1* | 6/2019 | Holyoake ............. A61M 16/16 |
| 2019/0282777 | A1 | 9/2019 | Kwok et al. |
| 2023/0381442 | A1* | 11/2023 | Khera ............... A61M 16/0683 |

FOREIGN PATENT DOCUMENTS

| | | | |
|---|---|---|---|
| CN | 207785470 | U | 8/2018 |
| CN | 208770113 | U | 4/2019 |
| JP | 2018-138231 | | 9/2018 |
| WO | WO 98/004310 | A1 | 2/1998 |
| WO | WO 98/034665 | A1 | 8/1998 |
| WO | WO 2000/078381 | A1 | 12/2000 |
| WO | WO 2004/073778 | A1 | 9/2004 |
| WO | WO 2005/063328 | A1 | 7/2005 |
| WO | WO 2005/099801 | A1 | 10/2005 |
| WO | WO 2006/074513 | A1 | 7/2006 |
| WO | WO 2006/130903 | A1 | 12/2006 |
| WO | WO 2008/011682 | A1 | 1/2008 |
| WO | WO 2008/011683 | A1 | 1/2008 |
| WO | WO 2008/070929 | A1 | 6/2008 |
| WO | WO 2009/052560 | A1 | 4/2009 |
| WO | WO 2010/135785 | A1 | 12/2010 |
| WO | WO 2012/167327 | A1 | 12/2012 |
| WO | WO 2012/171072 | A1 | 12/2012 |
| WO | WO 2013/020167 | A1 | 2/2013 |
| WO | WO-2020000033 | A1 * | 1/2020 ........ A61M 16/0683 |
| WO | WO 2020/037360 | A1 | 2/2020 |
| WO | WO 2020/157559 | A1 | 8/2020 |

OTHER PUBLICATIONS

First Office Action with English Translation issued in corresponding Chinese Application No. 202180052399.6, dated Jan. 14, 2025, 30 pages.

International Preliminary Report on Patentability in corresponding Application No. PCT/SG2021/050382, 10 pages, dated Jan. 12, 2023.

"*Respiratory Physiology*", by John B. West, Lippincott Williams & Wilkins, 9th edition published 2012 (8 pages).

International Search Report mailed Sep. 22, 2021 in corresponding PCT Application PT/SG2021/050382 (16 pages).

Written Opinion mailed Sep. 22, 2021 in corresponding PCT Application PCT/SG2021/050382 (8 pages).

Second Office Action issued in corresponding Chinese Application No. 202180052399.6, dated Jul. 16, 2025 (14 pages).

Notice of Reaasons for Refusal with English Translation issued in corresponding Japanese Application No. 2022-580987, dated Sep. 2, 2025 (6 pages).

* cited by examiner

Nasal cavity

Oral cavity

Larynx

Vocal folds

Oesophagus

Trachea

Bronchus

Lung

Heart

Diaphragm

Alveolar sacs

Nasal cavity

Nasal bone

Lateral nasal cartilage

Greater alar cartilage

Nostril

Lip superior

Lip inferior

Hard palate

Soft palate

Oropharynx

Tongue

Epiglottis

Vocal folds

Esophagus

Trachea

Larynx

Coronal plane

Frankfort horizontal

Nasolabial angle

Superior

Posterior

Anterior

Inferior

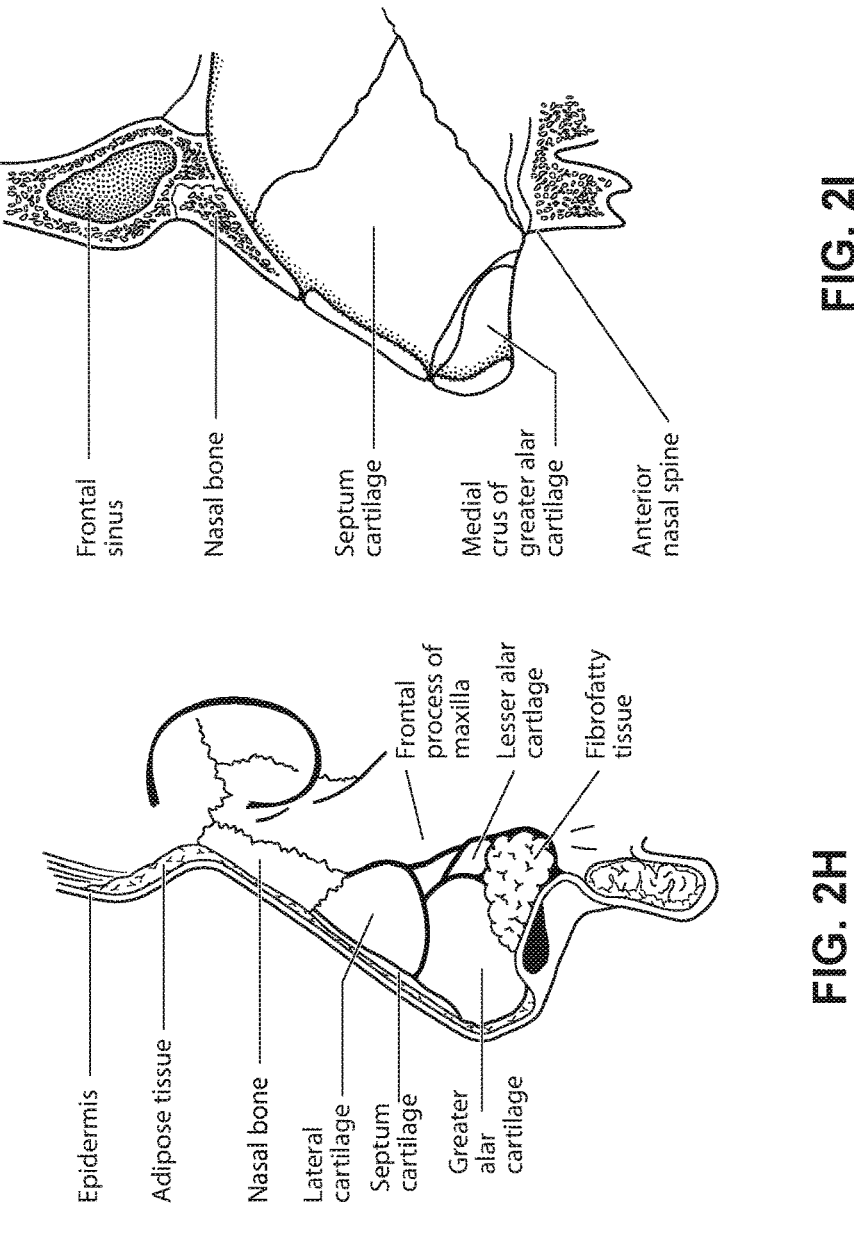
Frontal sinus
Nasal bone
Septum cartilage
Medial crus of greater alar cartilage
Anterior nasal spine
FIG. 2I
Frontal process of maxilla
Lesser alar cartilage
Fibrofatty tissue
Epidermis
Adipose tissue
Nasal bone
Lateral cartilage
Septum cartilage
Greater alar cartilage
FIG. 2H
FIG. 2G

Parietal bone

Temporal bone

Occipital bone

Trapezius m.

Frontal bone

Sphenoid bone

Nasal bone

Zygomatic bone

Maxilla

Masseter m.

Mandible

Mental protuberance

Digastricus m.

Sternocleidomastoid m.

Concha

Frontal bone

Supraorbital foramen

Nasal bones

Septal cartilage

Lateral cartilage

Sesamoid cartilage

Greater alar cartilage

Medial crus of greater alar cartilage

Anterior nasal spine

Infraorbital foramen

Lesser nasal cartilage

Alar fibrofatty tissue

Septal cartilage

Nose - Anterolateral view

3300

3000

3700

3200

3100

3400

3600

Figures 3B, 3C, 3D, 3E, 3F:
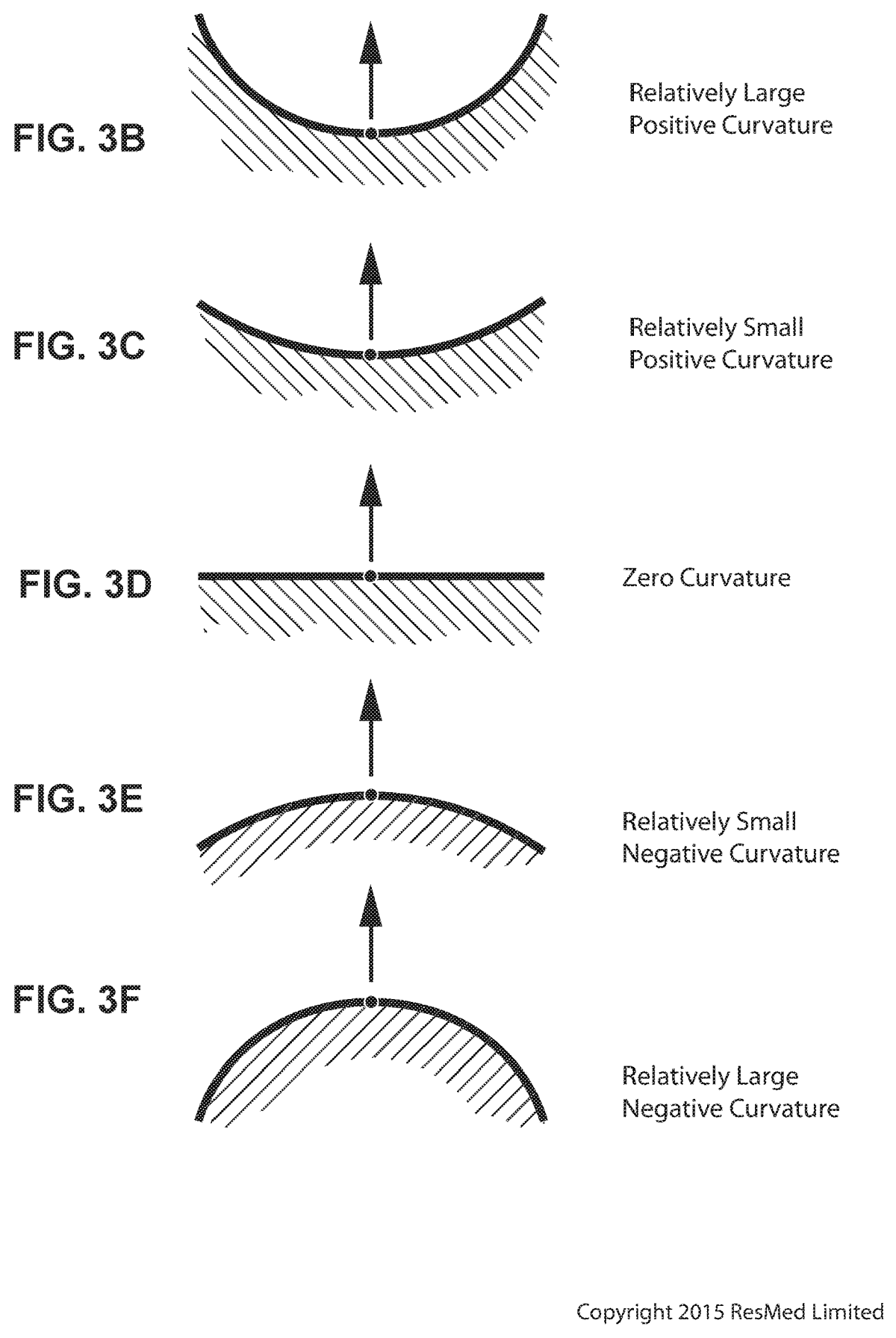

FIG. 3B — Relatively Large Positive Curvature

FIG. 3C — Relatively Small Positive Curvature

FIG. 3D — Zero Curvature

FIG. 3E — Relatively Small Negative Curvature

FIG. 3F — Relatively Large Negative Curvature

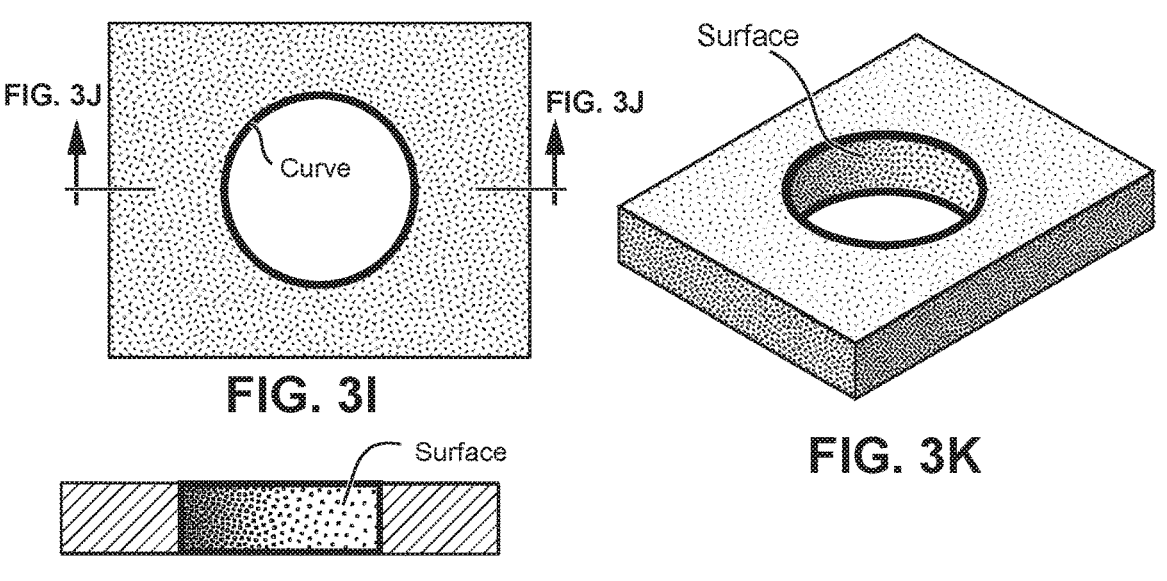
FIG. 3I
FIG. 3J
FIG. 3K
FIG. 3L
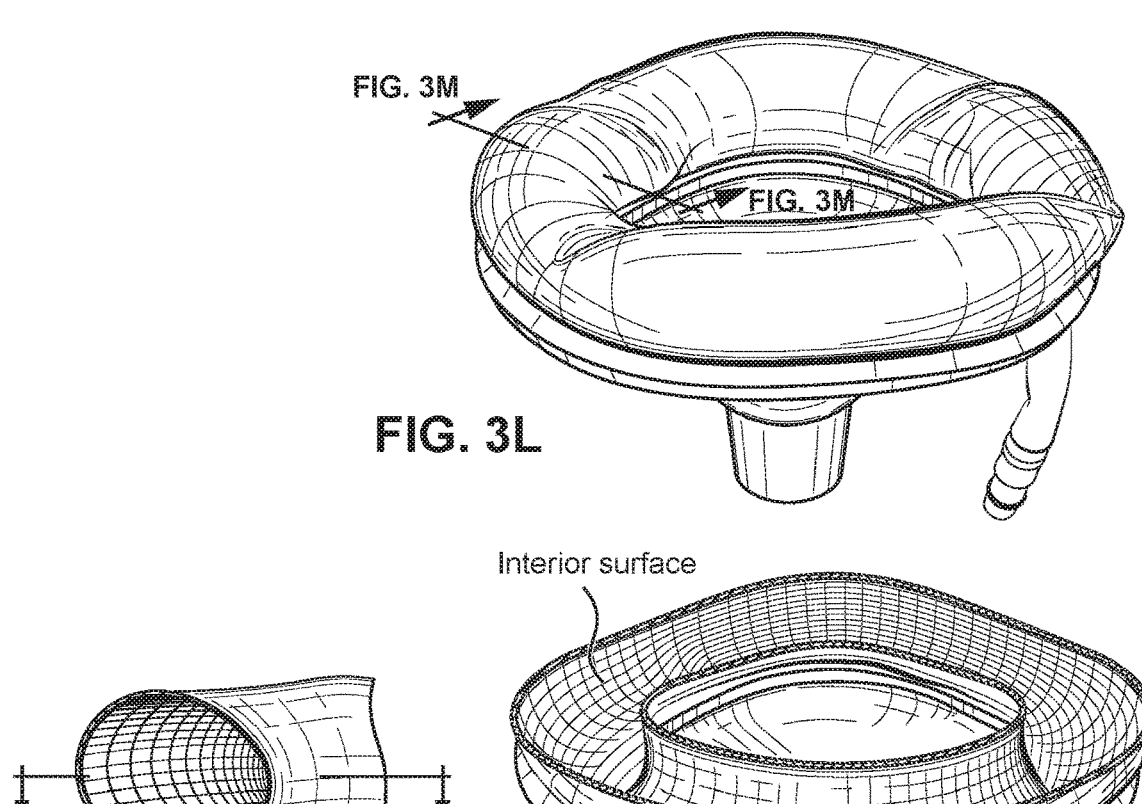
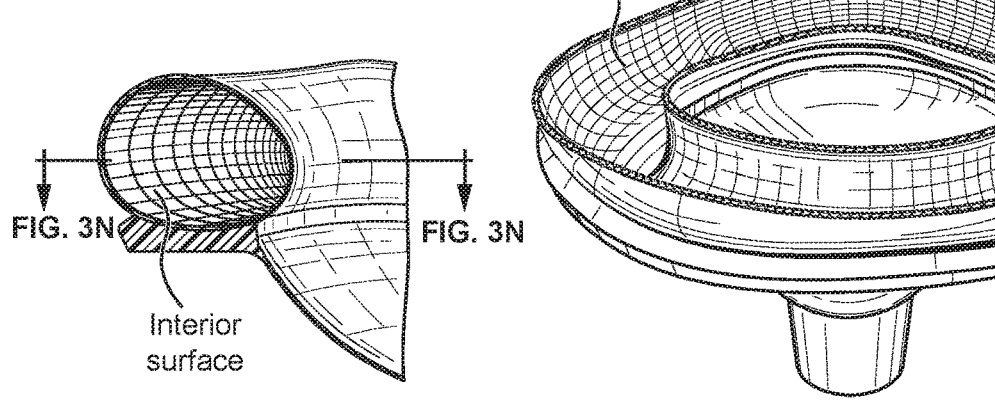
FIG. 3M      FIG. 3N Left-hand rule
Right-hand rule
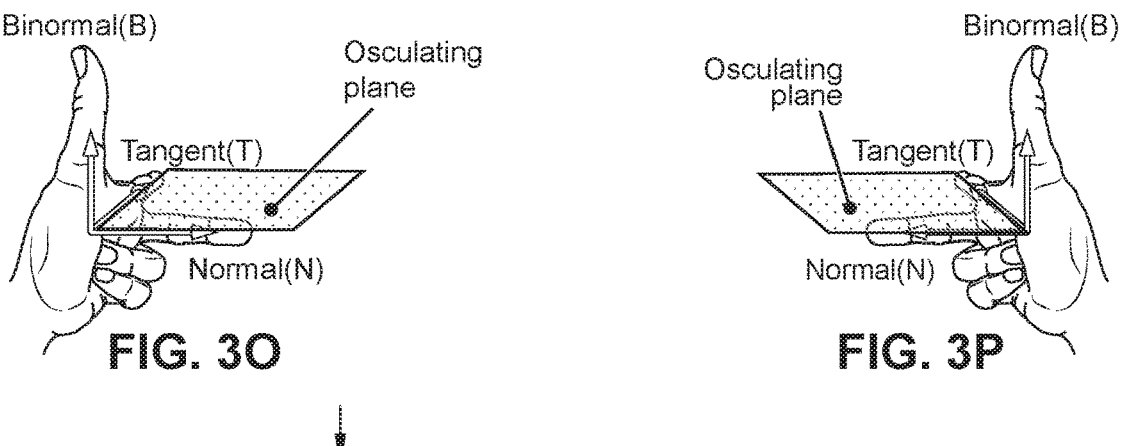
FIG. 3O
FIG. 3P
Left ear helix
Right ear helix
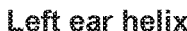
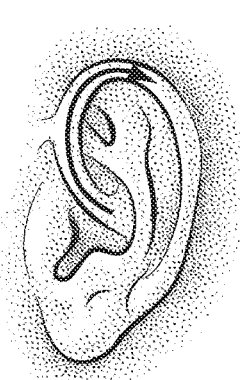
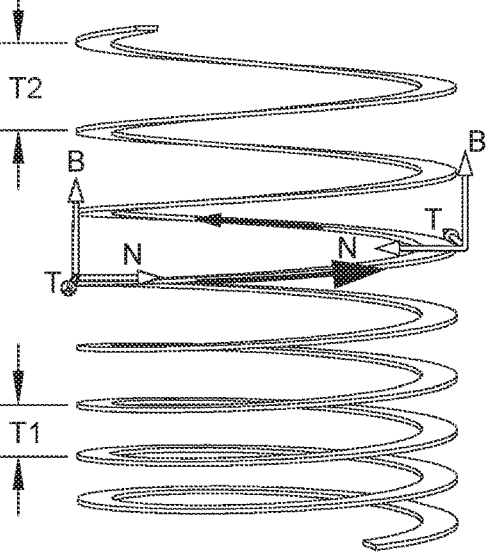
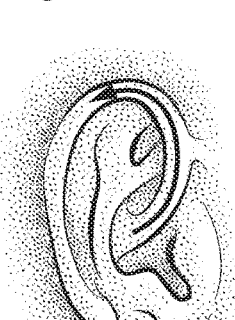
FIG. 3Q
Right-hand helix
Right-hand positive
FIG. 3R
FIG. 3S
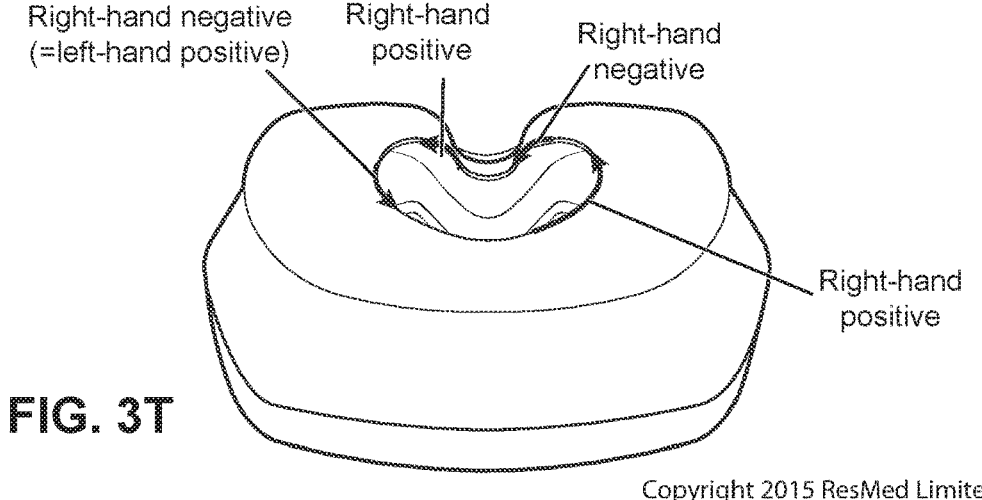
FIG. 3T

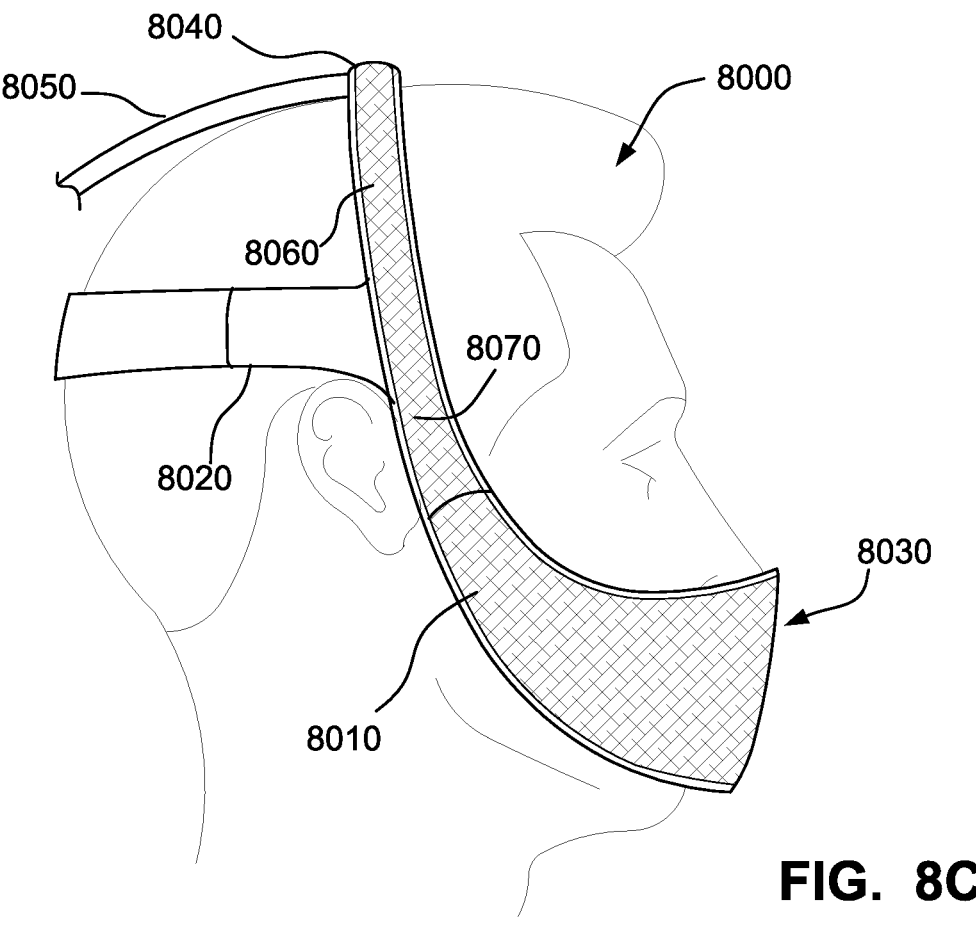
FIG. 8C
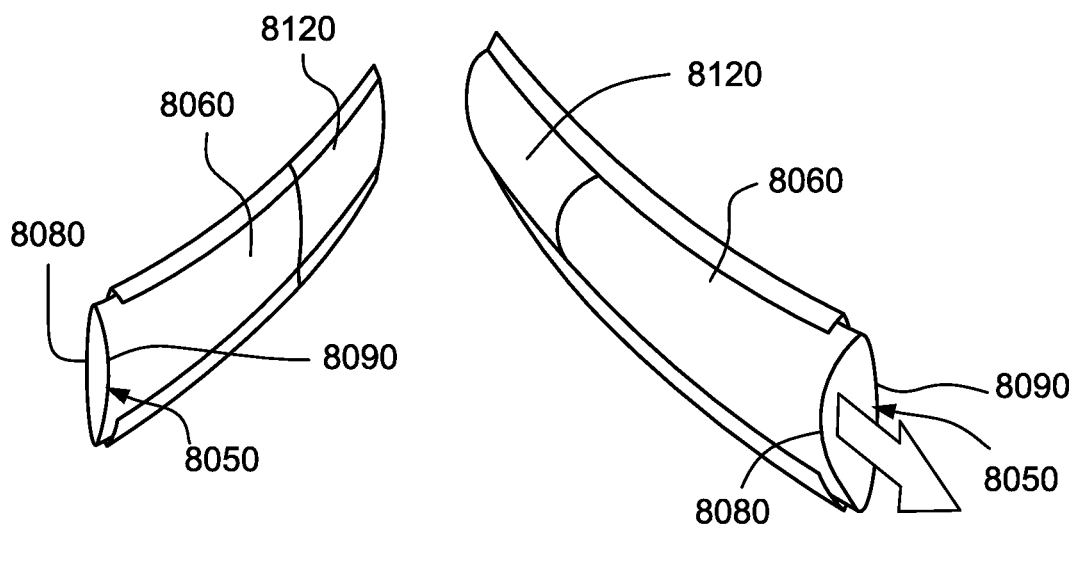
FIG. 8D          FIG. 8E

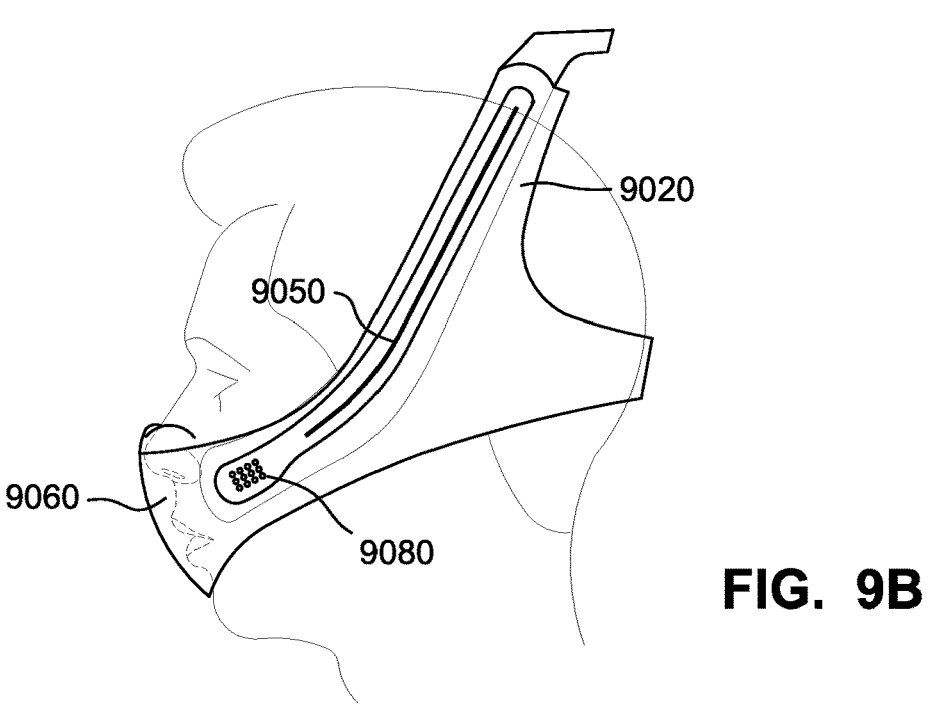
FIG. 9B
FIG. 9C
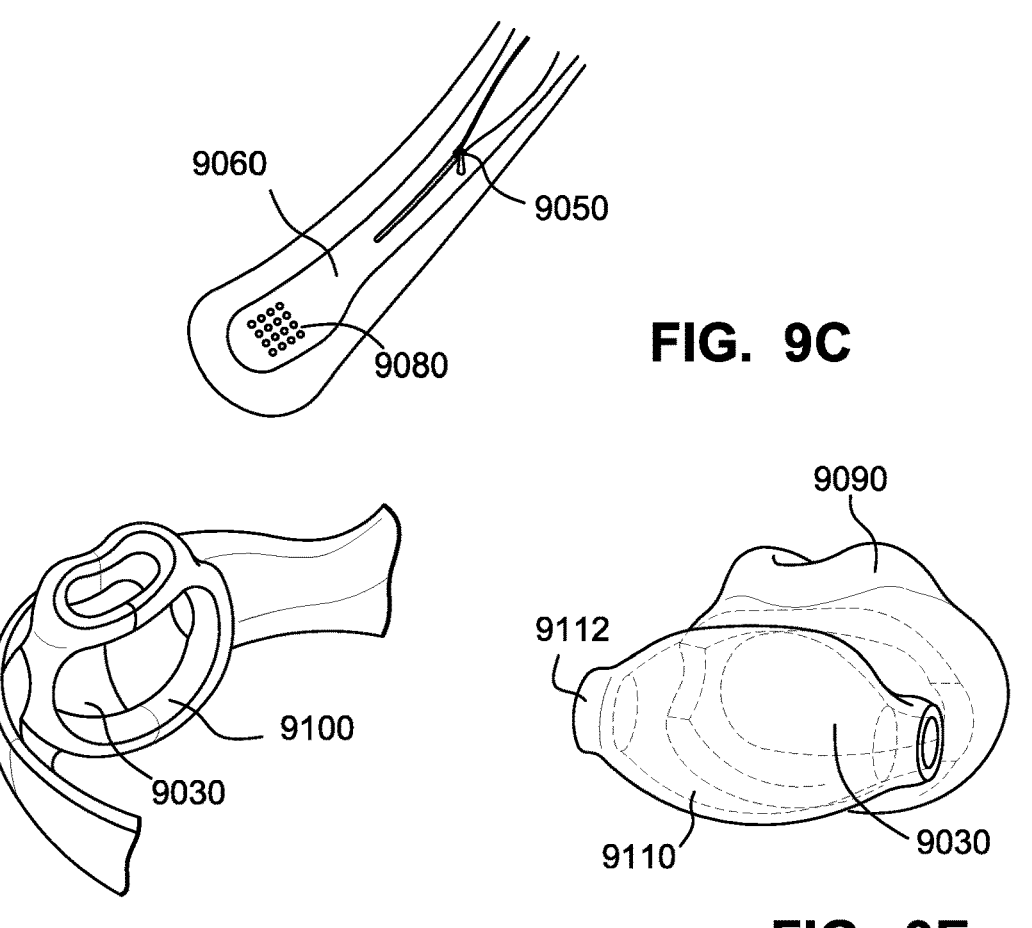
FIG. 9D
FIG. 9E

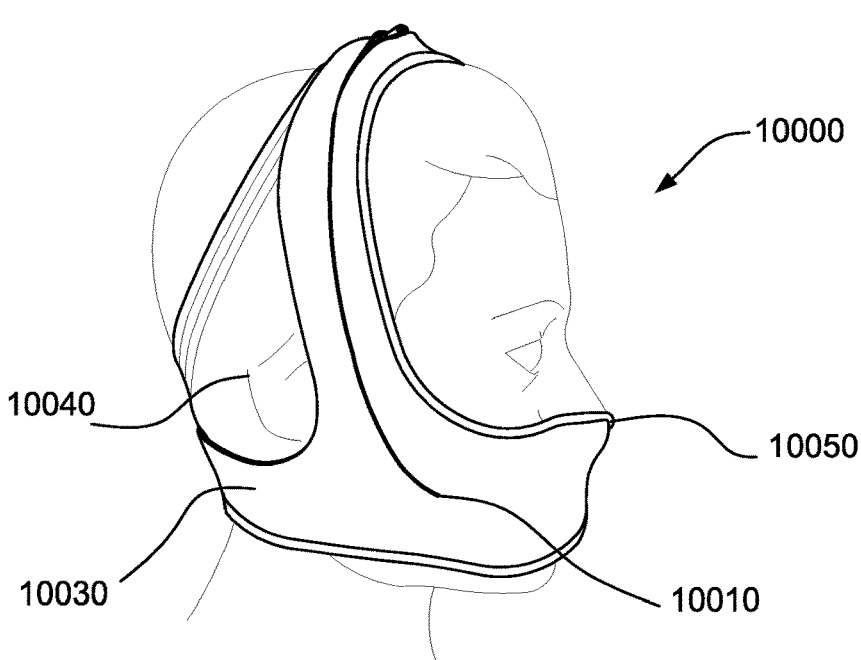
10000
10040
10050
10030
10010
FIG. 10A
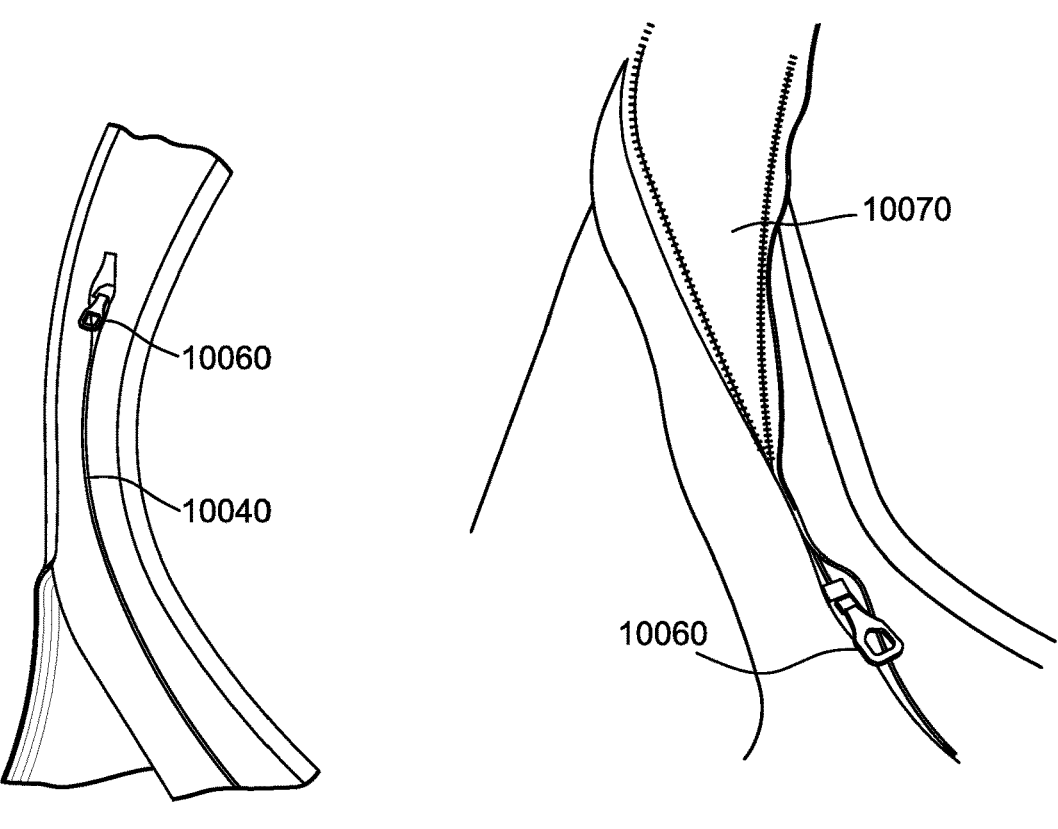
10060
10040
10070
10060
FIG. 10B          FIG. 10C

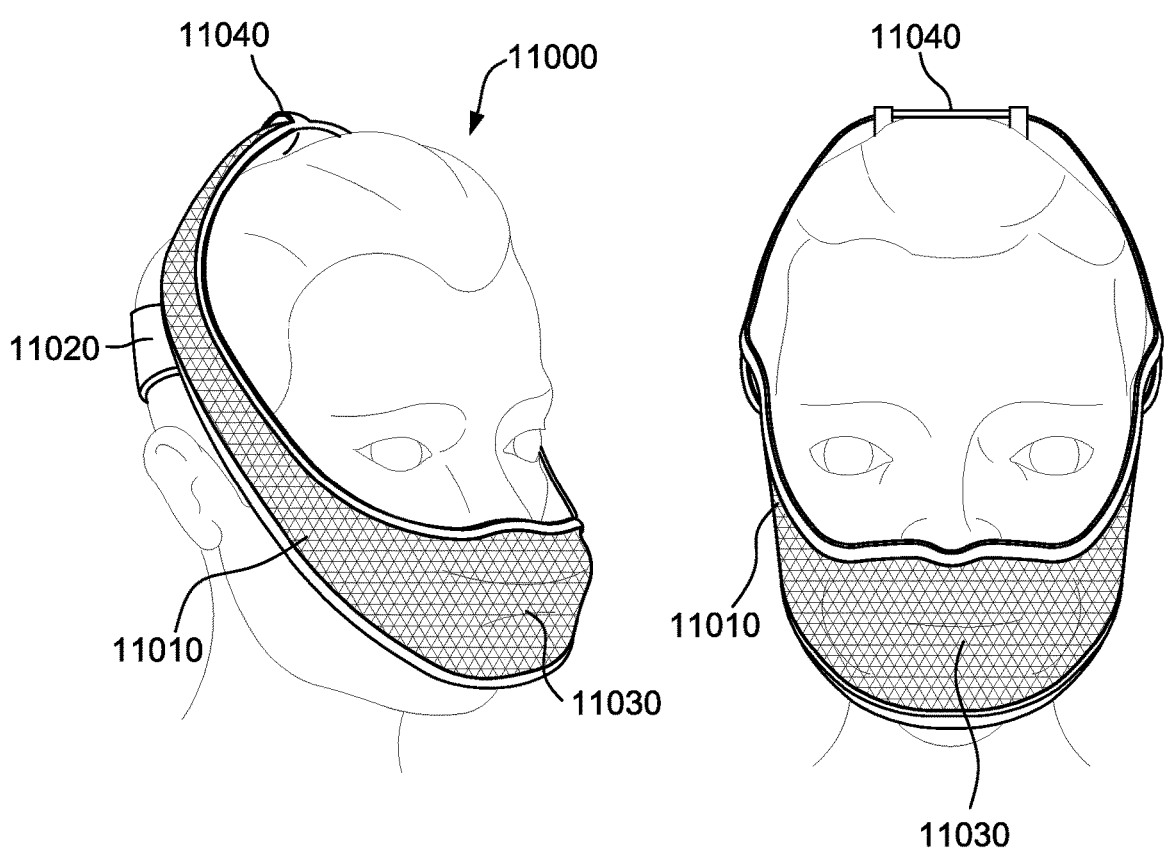
FIG. 11A
FIG. 11B
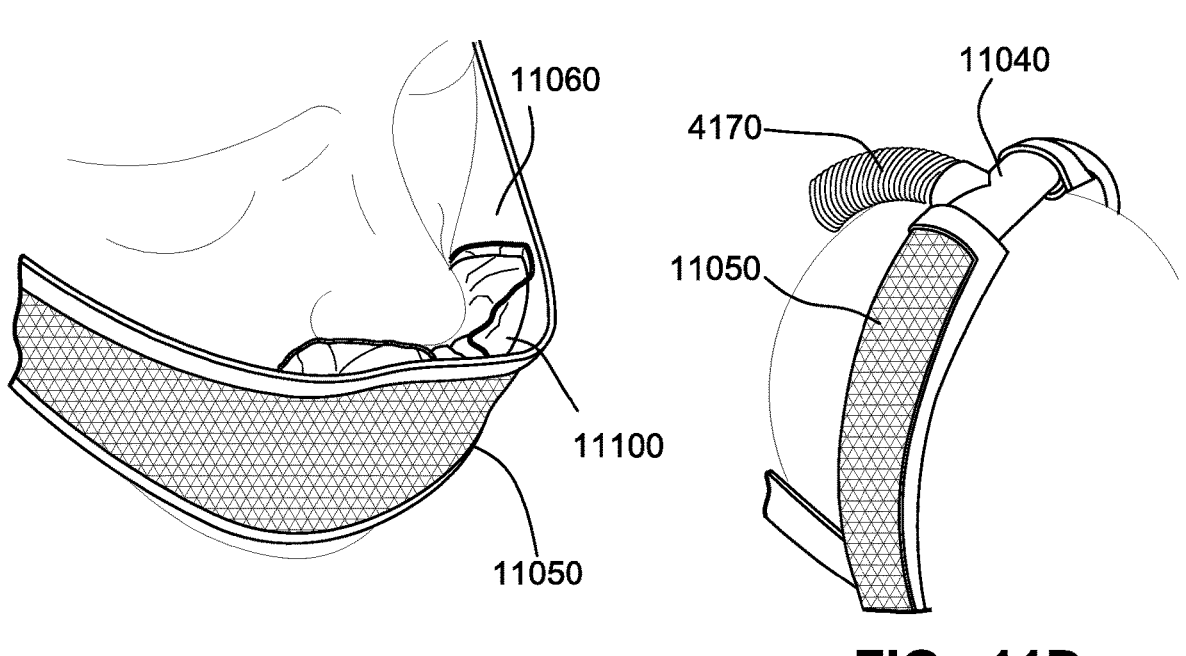
FIG. 11C
FIG. 11D

11000

11050a

11050b

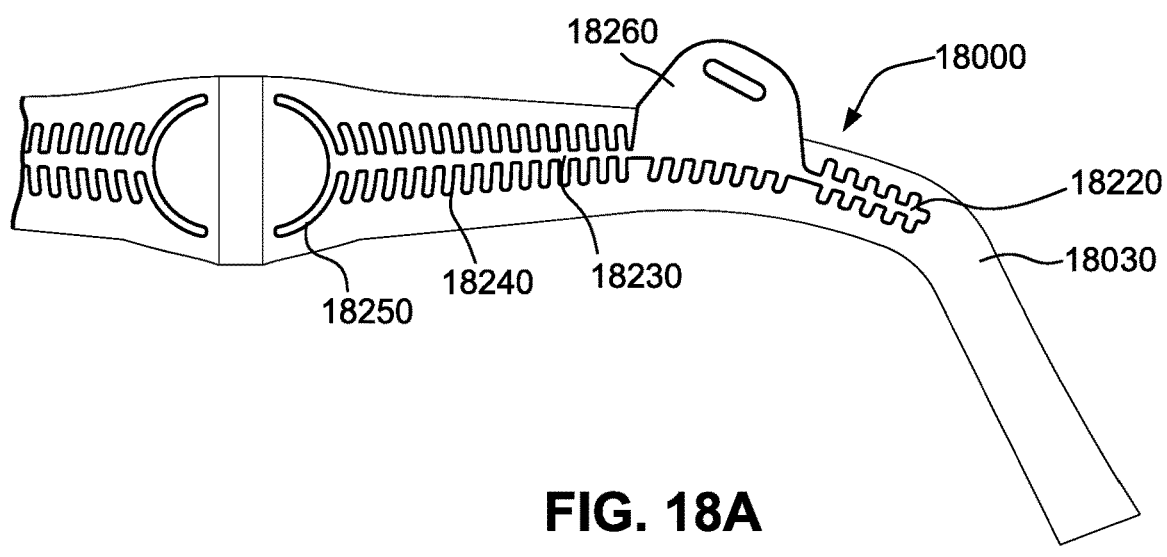
FIG. 18A
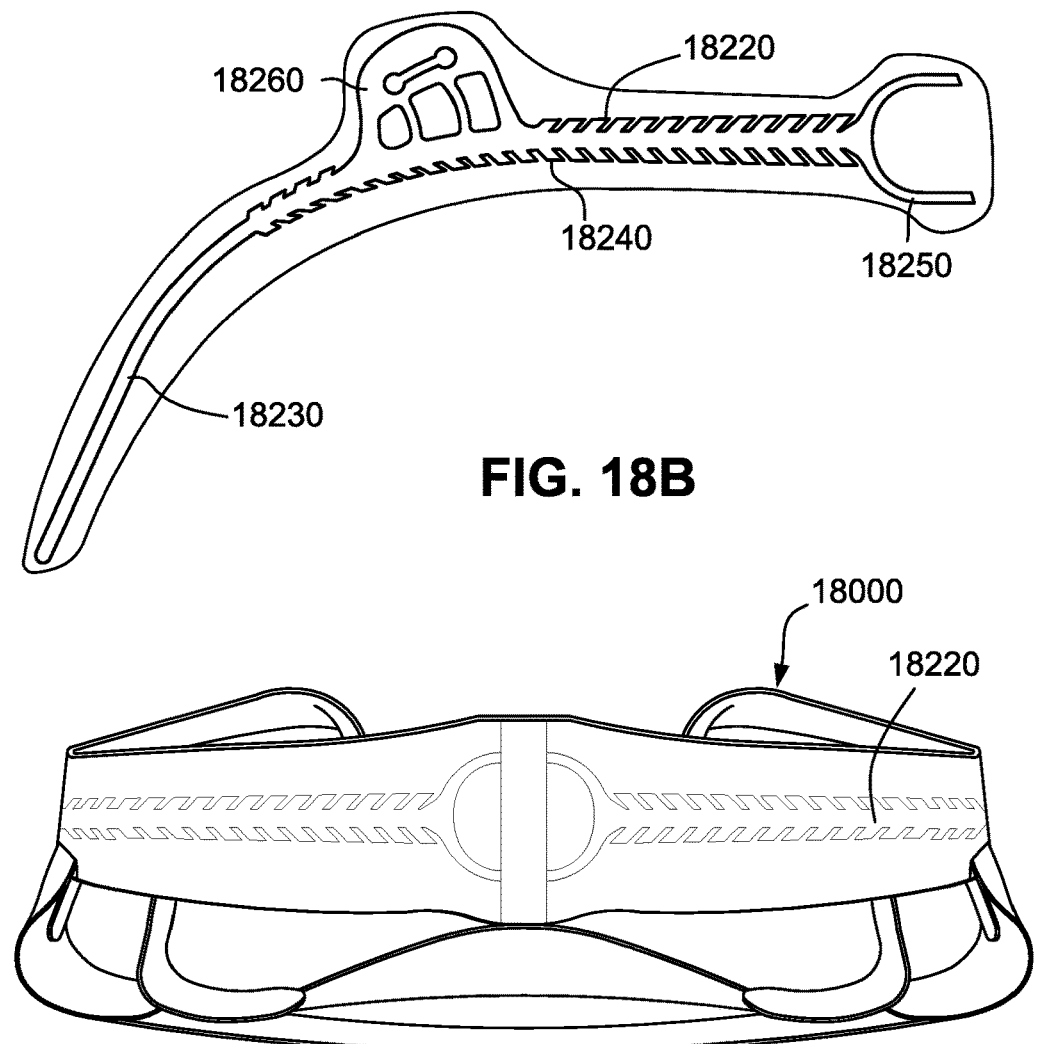
FIG. 18B
FIG. 18C

INFLATABLE HEADGEAR AND PATIENT INTERFACE

CROSS-REFERENCE TO RELATED APPLICATIONS

This application is the U.S. national phase of International Application No. PCT/SG2021/050382 filed Jun. 30, 2021 which designated the U.S. and claims priority to SG 10202011064U filed Nov. 6, 2020, and SG 10202006317V filed Jun. 30, 2020, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application claims the benefit of Singapore Patent Application No. 10202006317V, filed Jun. 30, 2020, and Singapore Patent Application No. 102020110640, filed 6 Nov. 2020, the contents of each of which are incorporated herein by reference in their entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *"Respiratory Physiology"*, by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient CO2 to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired CO2 from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Pressurised Air Conduit

In one type of treatment system, a flow of pressurised air is provided separately to a patient interface through a conduit in an air circuit that fluidly connects to the patient interface so that, when the patient interface is positioned on the patient's face during use, the conduit extends out of the patient interface forwards away from the patient's face. This may sometimes be referred to as an "elephant trunk" style of interface.

Some patients find such interfaces to be unsightly and are consequently deterred from wearing them, reducing patient compliance. Additionally, conduits connecting to an interface at the front of a patient's face may sometimes be vulnerable to becoming tangled up in bed clothes.

2.2.3.1.2 Pressurised Air Conduit used for Positioning/Stabilising the Seal-Forming Structure An alternative type of treatment system which seeks to address these problems comprises a patient interface in which a tube that delivers pressurised air to the patient's airways also functions as part of the headgear to position and stabilise the seal forming portion of the patient interface to the appropriate part of the patient's face. This type of patient interface may be referred to as incorporating 'headgear tubing', or as 'conduit headgear'. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. 2007/0246043, the contents of which are incorporated herein by reference, in which the conduit connects to a tube in the patient interface through a port positioned in use on top of the patient's head.

The Philips DreamWear™ mask includes such headgear tubing. The length of the DreamWear™ headgear tubes cannot be adjusted. Consequently, the DreamWear™ headgear is supplied in three different sizes to cater for different sized patient faces. Providing a greater number of different sizes may increase the complexity and cost to manufacture the headgear and may result in larger packaging. Additionally, a supply of discretely sized masks may limit the extent to which differently sized patient heads can be accommodated. There may be a greater chance of some patients being unable to achieve what they consider a "perfect" fit if forced to choose between discrete sizes that are not adjustable in length.

Patient interfaces incorporating headgear tubing may provide some advantages, for example avoiding a conduit connecting to the patient interface at the front of a patient's face, which may be unsightly and obtrusive. However, it is desirable for patient interfaces incorporating headgear tubing to be comfortable for a patient to wear over a prolonged duration when the patient is asleep while forming an effective seal with the patient's face.

2.2.3.1.3 Seal-Forming Structure

Patient interfaces may include a seal-forming structure. Since it is in direct contact with the patient's face, the shape and configuration of the seal-forming structure can have a direct impact on the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design can fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.4 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango™ | 31.9 | 2007 |
| C-Series Tango™ with Humidifier | 33.1 | 2007 |
| S8 Escape™ II | 30.5 | 2005 |
| S8 Escape™ II with H4i™ Humidifier | 31.1 | 2005 |
| S9 AutoSet™ | 26.5 | 2010 |
| S9 AutoSet™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers.

While a number of medical humidifiers are known, they can suffer from one or more shortcomings. Some medical humidifiers may provide inadequate humidification, some are difficult or inconvenient to use by patients.

2.2.3.5 Oxygen Source

Experts in this field have recognized that exercise for respiratory failure patients provides long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks or cylinders mounted on a cart with dolly wheels. The disadvantage of these tanks is that they contain a finite amount of oxygen and are heavy, weighing about 50 pounds when mounted.

Oxygen concentrators have been in use for about 50 years to supply oxygen for respiratory therapy. Traditional oxygen concentrators have been bulky and heavy making ordinary ambulatory activities with them difficult and impractical. Recently, companies that manufacture large stationary oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed. POCs seek to utilize their produced oxygen as efficiently as possible, in order to minimise weight, size, and power consumption. This may be achieved by delivering the oxygen as series of pulses, each pulse or "bolus" timed to coincide with the onset of inhalation. This therapy mode is known as pulsed oxygen delivery (POD) or demand mode, in contrast with traditional continuous flow delivery more suited to stationary oxygen concentrators.

2.2.3.6 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.7 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed MirageTM (*) | nasal | 29.5 | 21.5 | 1998 |

-continued

| Mask name | Mask type | A-weighted sound power level dB(A) (uncertainty) | A-weighted sound pressure dB(A) (uncertainty) | Year (approx.) |
|---|---|---|---|---|
| ResMed UltraMirageTM | nasal | 36 (3) | 28 (3) | 2000 |
| ResMed Mirage ActivaTM | nasal | 32 (3) | 24 (3) | 2002 |
| ResMed Mirage MicroTM | nasal | 30 (3) | 22 (3) | 2008 |
| ResMed MirageTM SoftGel | nasal | 29 (3) | 22 (3) | 2008 |
| ResMed MirageTM FX | nasal | 26 (3) | 18 (3) | 2010 |
| ResMed Mirage SwiftTM (*) | nasal pillows | 37 | 29 | 2004 |
| ResMed Mirage SwiftTM II | nasal pillows | 28 (3) | 20 (3) | 2005 |
| ResMed Mirage SwiftTM LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular, it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

It would be desirable to overcome or ameliorate at least one of the above-described problems, or at least to provide a useful alternative.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

A patient interface comprising: a plenum chamber pressurisable to a therapeutic pressure of at least 6 cmH₂O above ambient air pressure; a seal-forming structure constructed and arranged to form a seal with a region of the patient's face surrounding an entrance to the patient's airways for delivery of the flow of air at the therapeutic pressure of at least 6 cmH₂O above ambient air pressure throughout the patient's respiratory cycle in use; and a headgear for providing a force to hold the seal-forming structure in a therapeutically effective position on a patient's head.

One form of the present technology comprises a headgear and/or patient interface for delivery of a supply of pressurised breathable gas or air to an entrance of a patient's airway.

One form of the present technology is directed to a headgear. The headgear is for providing a force to hold a seal-forming structure in a therapeutically effective position on the patient's head, the seal-forming structure constructed and arranged to form a seal with a region of the patient's face surrounding an entrance to the patient's airways for delivery of a flow of air at a therapeutic pressure of at least 6 cmH₂O above ambient air pressure throughout the patient's respiratory cycle in use. The headgear comprises at least one air inlet, at least one air outlet positionable in fluid communication with the seal-forming structure when in use, a headgear tubing extending between the air inlet and the air outlet, and a tensioning structure for providing a force to maintain the seal-forming structure in the as-used position. The headgear tubing is dimensioned such that it is expandable in one direction from a collapsed state to an inflated state to form a conduit for supplying pressurised air to the patient. When the headgear tubing is in the collapsed state, the headgear tubing is foldable on itself.

In certain forms, the headgear tubing further includes a fastening portion fluidly connecting at least two pieces of material at least partially forming the headgear tubing. The fastening portion is movable between a first position and a second position. The interior of the passage is exposed to the ambient in the first position. The passage is configured to convey the flow of air between the at least one air inlet and the at least one air outlet in the second position.

In certain forms, a) fastening portion is a zip, tape, or a hook and loop fastener; b) the fastening portion is formed as part of a double walled film, and is configured to expose an inner surface of the double walled film in the open position; c) the fastening portion extends at least partially between the at least one air inlet and the at least one air outlet; d) the fastening portion is in the first position proximate to the at least one air outlet and is in the second position proximate to the at least one air inlet; and/or e) the fastening portion is disposed on a non-patient contacting side of the headgear tubing.

One form of the present technology is directed to a headgear. The headgear is for providing a force to hold a seal-forming structure in a therapeutically effective position on the patient's head, the seal-forming structure constructed and arranged to form a seal with a region of the patient's face surrounding an entrance to the patient's airways for delivery of a flow of air at a therapeutic pressure of at least 6 cmH$_2$O above ambient air pressure throughout the patient's respiratory cycle in use. The headgear comprises at least one air inlet positionable to overlie a cranial region of a patient's head in an as-used position (or when in use), at least one air outlet positionable in fluid communication with the seal-forming structure when in the as-used position, a headgear tubing extending between the air inlet and the air outlet, and a tensioning structure for providing a force to maintain the seal-forming structure in the as-used position. The headgear tubing is dimensioned such that it is expandable in one direction from a collapsed state to an inflated state to form a conduit for supplying pressurised air to the patient. When the headgear tubing is in the collapsed state, the headgear tubing is foldable on itself.

An advantage of the headgear as described in the previous paragraph is that it is less bulky than previously known headgear, and as the air tubing is integral with the headgear, it is easier to use as the patient does not need to attach clips or straps to secure loose parts. The headgear conduit allows for a good fit to a patient's head for improved comfort of use. When collapsed, the headgear can be deformed and folded into a compact size for storage.

Another form of the present technology is directed to a headgear for supplying pressurised air to a patient. The headgear is for providing a force to hold a seal-forming structure in a therapeutically effective position on the patient's head, the seal-forming structure constructed and arranged to form a seal with a region of the patient's face surrounding an entrance to the patient's airways for delivery of a flow of air at a therapeutic pressure of at least 6 cmH$_2$O above ambient air pressure throughout the patient's respiratory cycle in use. The headgear comprises a headgear tubing. The headgear tubing is formed from a composite material, comprising a double walled film having an inner cavity and an outer surface. The outer surface comprises a first side and a second side. The film is impervious to pressurised air. A first fabric layer is connected to the first side and a second fabric layer is connected to the second side. The headgear tubing has a first transverse axis extending generally transversely of the headgear tubing along its length, and a second transverse axis extending generally transverse to the first transverse axis. The headgear tubing is more expandable in a first direction along the first transverse axis than in a second direction along the second transverse axis.

The headgear is less bulky than previous headgear arrangements, and is easier for the patient to don on or off the headgear. When inflation occurs preferentially in a direction along one transverse axis, the headgear allows for a good fit to a patient's head for improved comfort. The inflated state also provides a "cushion" effect when the patient lies on his side. The textile may be provided with properties for temperature and moisture management to enhance the comfort level of the patient. When collapsed, the headgear is scrunchable and can be folded into a compact size for storage.

In some embodiments, the composite material has a flexural modulus of less than 15 N/mm$^2$.

Advantageously, the composite material being within the flexural modulus range as disclosed herein allows for the headgear to be scrunchable such that the headgear can be compacted and folded into a compact size for storage when not in use. This deformability allows the headgear to change its shape in response to compression force, and still revertible to its use configuration when the compression force is removed. The flexibility of the composite material also allows the headgear to inflate even at low air pressure settings of at least 6 cmH$_2$O above ambient air pressure.

The headgear tubing can be made of a material that is stretchable. To this end, the composite material may have a Young's modulus of about 15 N/mm$^2$ to about 150 N/mm$^2$. The headgear tubing can be more stretchable along at least part of its length relative to the second transverse axis.

Advantageously, the directional or non-uniform stretchability of the headgear tubing allows for a good fit to the patient's head, by allowing a wider fit curve without sacrificing conduit stiffness. This can be imparted by material property such as tensile modulus, and/or by shaping the material to an appropriate form. For example, a curved shape can be formed which allows for flexing of the headgear. This stretchability allows the headgear to stretch beyond its original cross-section and/or length to accommodate different head sizes.

In some embodiments, the Young's modulus along the length of the tubing of the headgear tubing is about 15 N/mm$^2$ to about 150 N/mm$^2$.

In some embodiments, the first fabric layer further comprises a fastening portion that is openable to expose the film. The fastening portion is in contact with the headgear tubing along its length. The fastening portion can extend from a first position proximate to the inlet to a second position proximate to the outlet.

The fastening portion, when opened, allows the patient to access the inner cavity of the double walled film of the headgear tubing. This facilitates cleaning of the cavity, thus providing patient assurance regarding the hygiene of the product.

In some embodiments, the first fabric layer is a mesh fabric layer.

In some embodiments, the headgear tubing is flat when in the collapsed state.

In some embodiments, the headgear tubing further comprises an air vent. The air vent is positionable near the outlet of the headgear.

The action of the patient breathing out and expelling carbon dioxide can thus be combined with the release of excess pressurised air from the headgear tubing. Better regulation and flow of air to the patient's nares can be obtained. Further, the accumulation of carbon dioxide within the headgear tubing can be avoided. Placement of the vents at an appropriate location enables good CO$_2$ wash out and maintenance of therapy pressure within the intended limits.

In some embodiments, the headgear tubing when in the inflated state is arranged to conform to a contour of a patient's head.

In some embodiments, the headgear tubing has a flexural modulus of less than 15 N/mm$^2$.

In some embodiments, the second fabric layer is annealed to the first fabric layer.

In some embodiments, the film has a total transmittance of more than 90%.

In some embodiments, the film is selected from thermoplastic polyurethane.

In some embodiments, the first fabric layer is laminated to the first side via thermal bonding or glue bonding. In some embodiments, the second fabric layer is laminated to the second side via thermal bonding or glue bonding.

In some embodiments, the first fabric layer has a knit structure selected from single jersey, rib, interlock, raschel, or jacquard.

In some embodiments, the second fabric layer is selected from microfiber yarns, nylon 6,6, peach-skin finish, elastic knitted fabric, two way stretch, non stretch, circular knit fabric, woven fabric, or warp knit fabric.

In some embodiments, the second fabric layer is surface treated with a hydrophobic coating.

In some embodiments, the composite material further comprises a foam sandwiched between the second fabric layer and the second side of the double walled film.

The foam can act as a cushion which presses against the patient's head/face when the headgear is inflated, allowing for better comfort.

In some embodiments, the tensioning structure is positionable to overlie a posterior region of the patient's head. The tensioning structure can have elasticity.

The tensioning structure allows for stretch fit and a constant compression force to be applied on the patient's head. This allows for a one size fits all function.

One form of the present technology is directed to a patient interface, comprising the headgear as disclosed herein, and a seal-forming structure that is integrated with or attachable to the headgear at the outlet thereof. The seal-forming structure is constructed and arranged to form a seal with a region of the patient's face surrounding an entrance to the patient's airway for delivery of air flow at a pressure of at least 6 cmH$_2$O above ambient air pressure.

One form of the present technology is directed to a patient interface comprising a headgear, a plenum chamber and a seal-forming structure. The headgear comprises at least one air inlet, at least one air outlet positionable in fluid communication with the seal-forming structure when in use, a headgear tubing extending along a length between the air inlet and the air outlet, and a tensioning structure for providing a force to maintain the seal-forming structure when in use. The headgear tubing is expandable from a collapsed state to an inflated state to form a conduit for supplying pressurised air to the patient. The headgear tubing is formed from a composite material, comprising a double walled film having an inner cavity and an outer surface. The outer surface comprises a first side and a second side. The film is impervious to pressurised air. A first fabric layer is connected to the first side and a second fabric layer is connected to the second side. The headgear tubing has a first transverse axis extending generally transversely of the headgear tubing along the length, and a second transverse axis extending generally transverse to the first transverse axis. The headgear tubing is selectively expandable in a first direction along the first transverse axis relative to a second direction along the second transverse axis. The plenum chamber is adjacent to and in fluid communication with the outlet of the headgear, and is pressurisable to a therapeutic pressure of at least 6 cmH$_2$O above ambient air pressure, said plenum chamber including a plenum chamber inlet port sized and structured to receive a flow of air at the therapeutic pressure for breathing by a patient. The seal-forming structure is adjacent to an inner surface of the outlet of the headgear, and is constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the patient interface is configured to allow the patient to breath from ambient through their mouth in the absence of a flow of pressurised air through the plenum chamber inlet port, or the patient interface is configured to leave the patient's mouth uncovered.

One form of the present technology is directed to a patient interface comprising a headgear, a plenum chamber and a seal-forming structure. The headgear comprises at least one air inlet positionable to overlie a superior region of a patient's head in an as-used position, at least one air outlet positionable in fluid communication with the seal-forming structure when in the as-used position, a headgear tubing extending along a length between the air inlet and the air outlet, and a tensioning structure for providing a force to maintain the seal-forming structure in the as-used position. The headgear tubing is expandable from a collapsed state to an inflated state to form a conduit for supplying pressurised air to the patient. The headgear tubing is formed from a composite material, comprising a double walled film having an inner cavity and an outer surface. The outer surface comprises a first side and a second side. The film is impervious to pressurised air. A first fabric layer is connected to the first side and a second fabric layer is connected to the second side. The headgear tubing has a first transverse axis extending generally transversely of the headgear tubing along the length, and a second transverse axis extending generally transverse to the first transverse axis. The headgear tubing is selectively expandable in a first direction along the first transverse axis relative to a second length along the second transverse axis. The plenum chamber is adjacent to and in fluid communication with the outlet of the headgear, and is pressurisable to a therapeutic pressure of at least 6 cmH$_2$Oabove ambient air pressure, said plenum chamber including a plenum chamber inlet port sized and structured to receive a flow of air at the therapeutic pressure for breathing by a patient. The seal-forming structure is adjacent to an inner surface of the outlet of the headgear, and is constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the patient interface is configured to allow the patient to breath from ambient through their mouth in the absence of a flow of pressurised air through the plenum chamber inlet port, or the patient interface is configured to leave the patient's mouth uncovered.

The patient interface can further comprise a vent structure to allow a continuous flow of gases exhaled by the patient from an interior of the plenum chamber to ambient, said vent structure being sized and shaped to maintain the therapeutic pressure in the plenum chamber in use.

The headgear and/or patient interface can further comprise a rigidiser or stiffener for maintaining a curved shape of the headgear and/or patient interface when in use. The rigidiser can be positioned adjacent to the headgear tubing, and can be adhered to an outer surface of the double walled film. For example, the rigidiser can be connected to the second side of the outer surface of the double walled film. In this regard, the rigidiser can be sandwiched between the second side of the outer surface of the double walled film and the second fabric layer.

The rigidiser prevents the collapse and/or flattening of the conduit, or at least in the first direction along the first translational axis, which is selectively expandable relative to the second direction along the second translational axis.

The rigidiser can comprise a spine structure extending at least partly along the headgear and/or patient interface. The rigidiser can also comprise a plurality of protrusions extending from a lateral side of the spine structure. The protrusions are spaced apart from each other at intervals along a length of the spine structure.

The rigidiser when in a 'fishbone' structure, provides support to the conduit and prevents kinks from forming. This allows the flow of breathable gas or air to be un-obstructed. Further, the headgear and/or patient interface without kinks provides a user the perception of a high quality finish which is smooth and comforting.

The rigidiser can further comprise a collar structure positioned at one end of the spine structure. For example, the collar structure can be a ring that surrounds the air inlet. The collar structure can also be a crescent shaped structure that partially surrounds the air inlet. The collar structure can provide additional support to a region surrounding an air inlet.

The rigidiser can further comprise at least one tab. When the rigidiser with a tab is formed with the inflatable conduit and the tab is extended outwardly from the inflatable conduit, a tensioning structure can be connected to the tab and thus provides additional support between the inflatable conduit and the tensioning structure.

Another aspect of one form of the present technology is a patient interface that is moulded or otherwise constructed with a perimeter shape which is complementary to that of an intended wearer.

An aspect of one form of the present technology is a method of manufacturing the headgear and/or the patient interface.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device comprising the headgear and/or the patient interface as disclosed herein that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
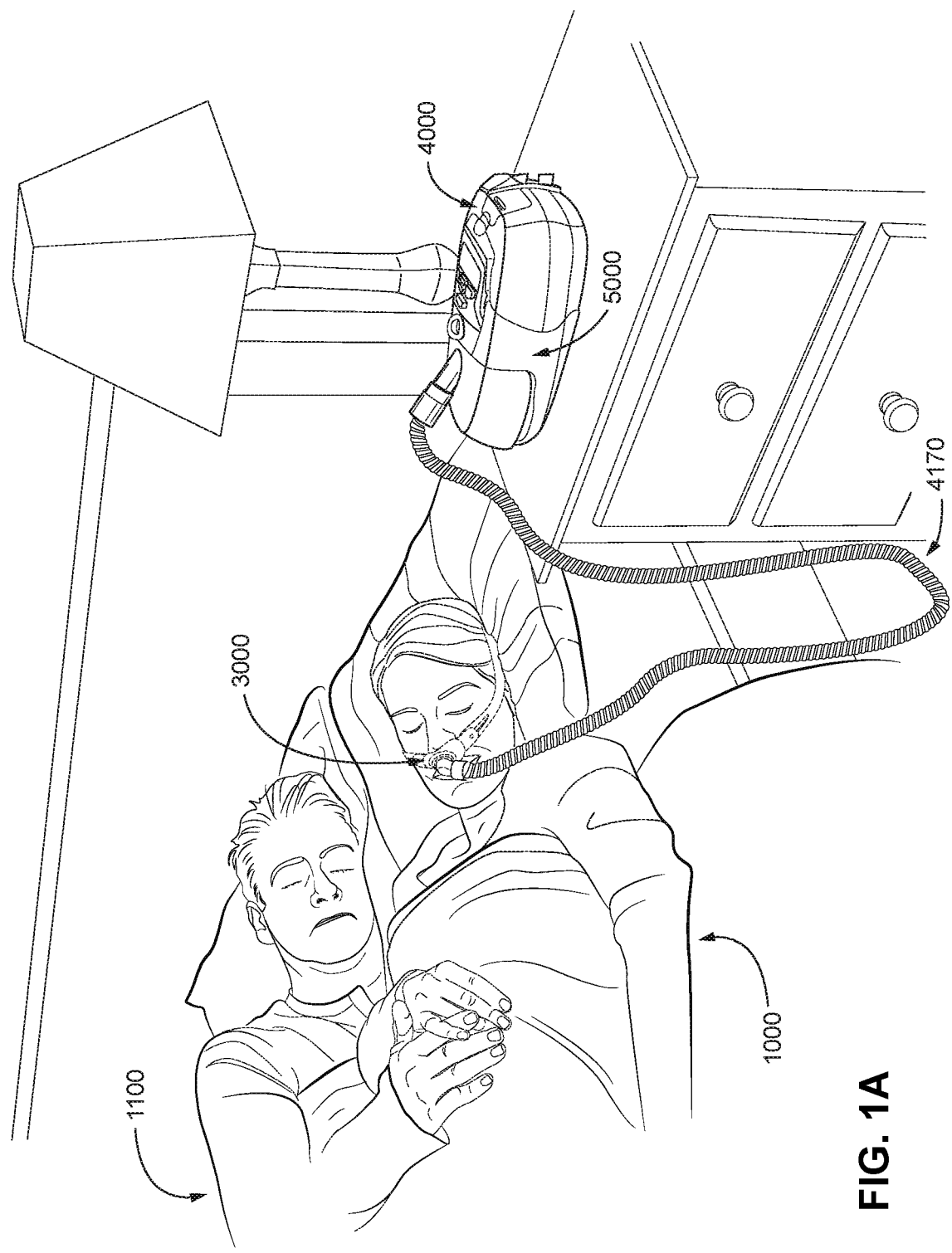
Figure 1B:
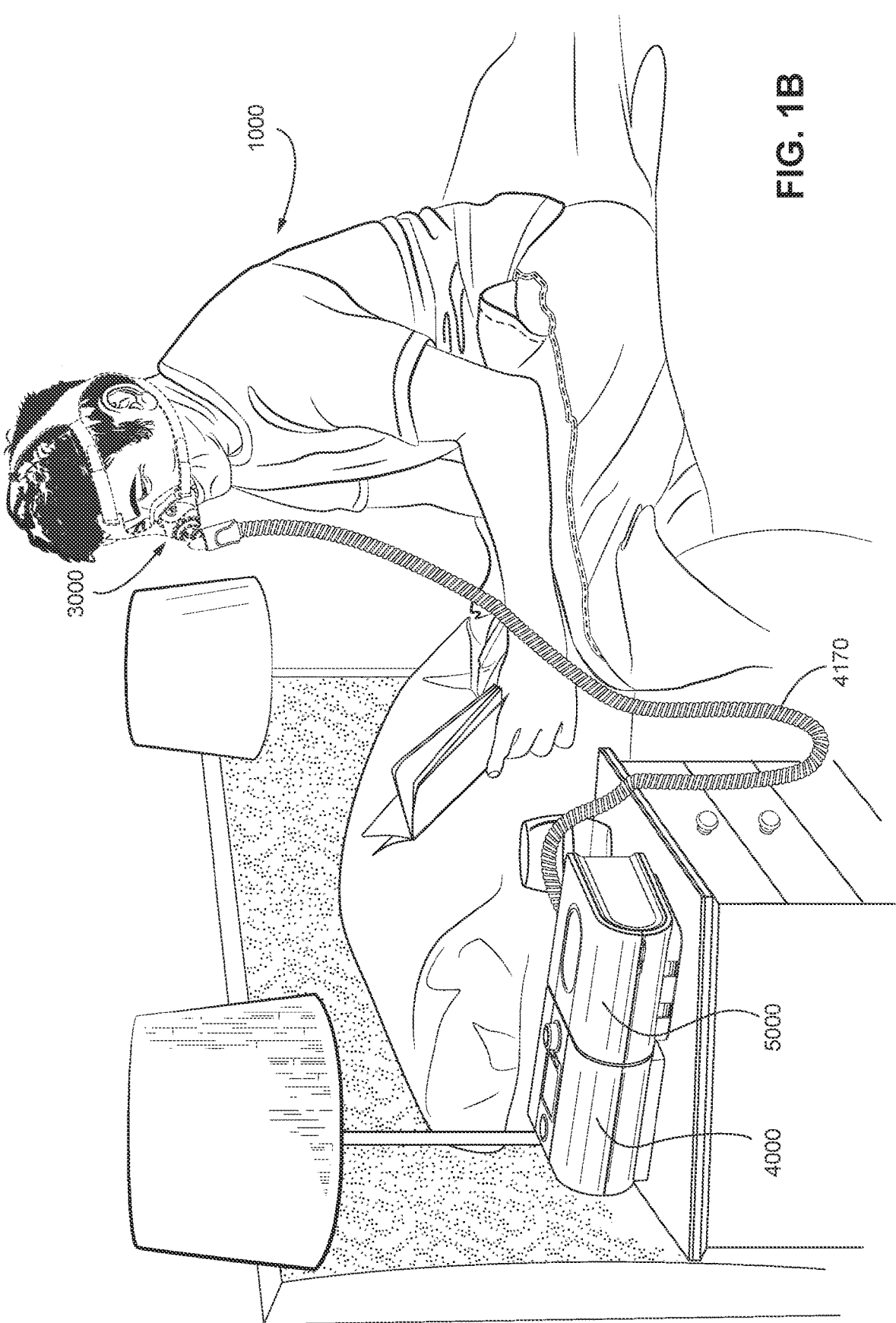
Figure 1C:
Figure 2A:
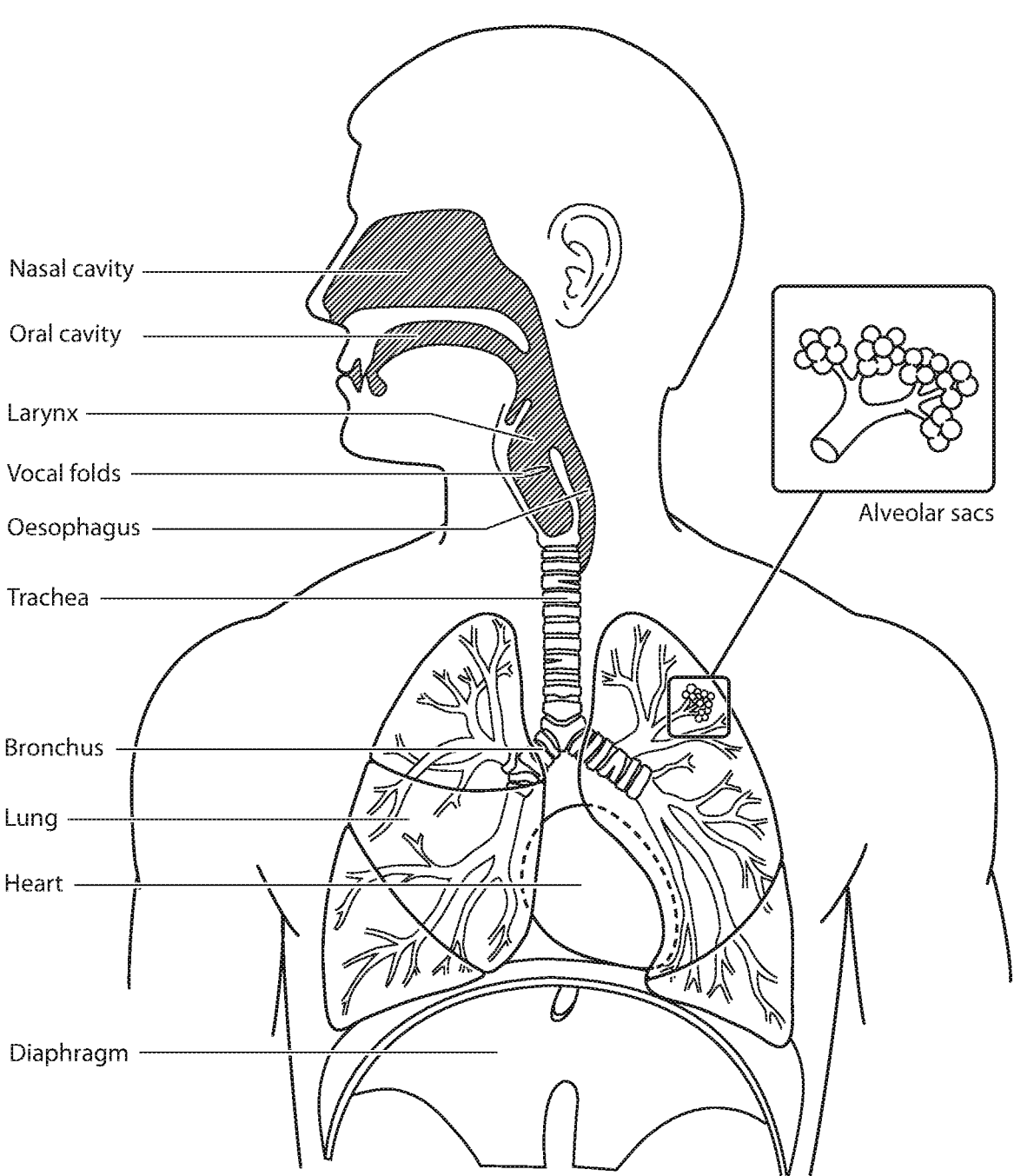
FIG. 2A shows an overview of a human respiratory system including the nasal and oral cavities, the larynx, vocal folds, oesophagus, trachea, bronchus, lung, alveolar sacs, heart and diaphragm.
Figure 2B:
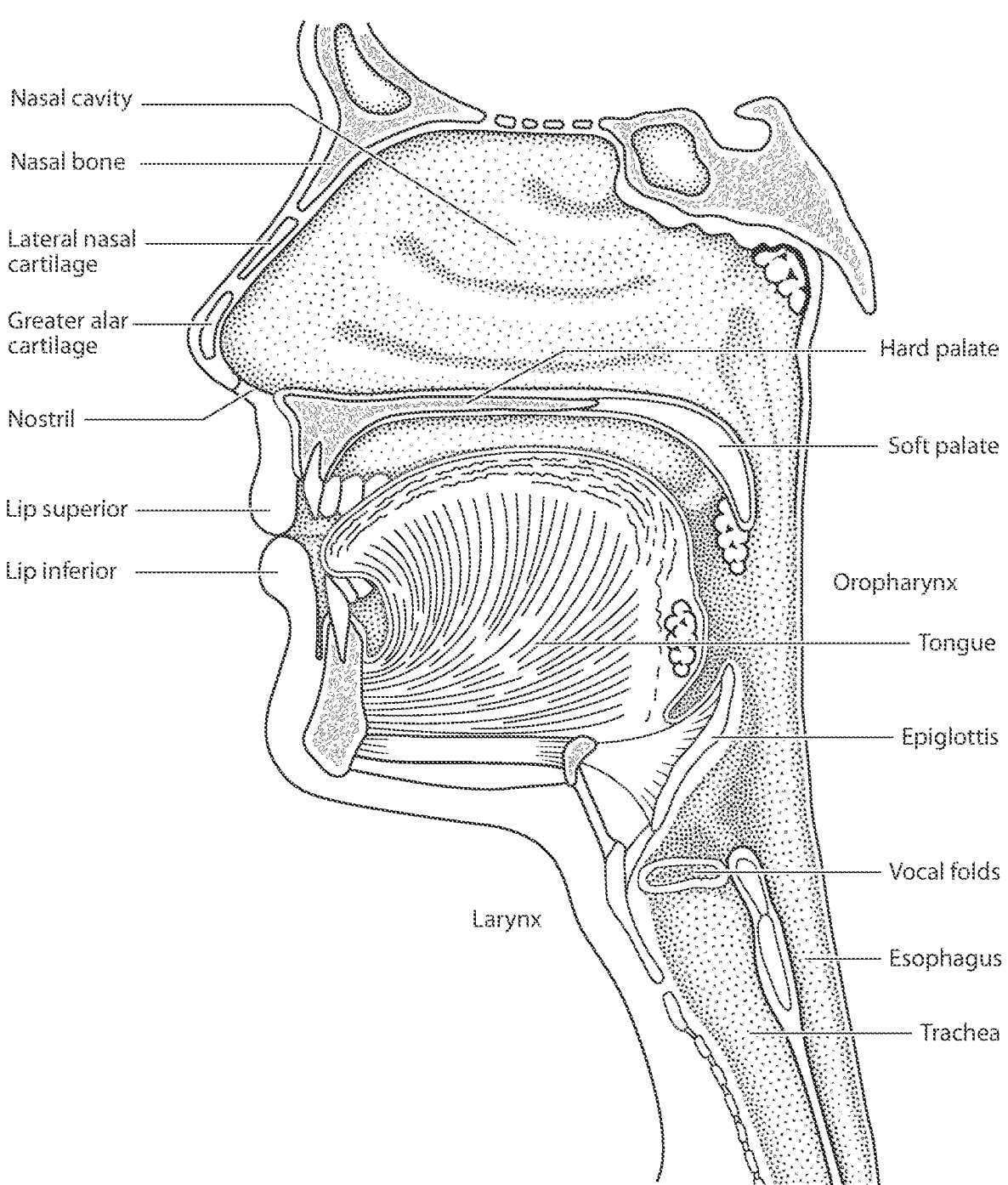
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
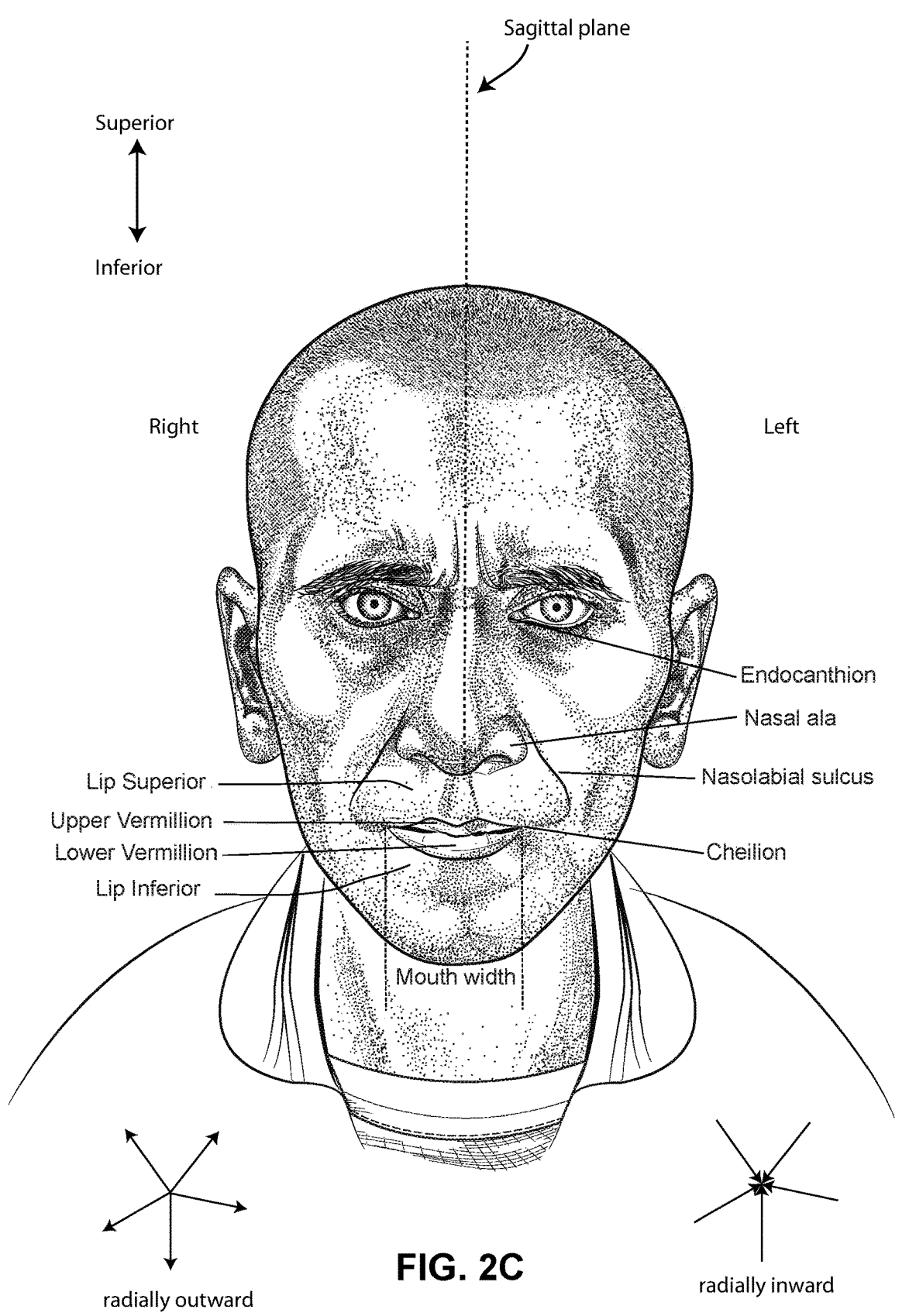
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
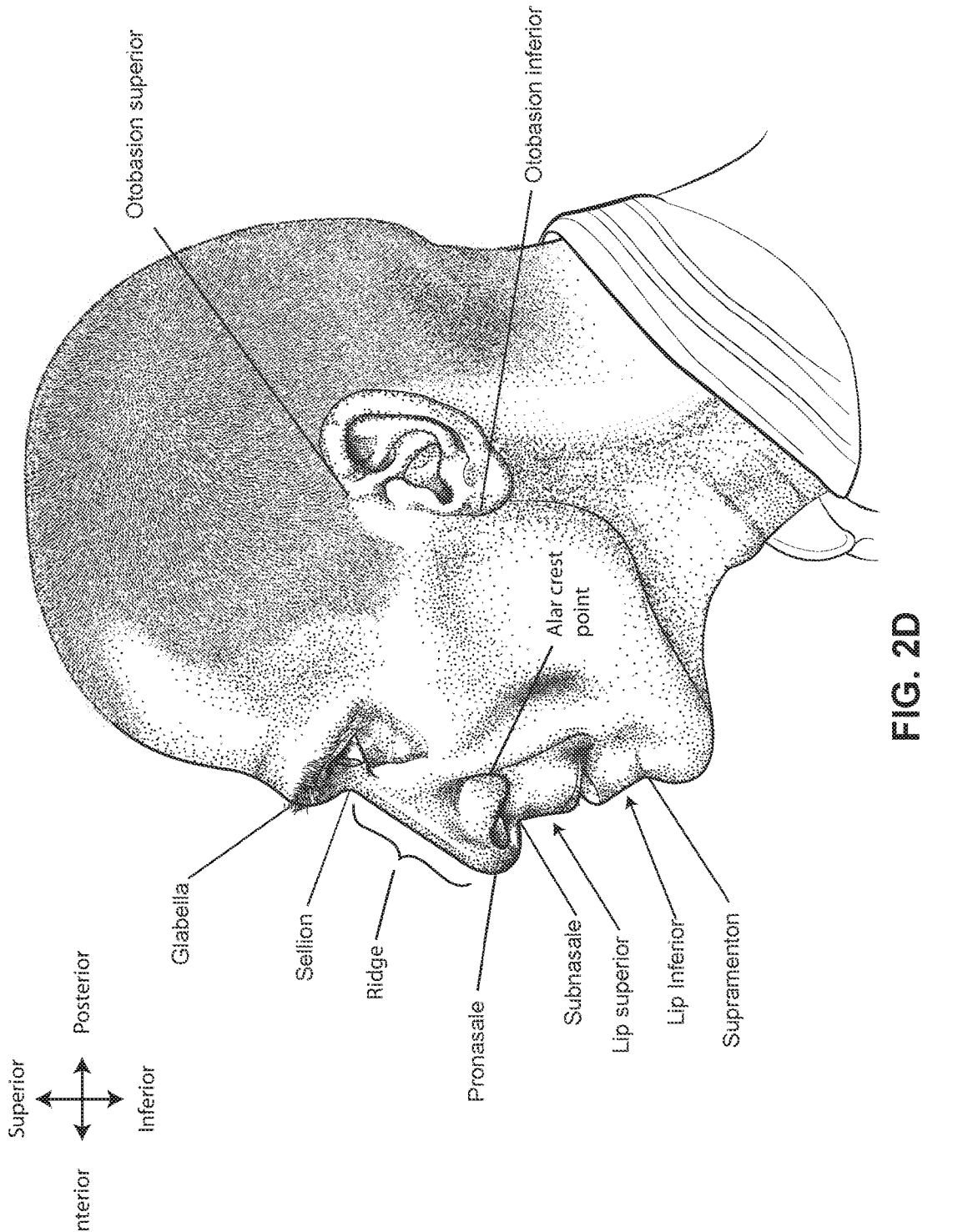
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
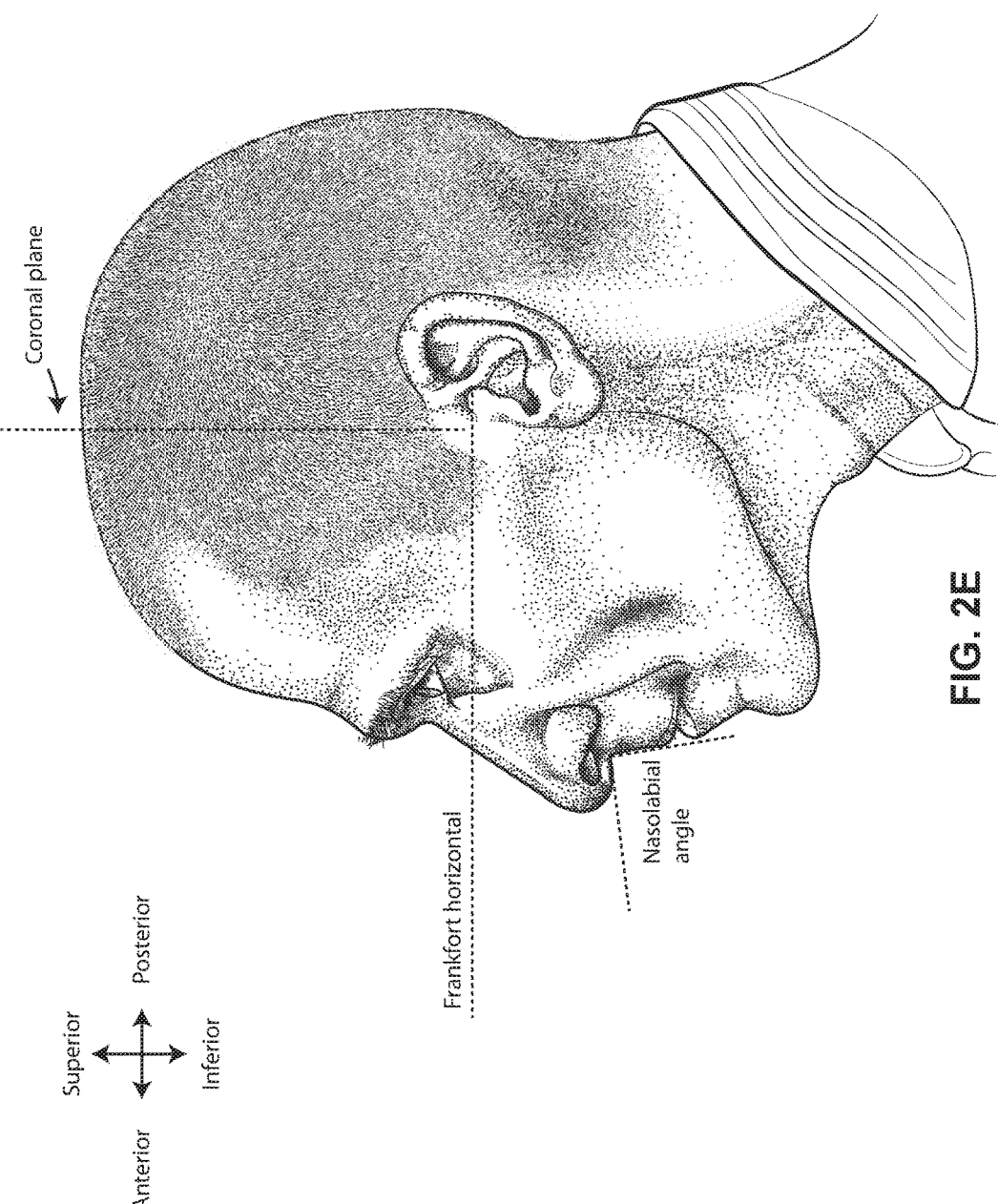

FIG. 2E is a further side view of a head. The approximate locations of the Frankfort horizontal and nasolabial angle are indicated. The coronal plane is also indicated.

Figure 2F:
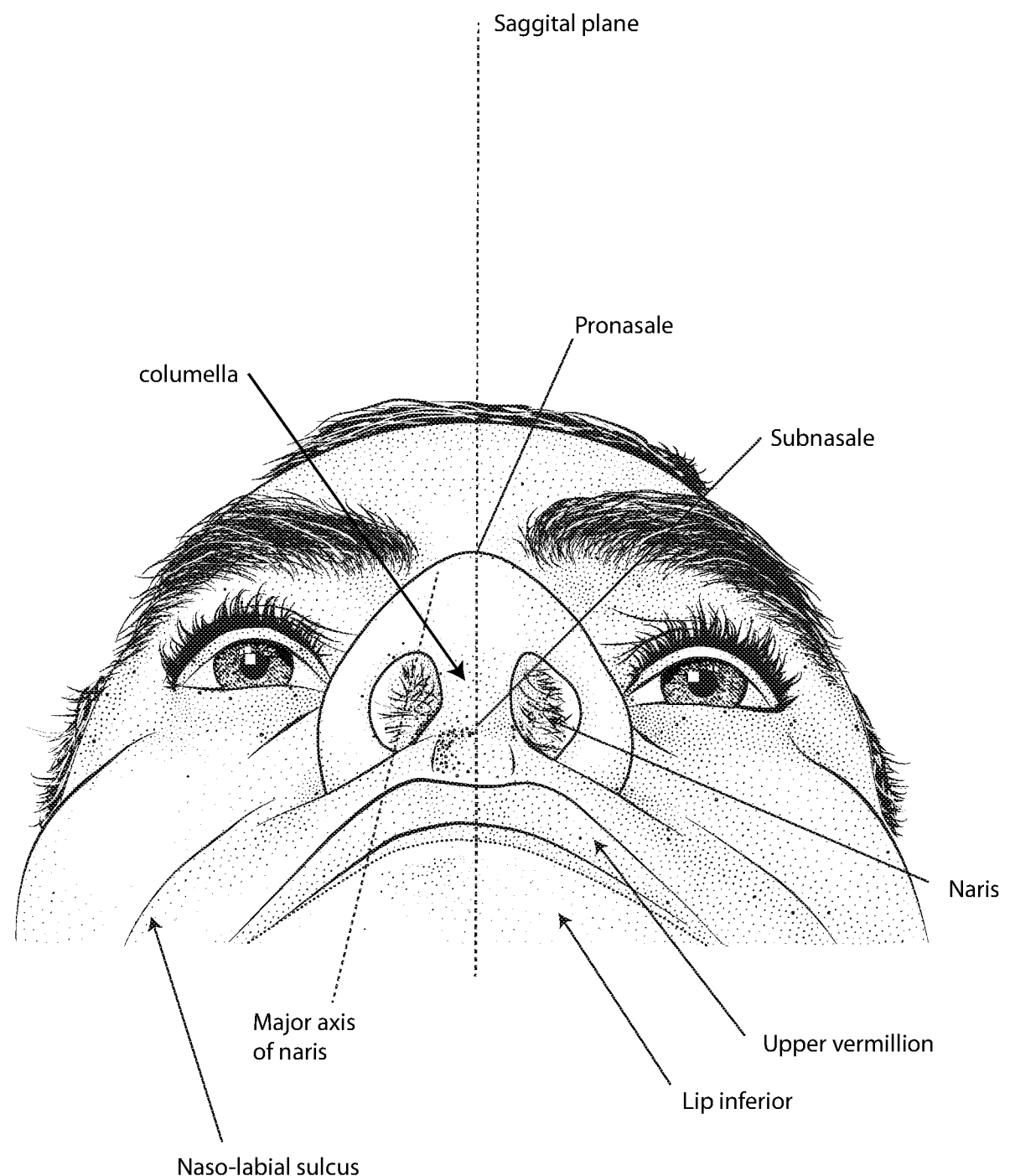

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
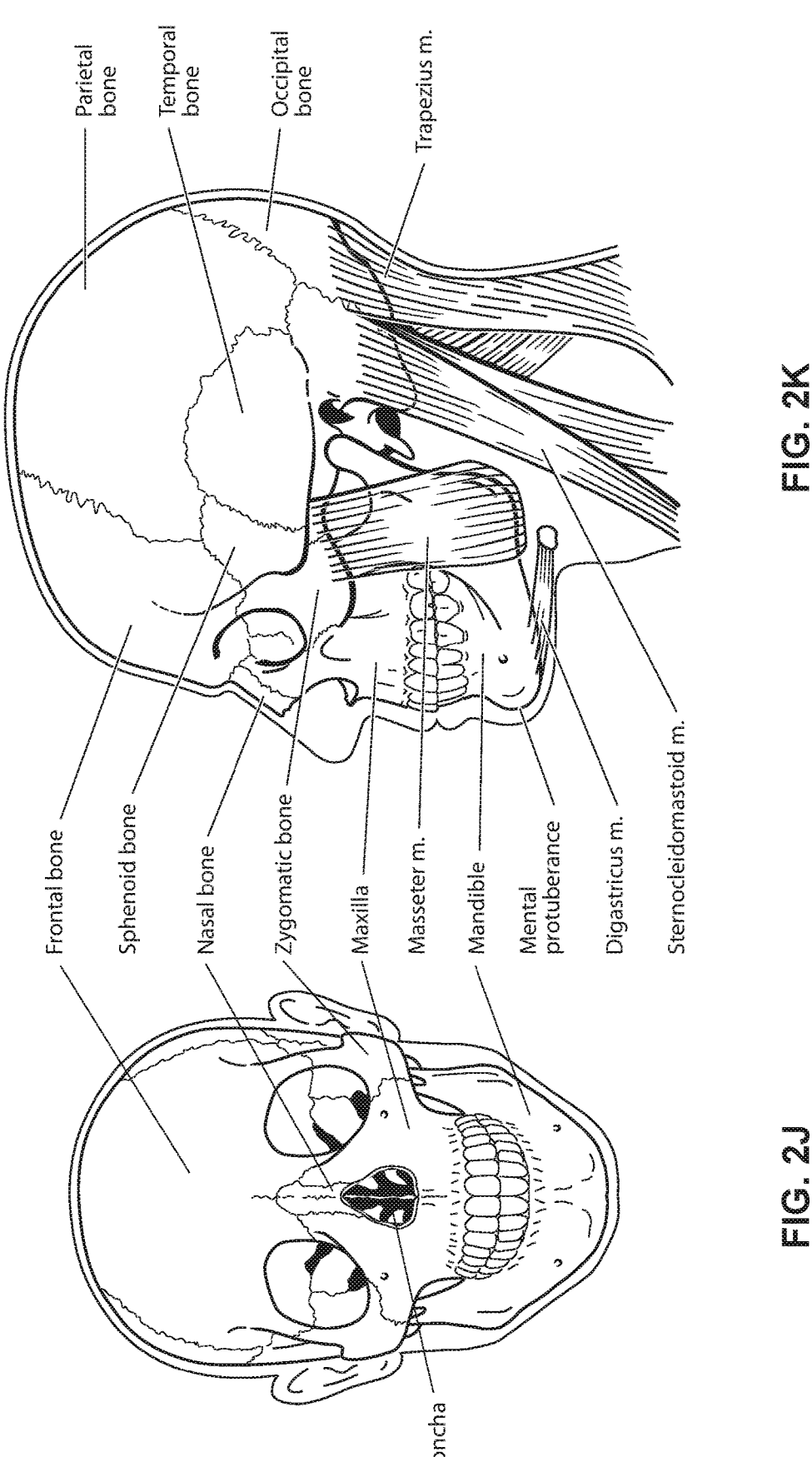

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
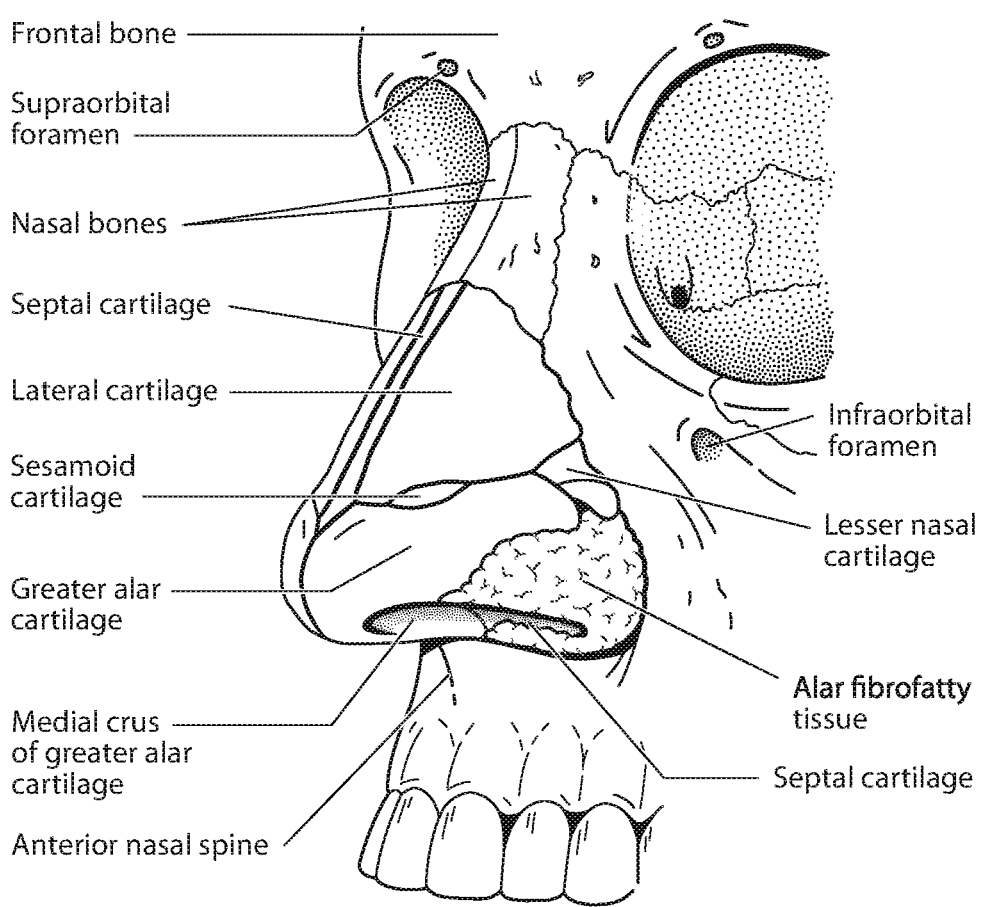

FIG. 2L shows an anterolateral view of a nose.

4.3 Patient Interface

Figure 3A:
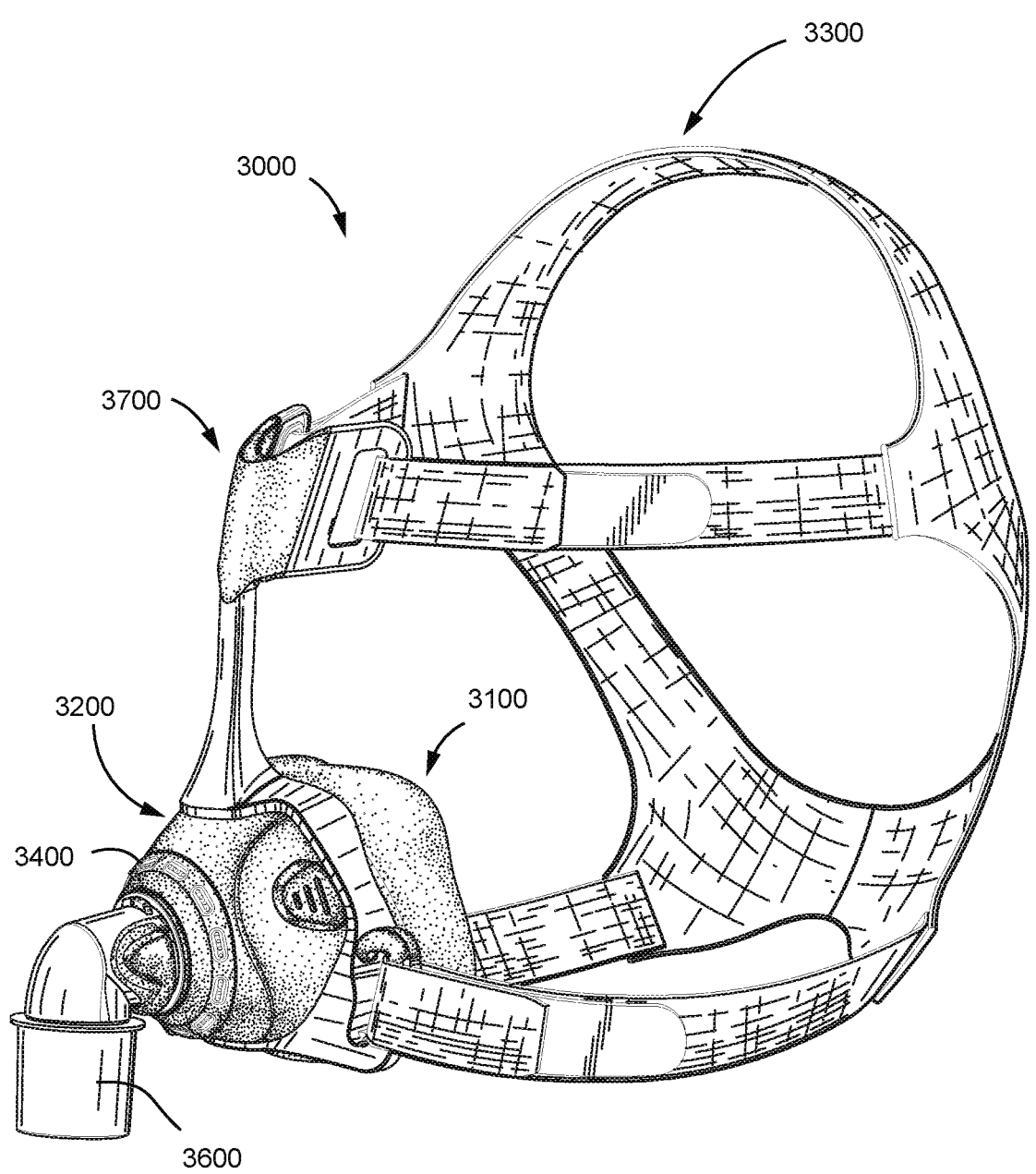

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
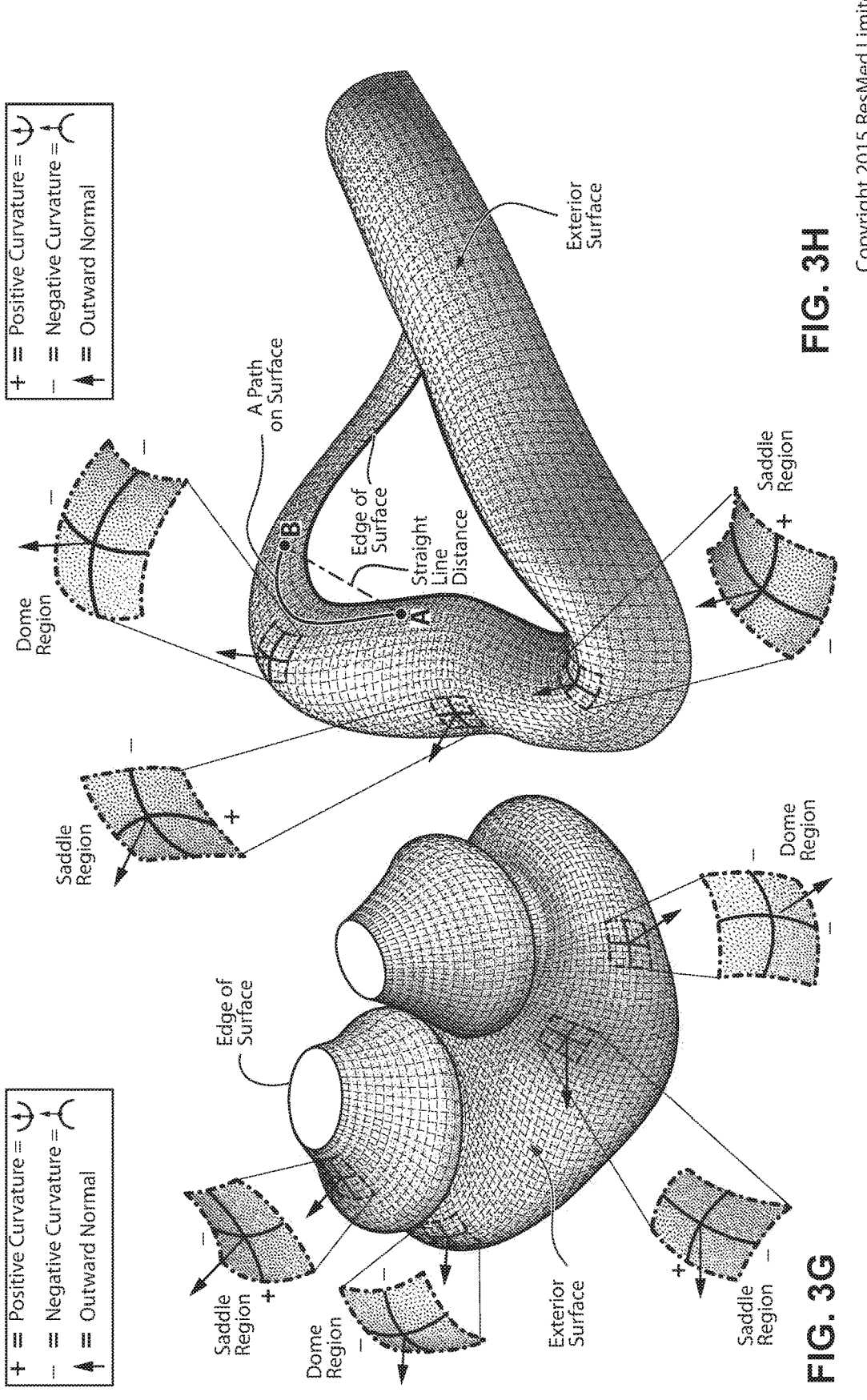

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figures 3U, 3V, 3W, 3X:
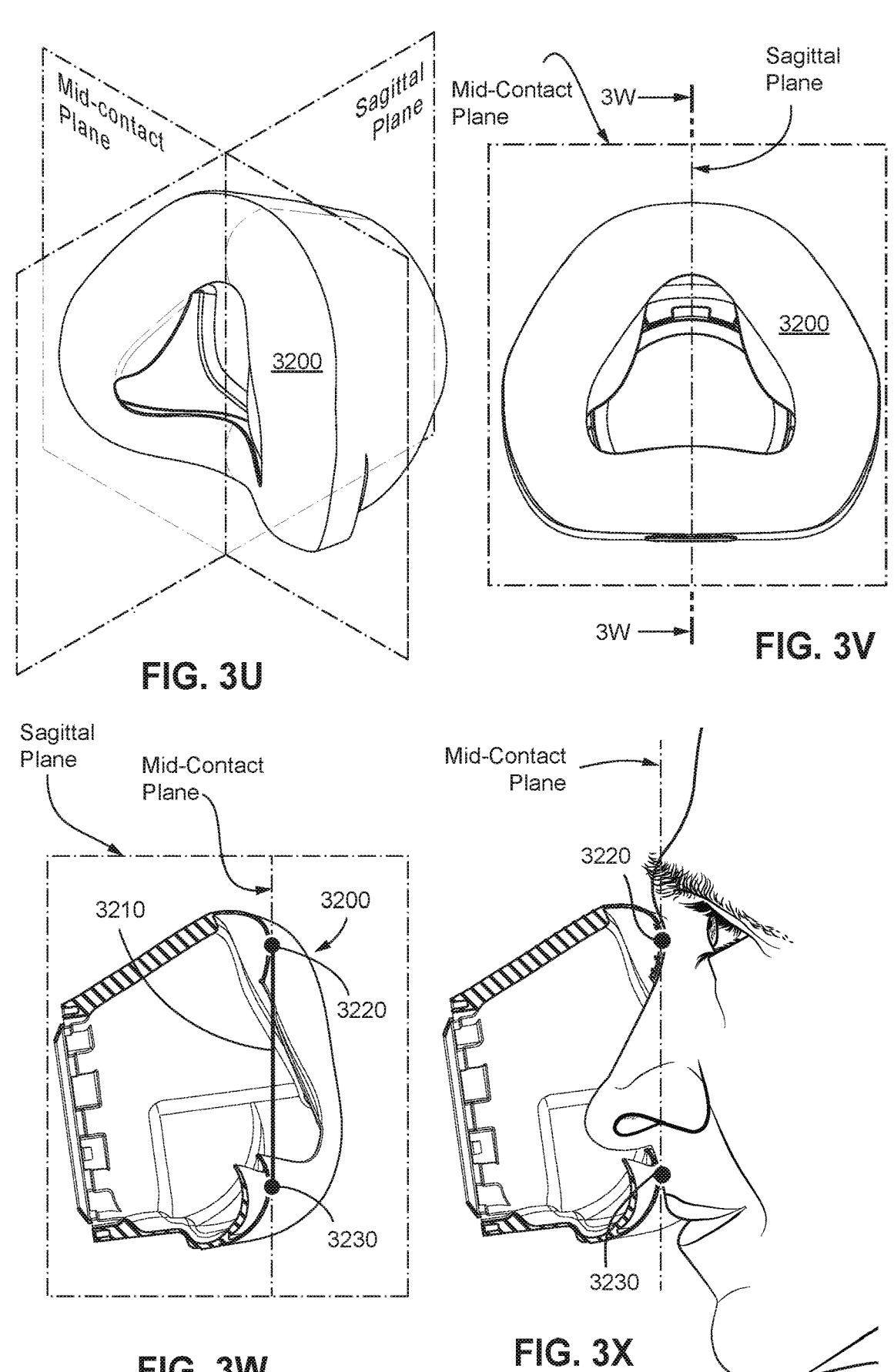

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 3Y:
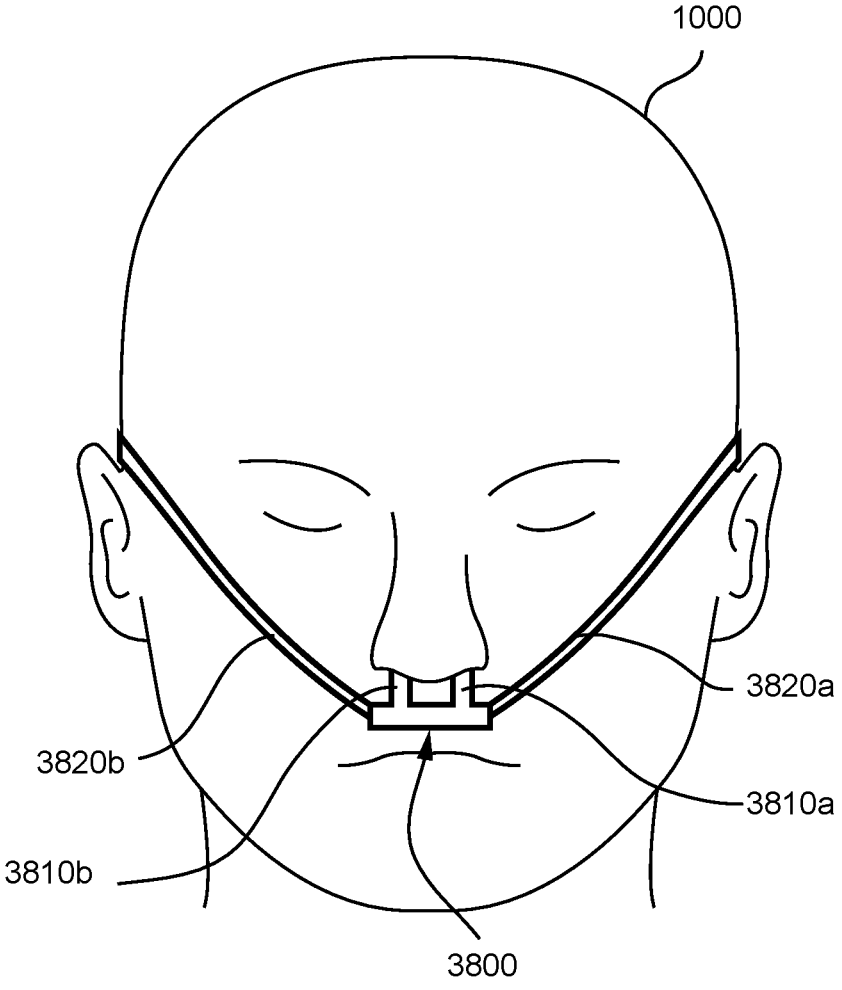

FIG. 3Y shows a patient interface in the form of a nasal cannula in accordance with one form of the present technology.

4.4 RPT Device

Figure 4A:
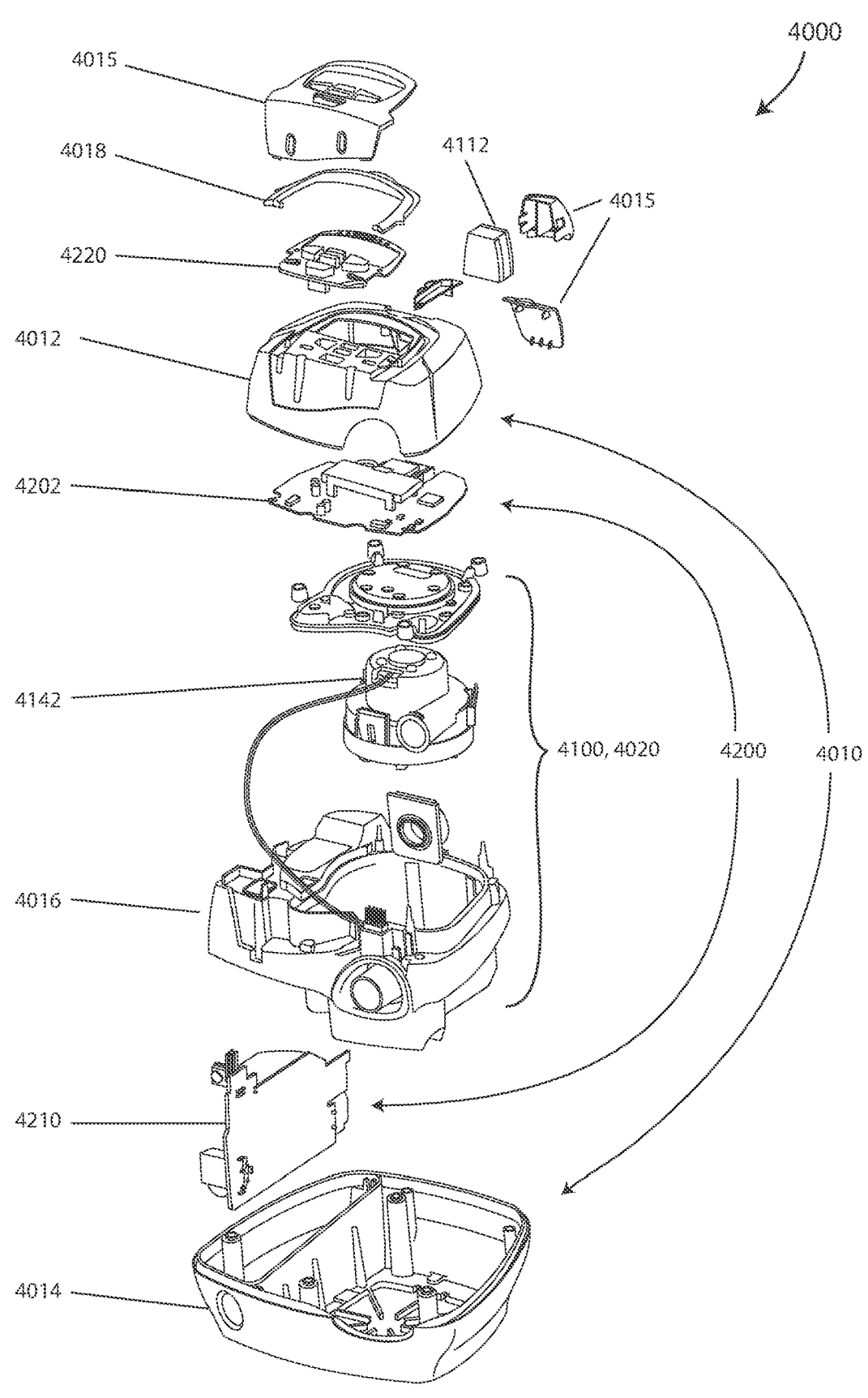

FIG. 4A shows an RPT device in accordance with one form of the present technology.

Figure 4B:
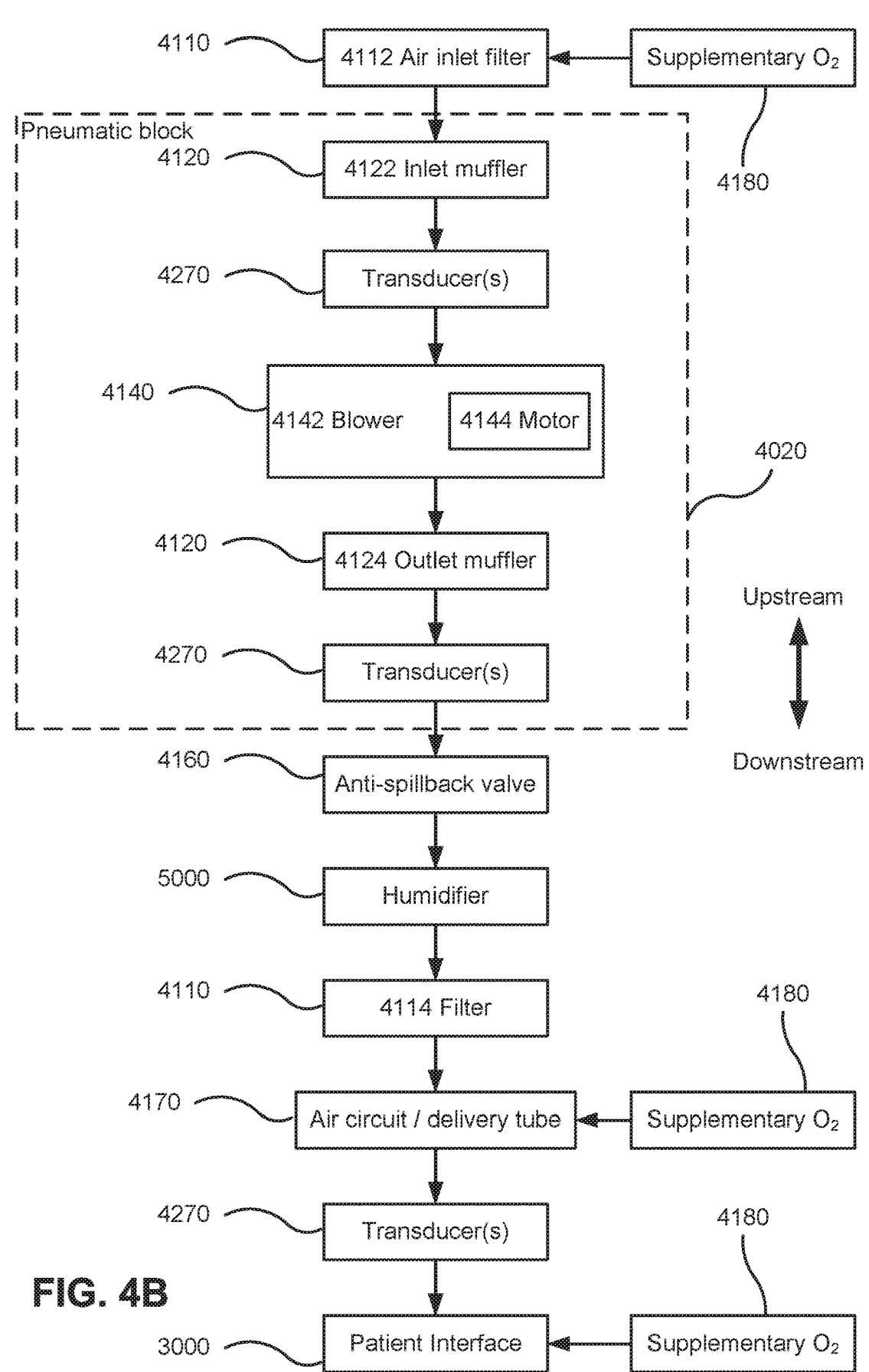

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
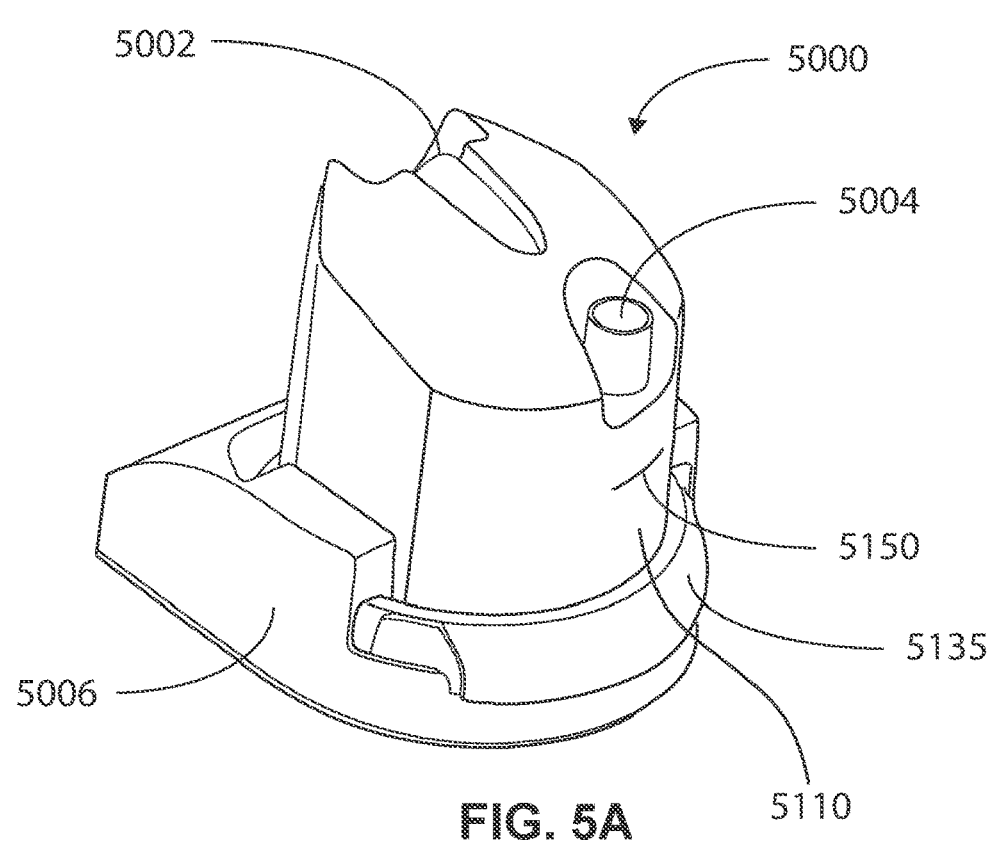

FIG. 5A shows an isometric view of a humidifier in accordance with one form of the present technology.

Figure 5B:
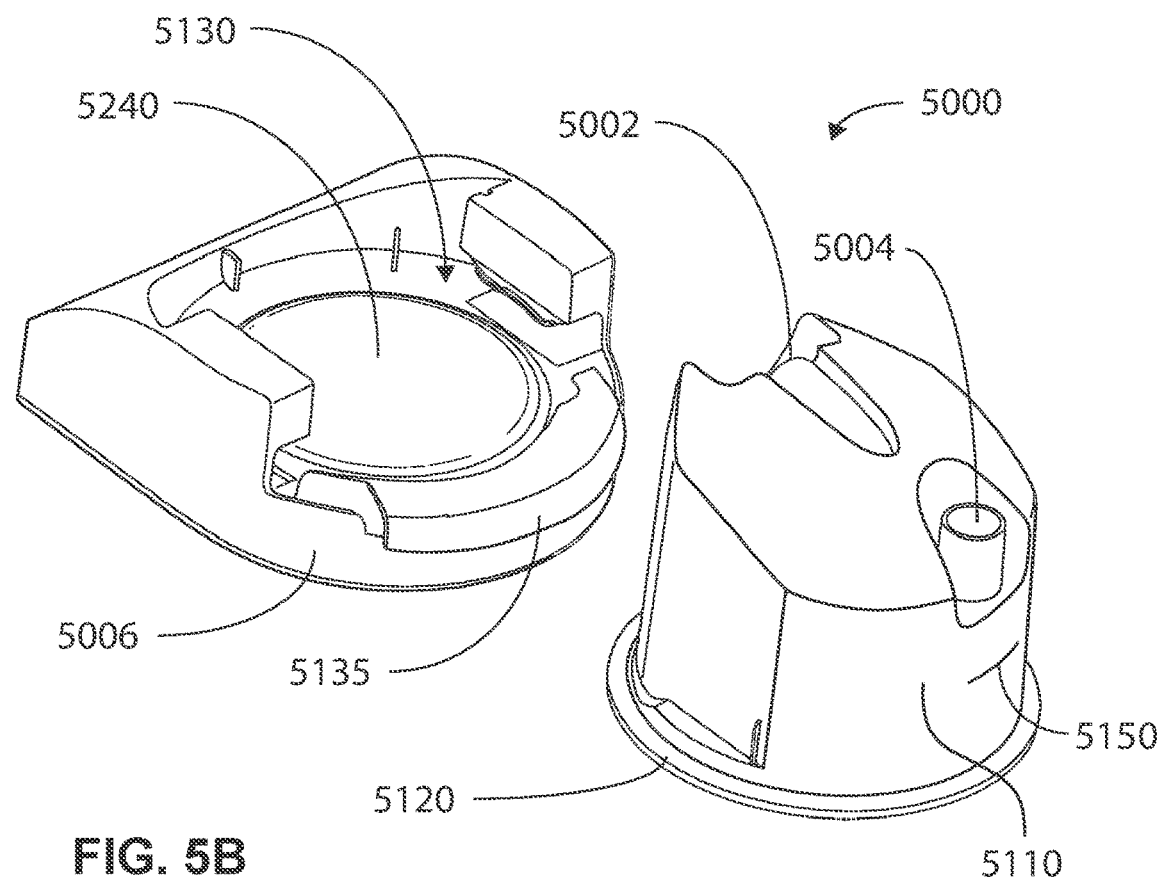

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
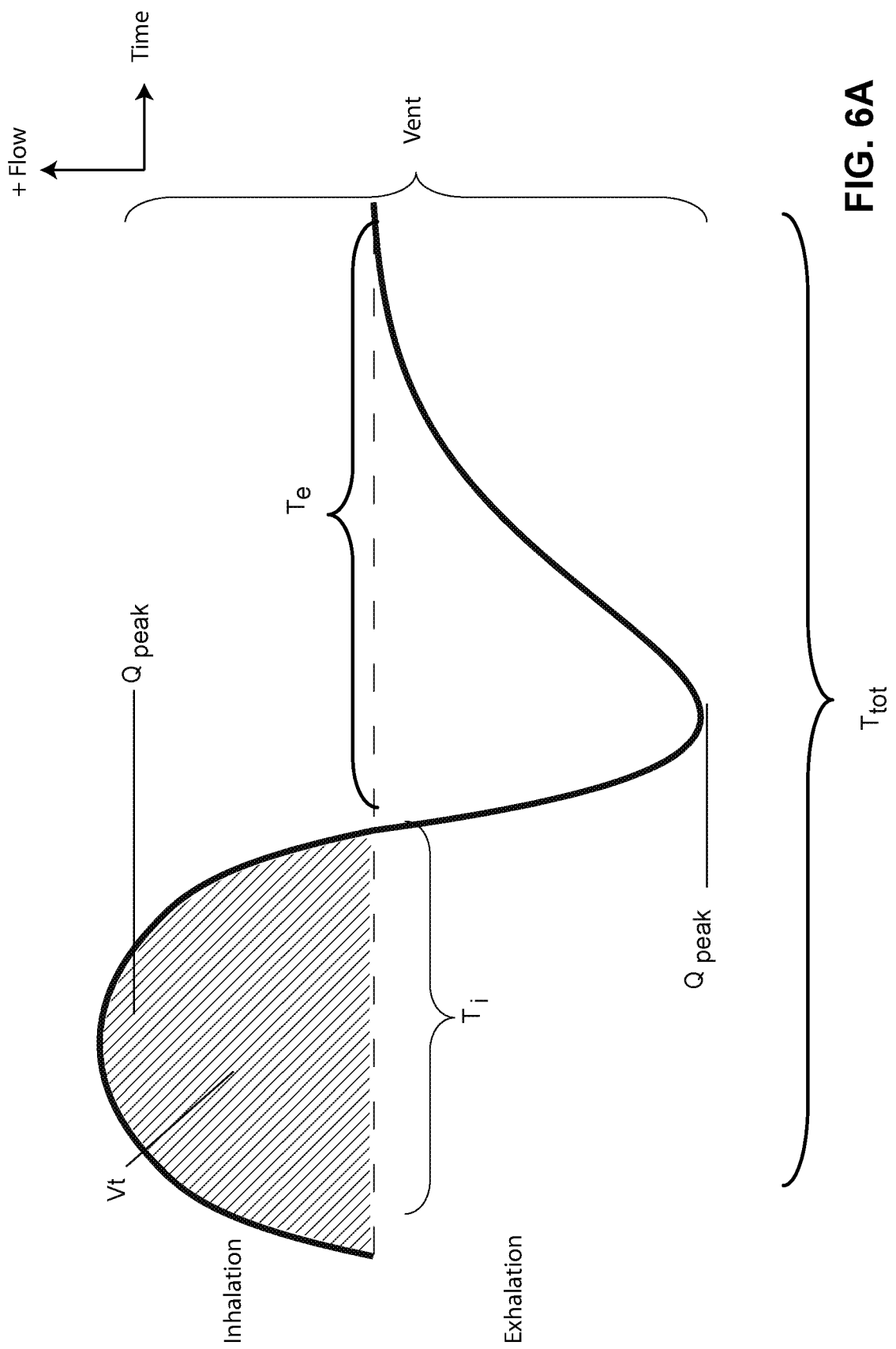

FIG. 6A shows a model typical breath waveform of a person while sleeping.

4.7 Screening, Diagnosis and Monitoring Systems

Figure 7A:
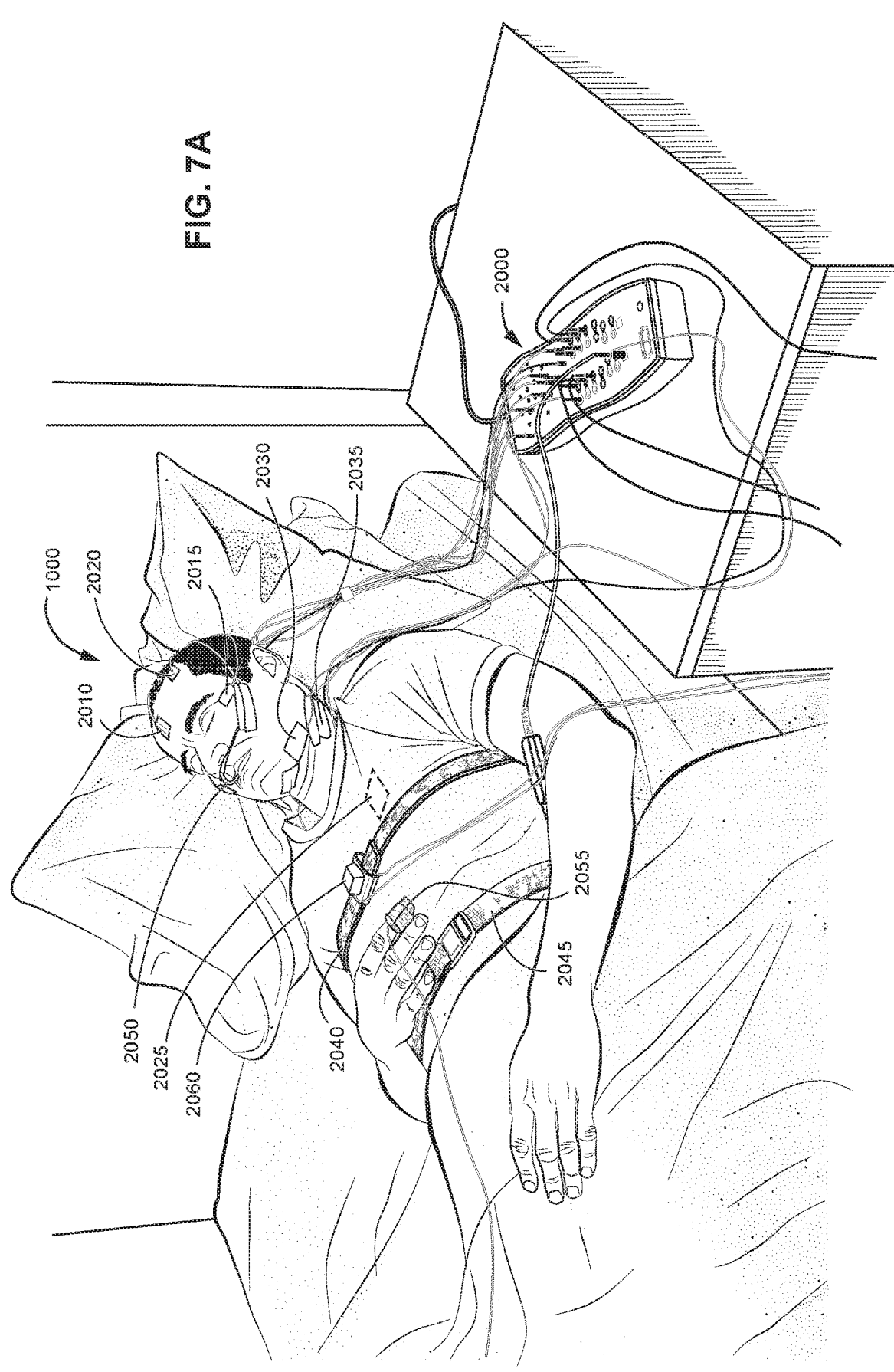

FIG. 7A shows a patient undergoing polysomnography (PSG). The patient is sleeping in a supine sleeping position.

Figure 7B:
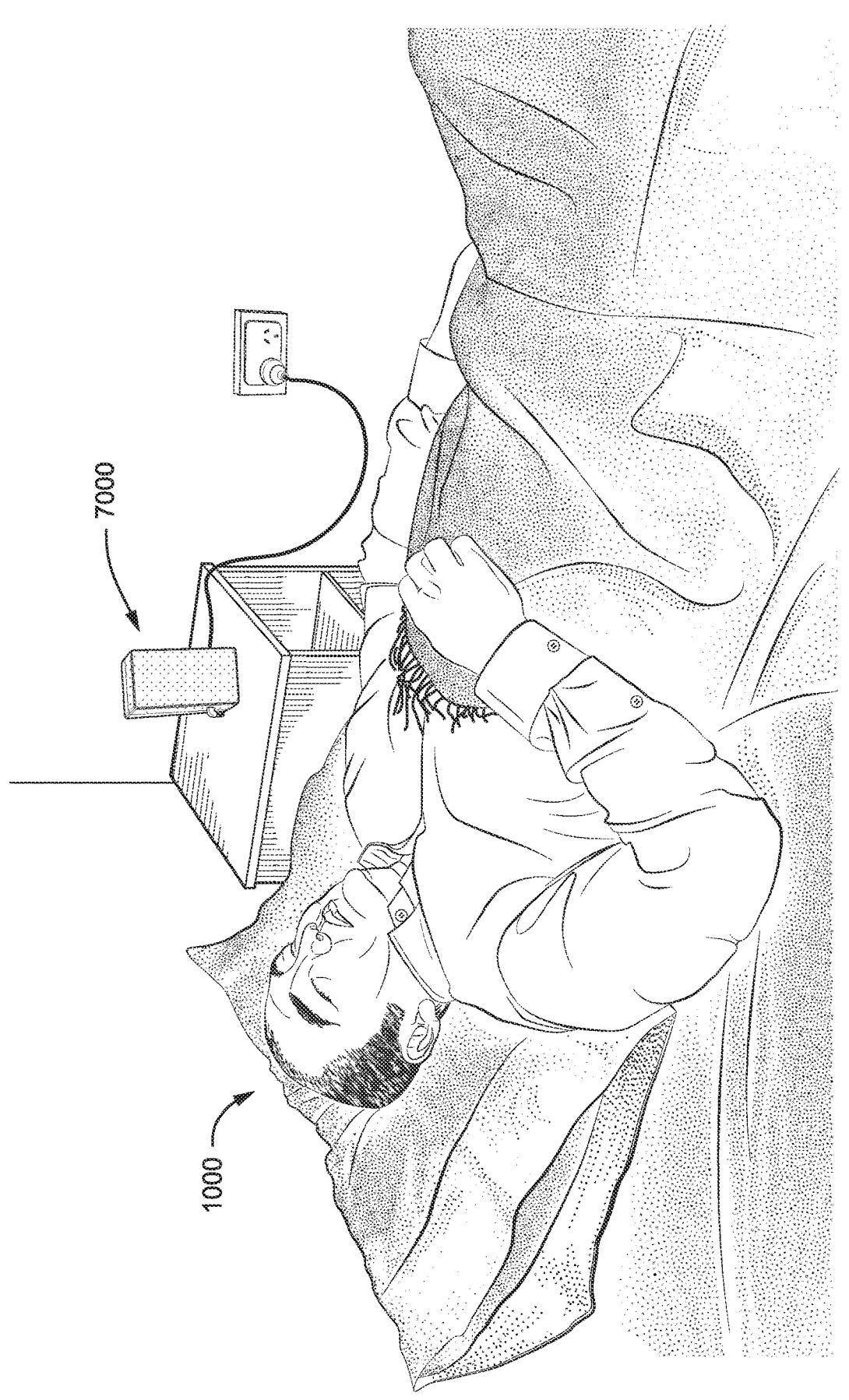

FIG. 7B shows a monitoring apparatus for monitoring the condition of a patient. The patient is sleeping in a supine sleeping position.

4.8 Particular Examples of the Present Technology

Figures 8A, 8B:
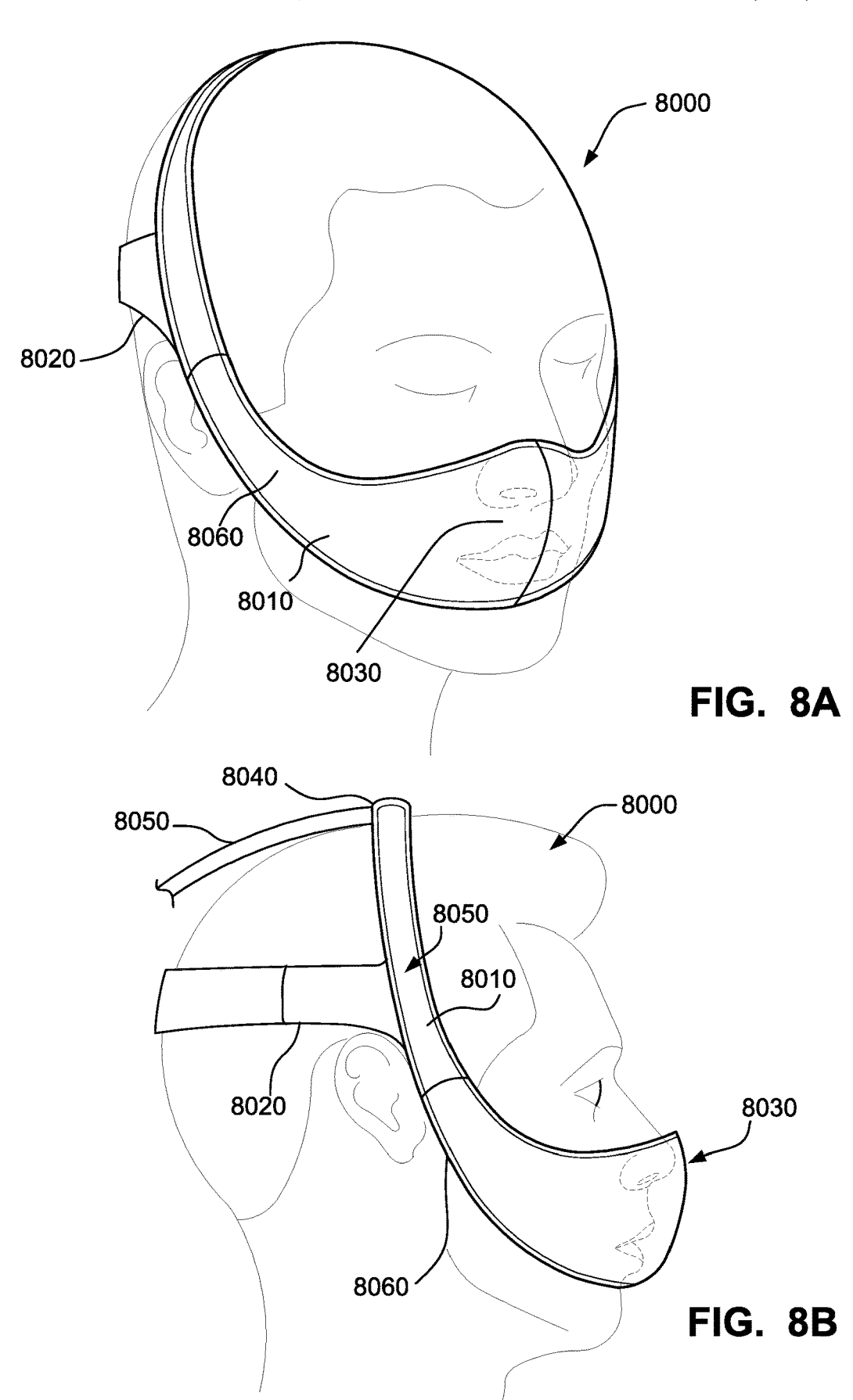

FIG. 8A is a front perspective view of a patient interface 8000 according to one example of the present technology while worn by a patient 1000.

FIG. 8B is a right side view of the patient interface 8000 shown in FIG. 8A.

FIG. 8C is a right side view of the patient interface 8000 shown in FIG. 8A.

FIG. 8D illustrates an example of part of a headgear tubing of the patient interface in a collapsed state.

FIG. 8E shows the headgear tubing of FIG. 8D in an inflated state.

Figure 8F:
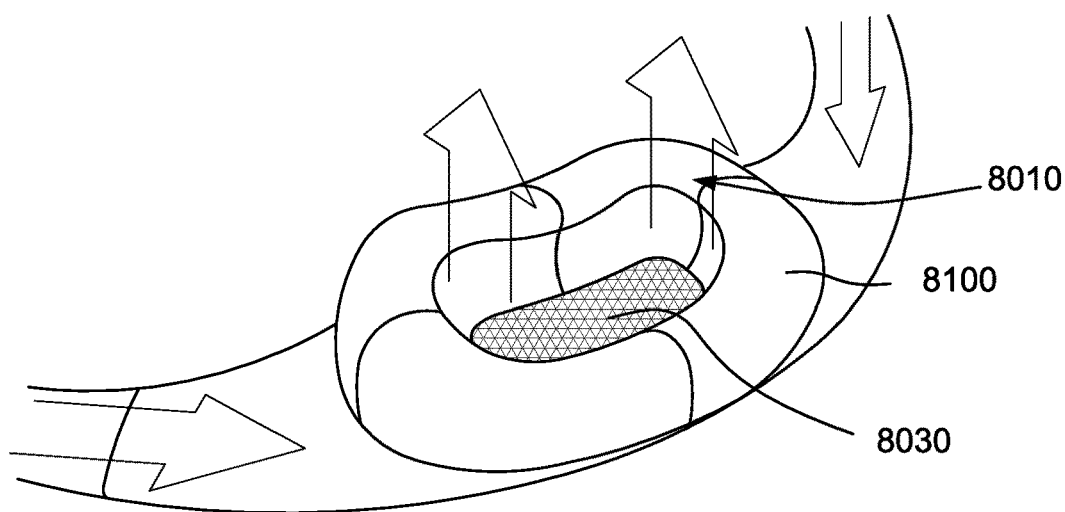

FIG. 8F is a schematic illustration of the flow of air from the headgear tubing towards and out of a plenum chamber of a patient interface.

Figure 9A:
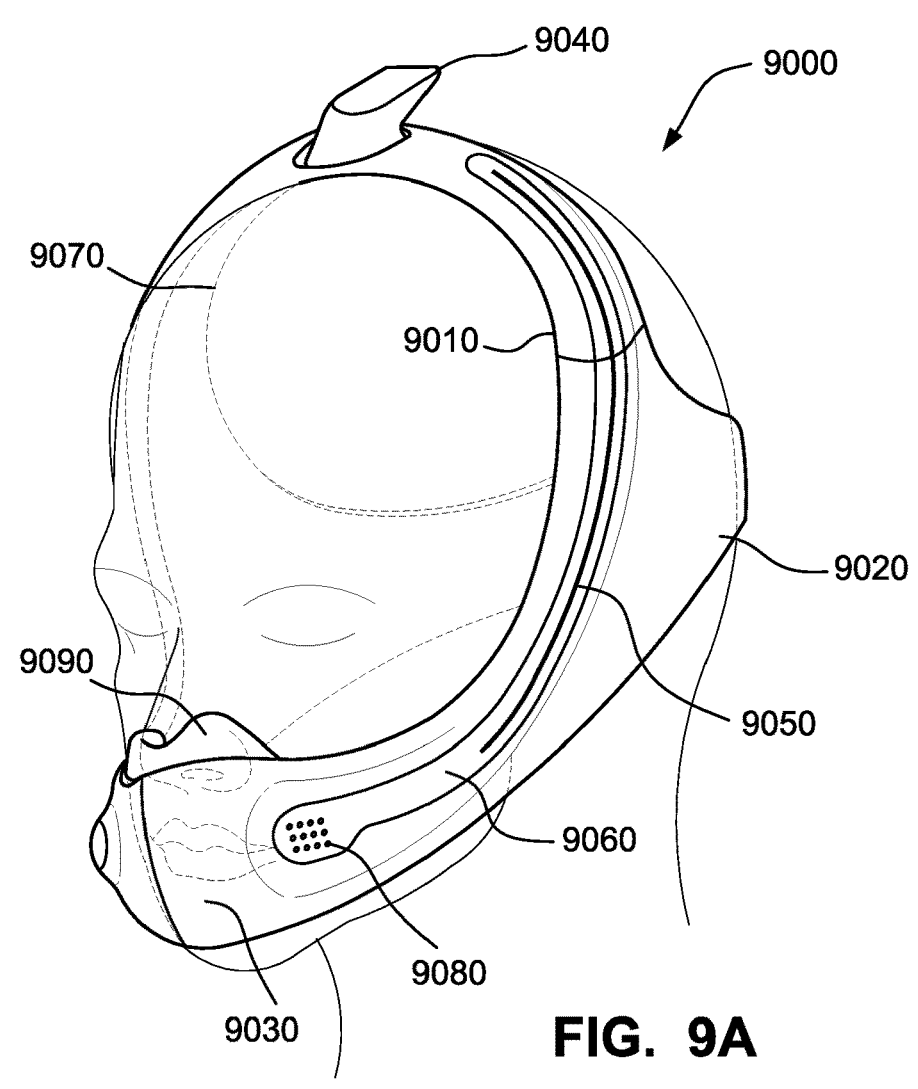

FIG. 9A is a front perspective view of a patient interface 9000 according to one example of the present technology while worn by a patient 1000.

FIG. 9B is a left side view of the patient interface shown in FIG. 9A.

FIG. 9C shows part of headgear tubing of the patient interface of FIG. 9A and FIG. 9B.

FIG. 9D is a rear perspective view of a seal-forming structure connected to headgear tubing of the patient interface of FIG. 9A.

FIG. 9E is an example of a plenum chamber fitted to a seal forming structure of a patient interface.

Figure 9F:
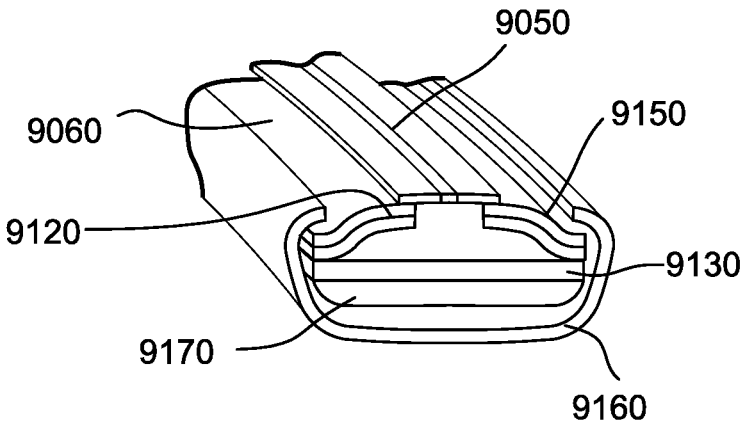

FIG. 9F is a perspective view showing a cross section through headgear tubing in a collapsed state.

Figure 9G:
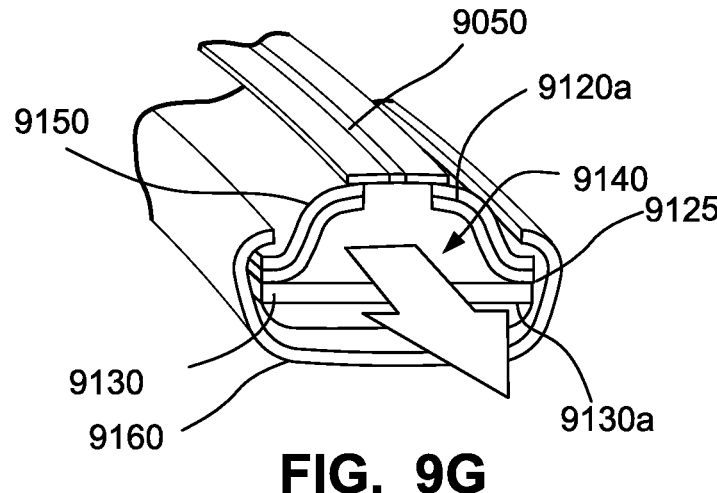

FIG. 9G shows the headgear tubing of FIG. 9F in an inflated state.

Figure 9H:
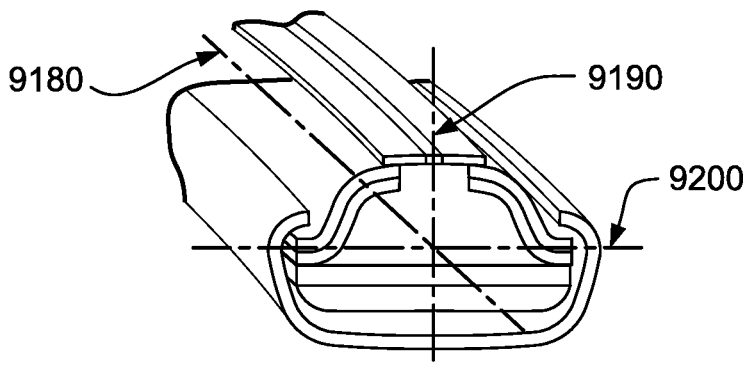

FIG. 9H is a further view of the headgear tubing of FIG. 9G, showing axes with reference to which physical properties of the headgear tubing may be defined.

FIG. 10A is a right side view of an example of headgear of a patient interface.

FIG. 10B illustrates an example of a fastening portion of headgear tubing of the patient interface of FIG. 10A in a closed state.

FIG. 10C illustrates an example of the fastening portion of the headgear tubing of FIG. 10B in an open state.

FIG. 11A is a front perspective view of another embodiment of a patient interface, in use by a patient.

FIG. 11B is a front view of the embodiment shown in FIG. 11A.

FIG. 11C is a close-in view of an anterior portion of the patient interface of FIG. 11A.

FIG. 11D is a top perspective view of a superior portion of the patient interface of FIG. 11A.

Figure 11E:
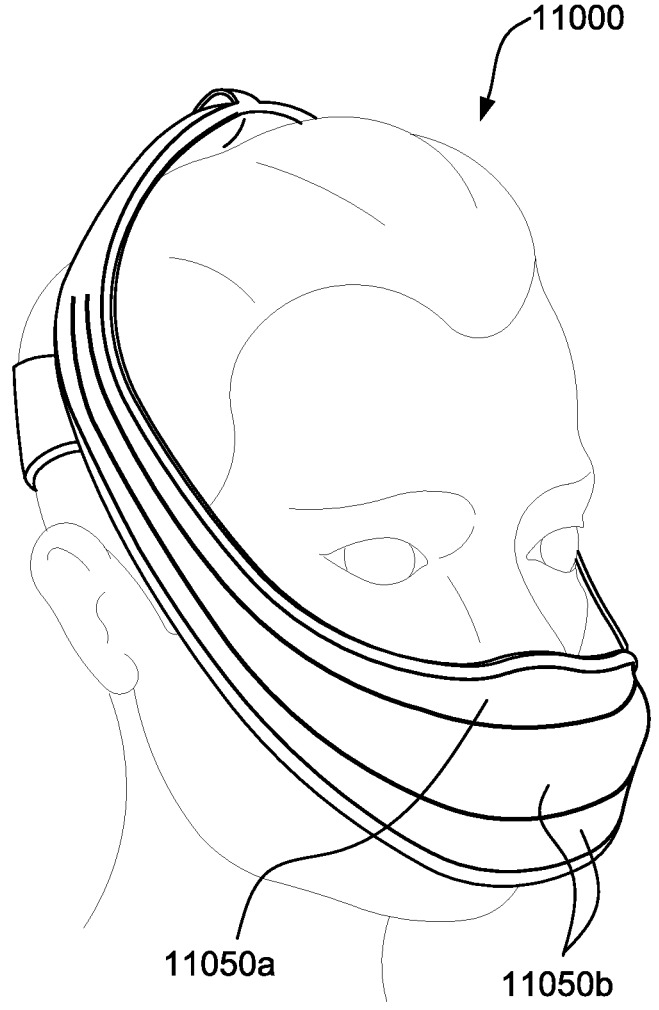

FIG. 11E is a front perspective view of another embodiment of a patient interface, in use by a patient.

Figure 12:
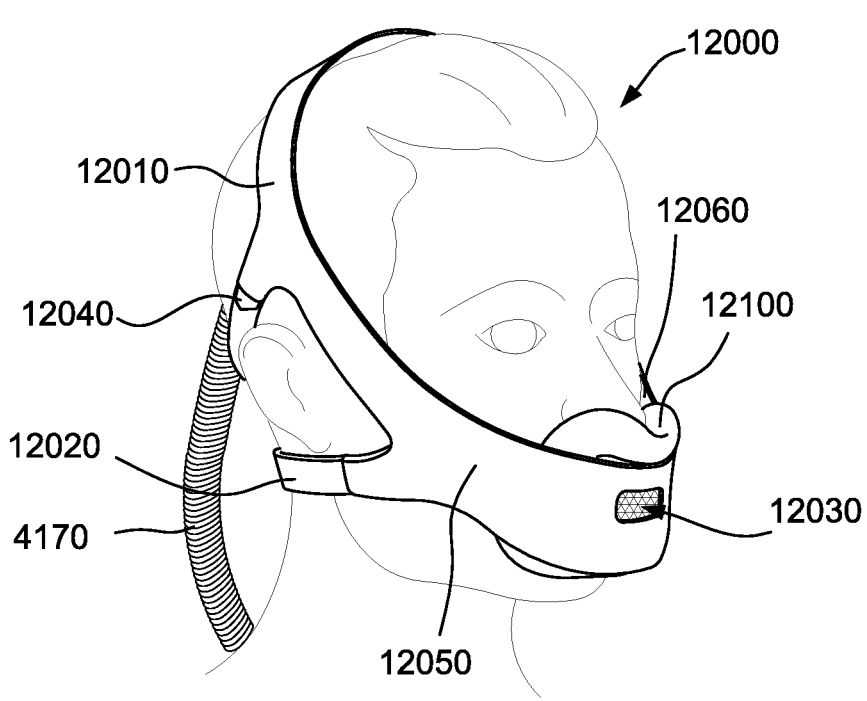

FIG. 12 is a front perspective view of another embodiment of a patient interface.

Figure 13A:
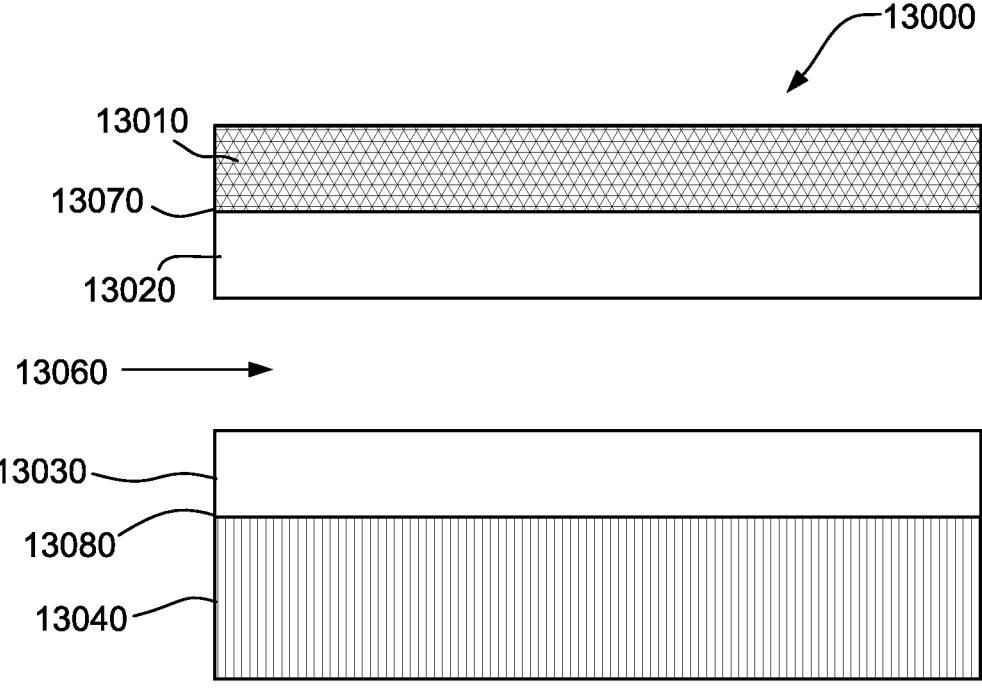

FIG. 13A is a schematic cross-section through an embodiment of headgear tubing.

Figure 13B:
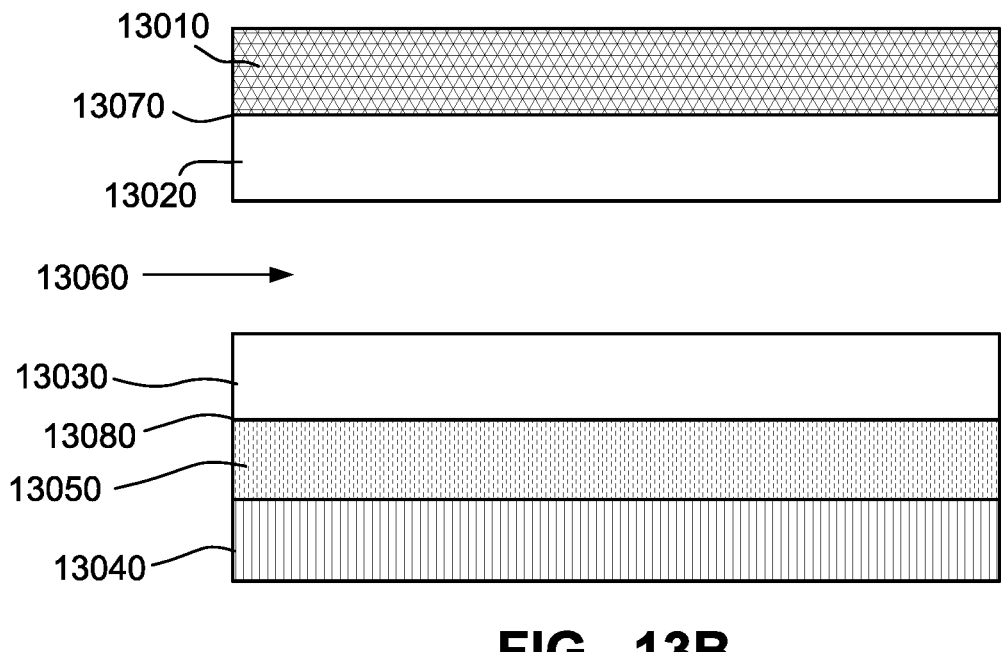

FIG. 13B is a schematic cross-section through another embodiment of headgear tubing.

Figure 13C:
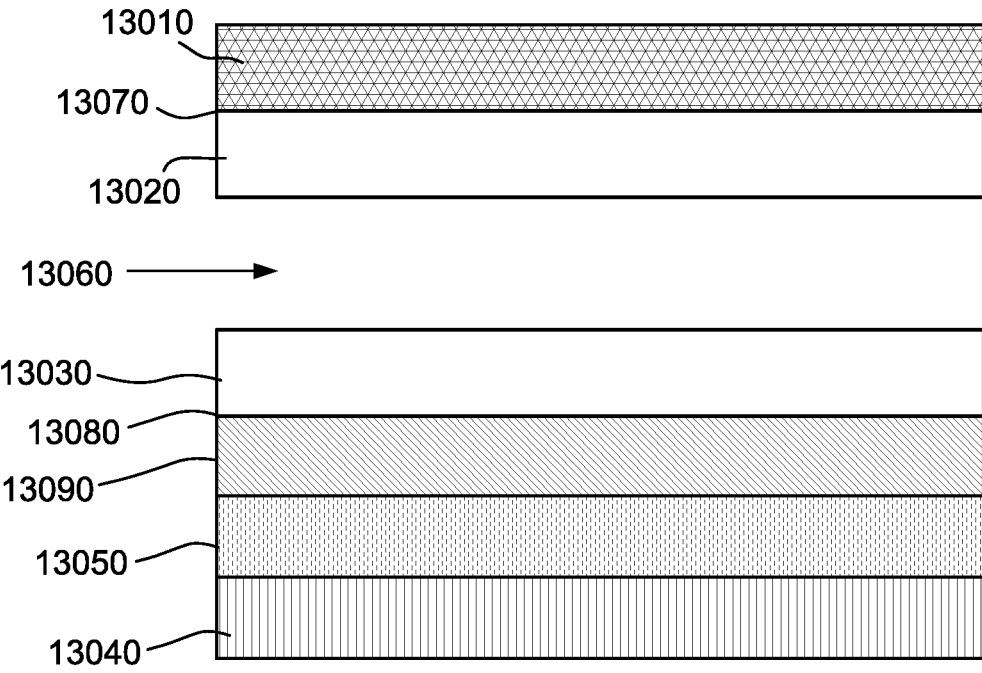

FIG. 13C is a schematic cross-section through a further embodiment of headgear tubing.

Figure 14A:
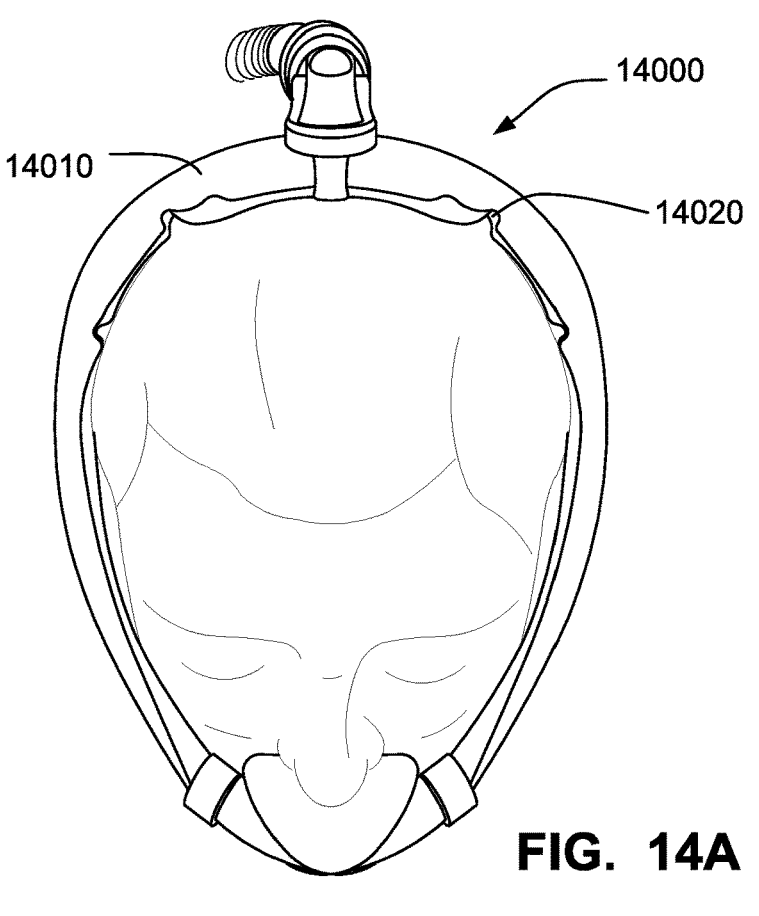

FIG. 14A is a front view of an embodiment of a headgear without a rigidiser.

Figure 14B:
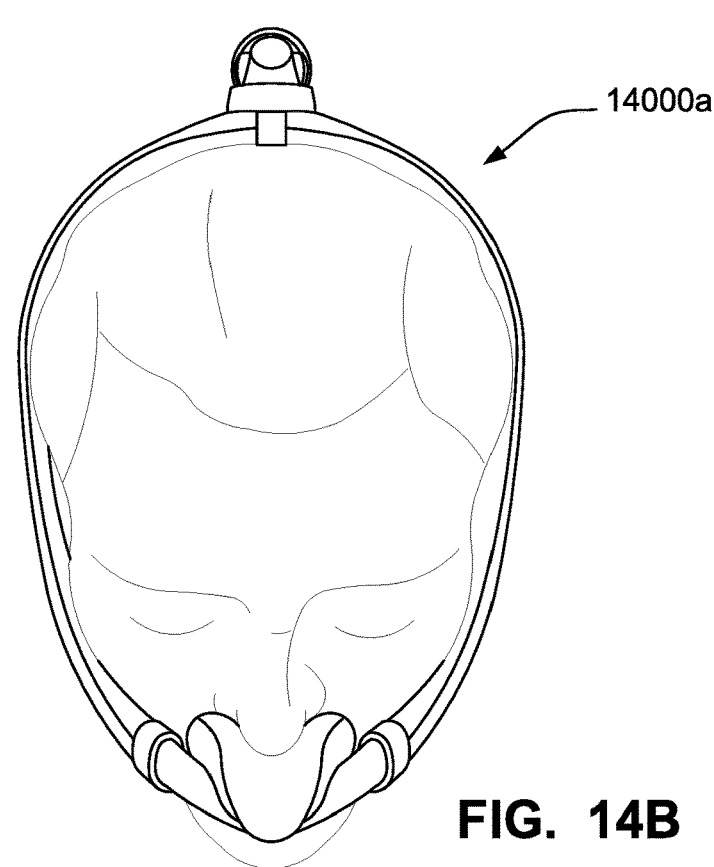

FIG. 14B is a front view of an embodiment of a headgear with a rigidiser.

Figure 15A:
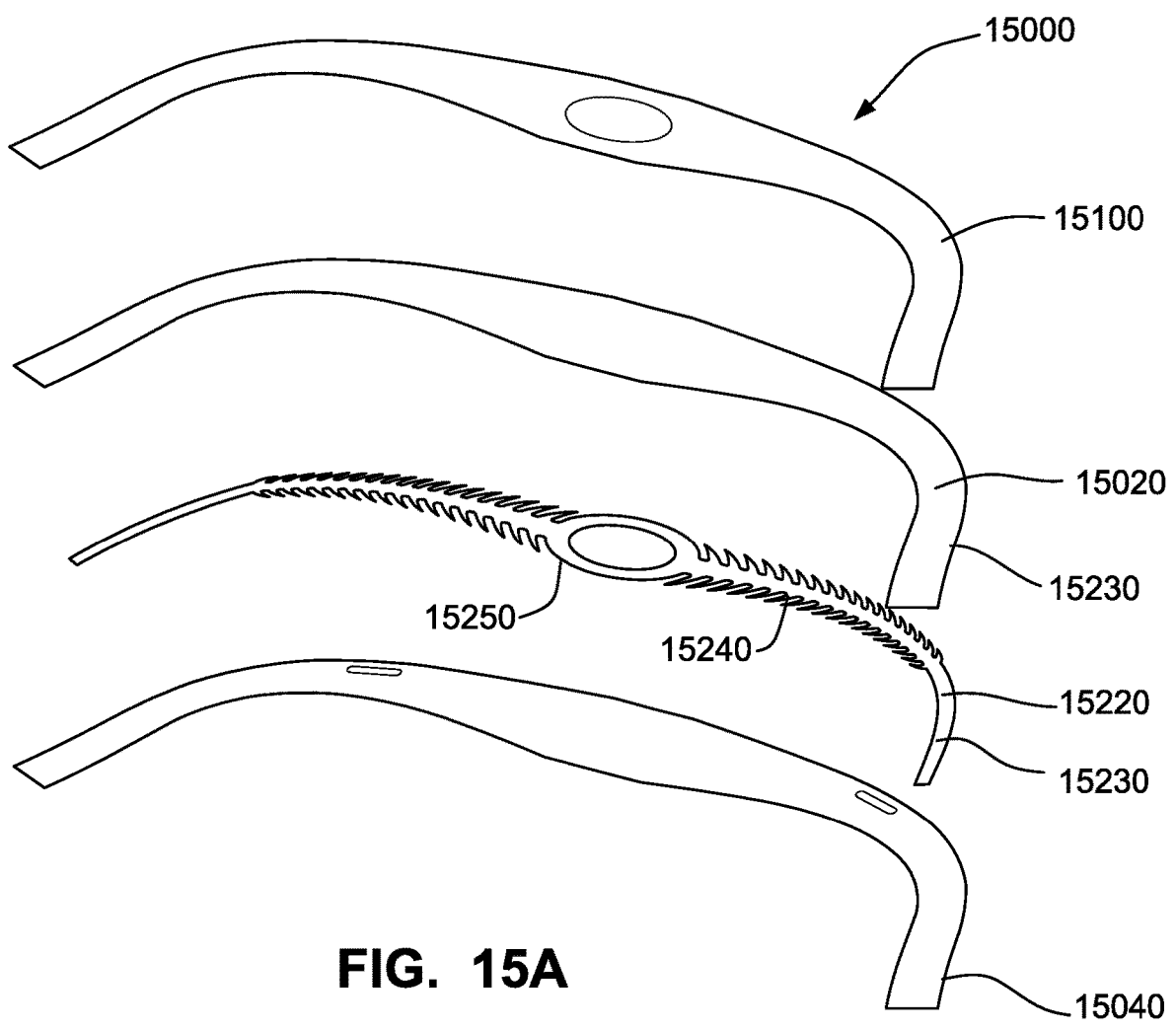

FIG. 15A is a exploded view of an embodiment of a headgear.

Figure 15B:
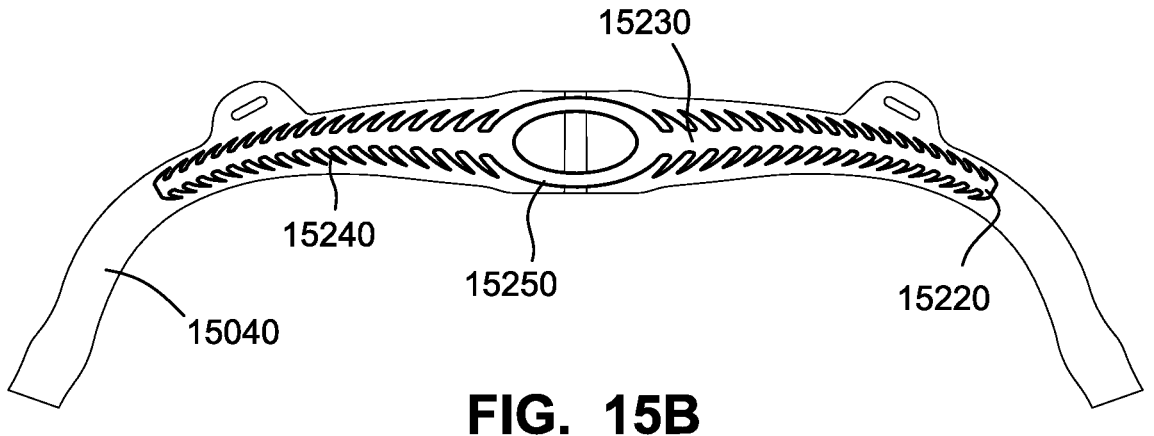

FIG. 15B shows an example of a rigidiser on a double walled film of a headgear tubing.

Figure 15C:
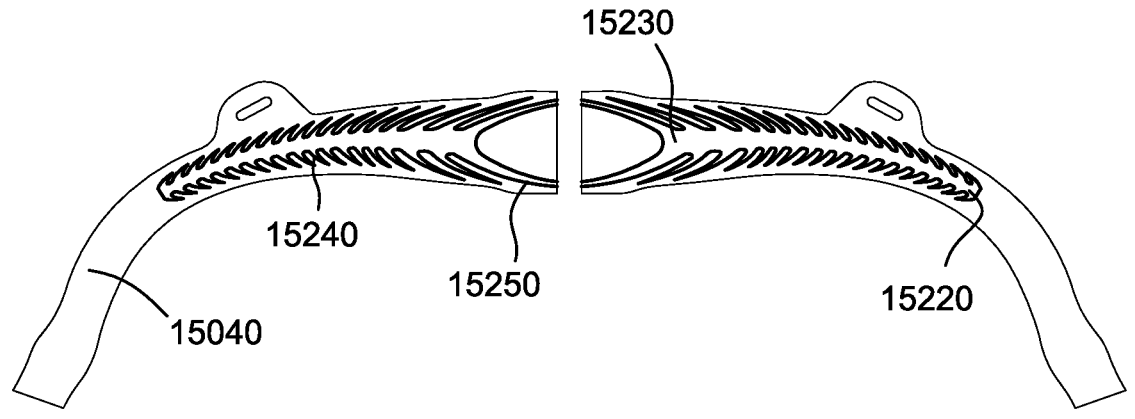

FIG. 15C shows another example of a rigidiser on a double walled film of a headgear tubing.

Figure 16A:
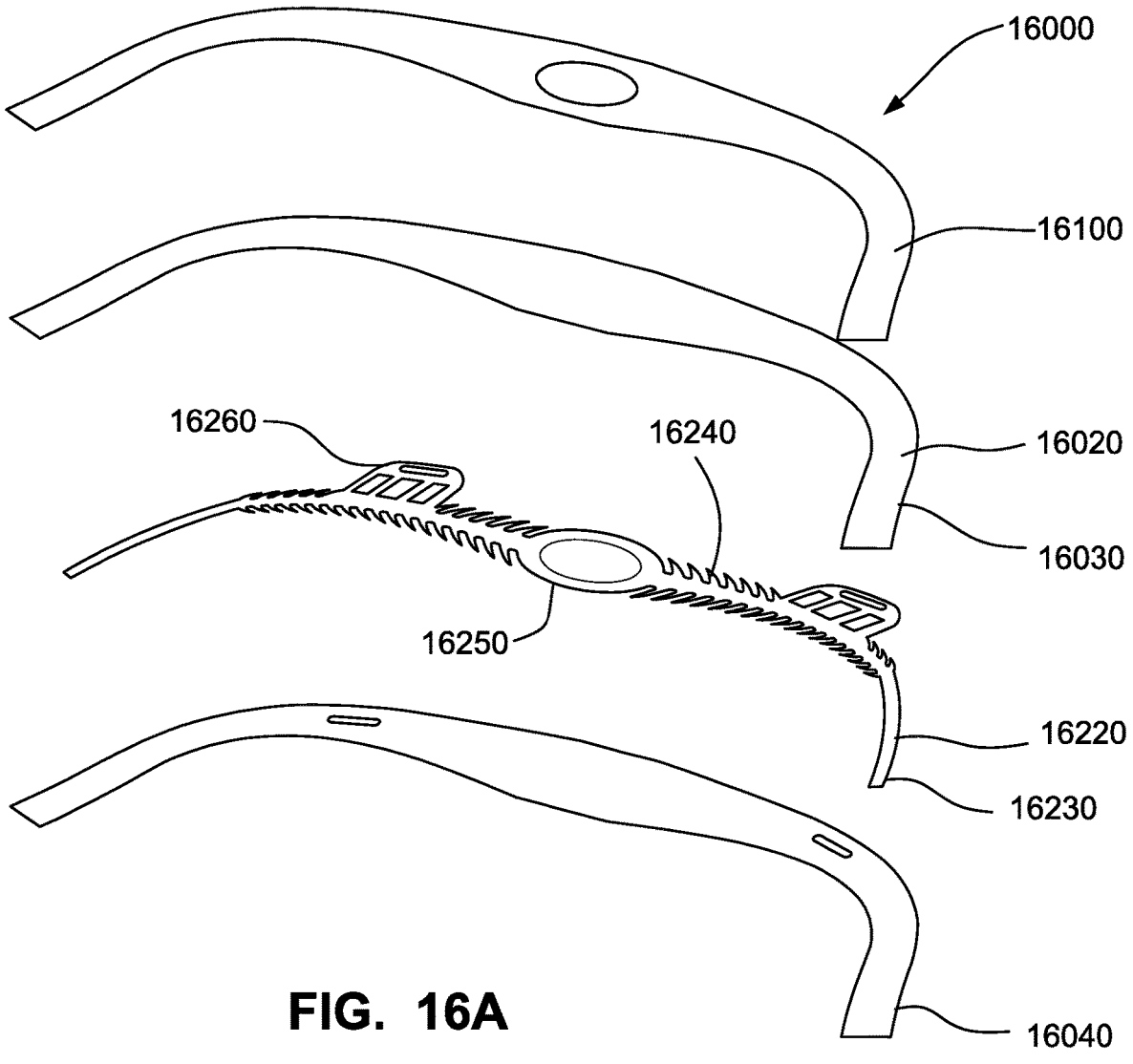

FIG. 16A is an exploded view of another embodiment of a headgear.

Figure 16B:
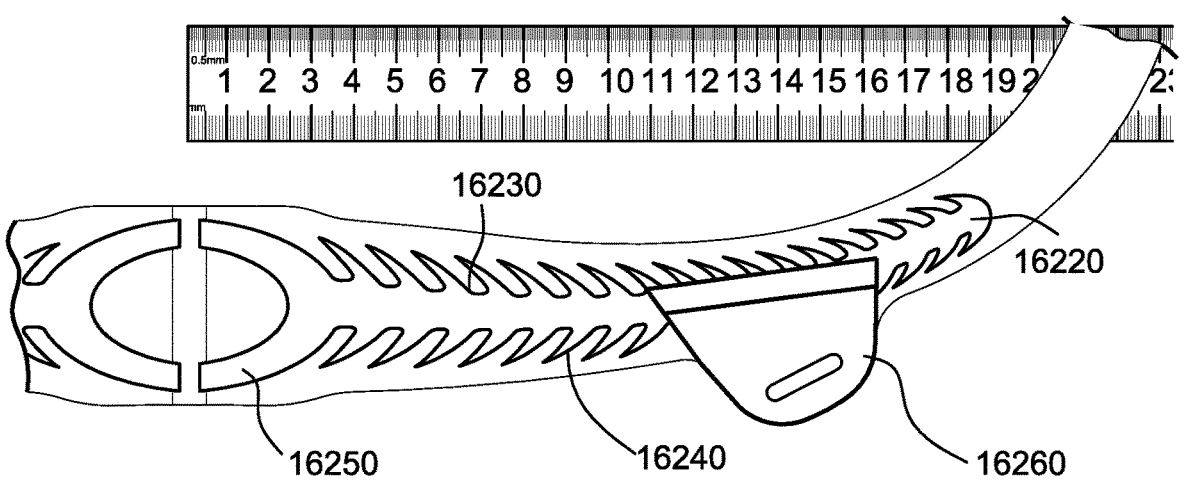

FIG. 16B shows an example of a rigidiser on a fabric layer.

Figure 16C:
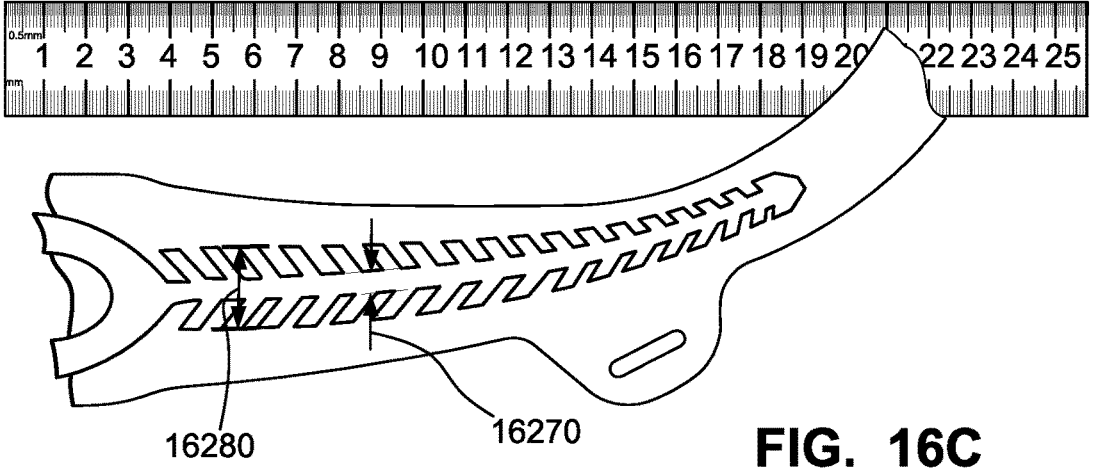

FIG. 16C shows another example of a rigidiser on a fabric layer.

Figure 17:
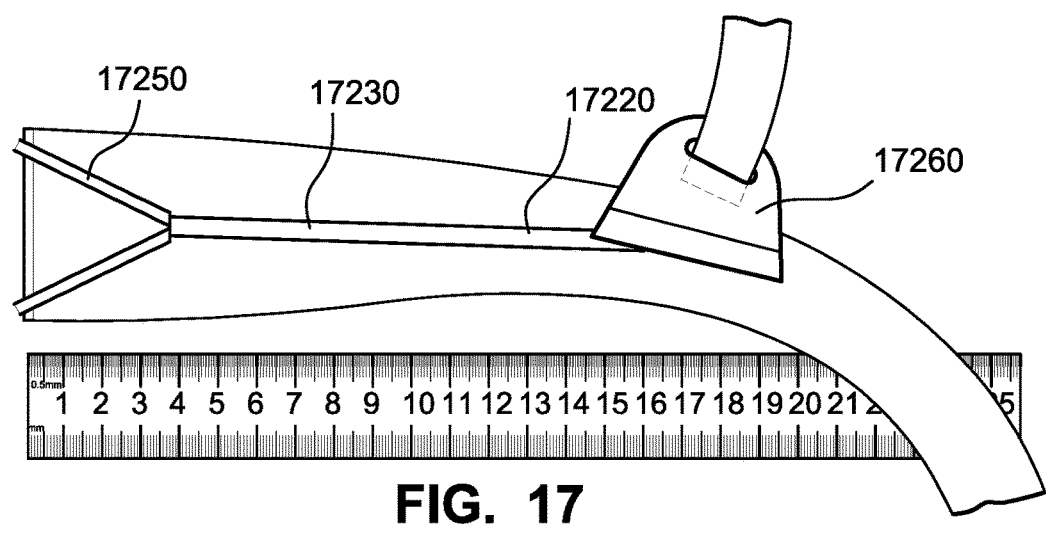

FIG. 17 shows a further example of a rigidiser on a fabric layer.

FIG. 18A shows another example of a rigidiser on a double walled film.

FIG. 18B shows another example of a rigidiser.

FIG. 18C is a top view of an embodiment of a headgear with a rigidiser.

Figures 1, 2, 19, 20A, 20B, 20C, 20D:
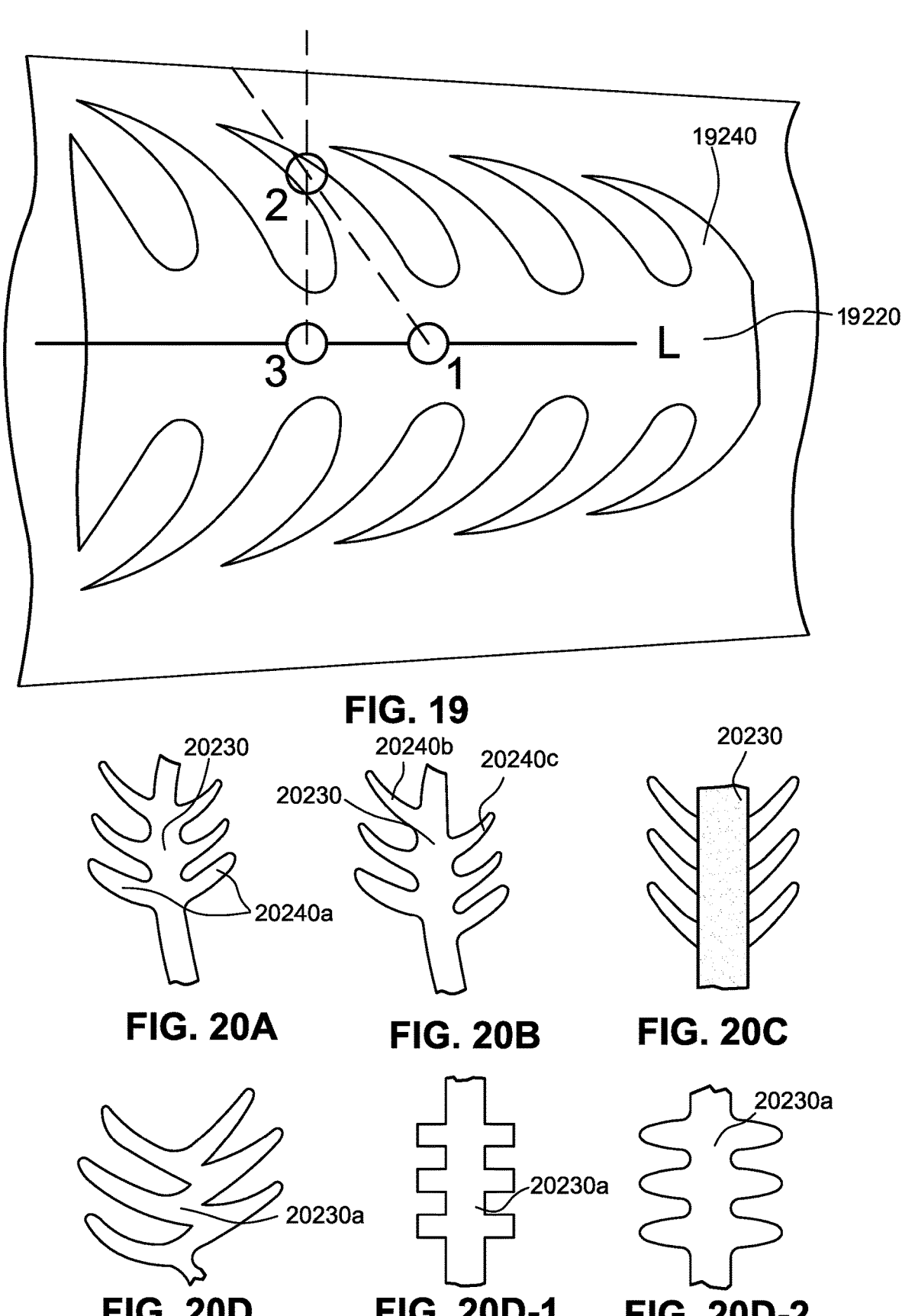

FIG. 19 is an enlarged view of the rigidiser of FIG. 16B showing details of a spine structure and protrusions of the rigidiser.

FIG. 20A shows a further example of a rigidiser with opposing protrusions.

FIG. 20B shows a further example of a rigidiser with alternating protrusions.

FIG. 20C shows a further example of a rigidiser formed from a rigid material and an elastomeric material.

FIG. 20D shows a further example of a rigidiser with a stretchable portion formed in a first configuration.

FIG. 20D-1 shows a further example of a rigidiser with a stretchable portion formed in a second configuration.

FIG. 20D-2 shows a further example of a rigidiser with a stretchable portion formed in a third configuration.

Figure 21:
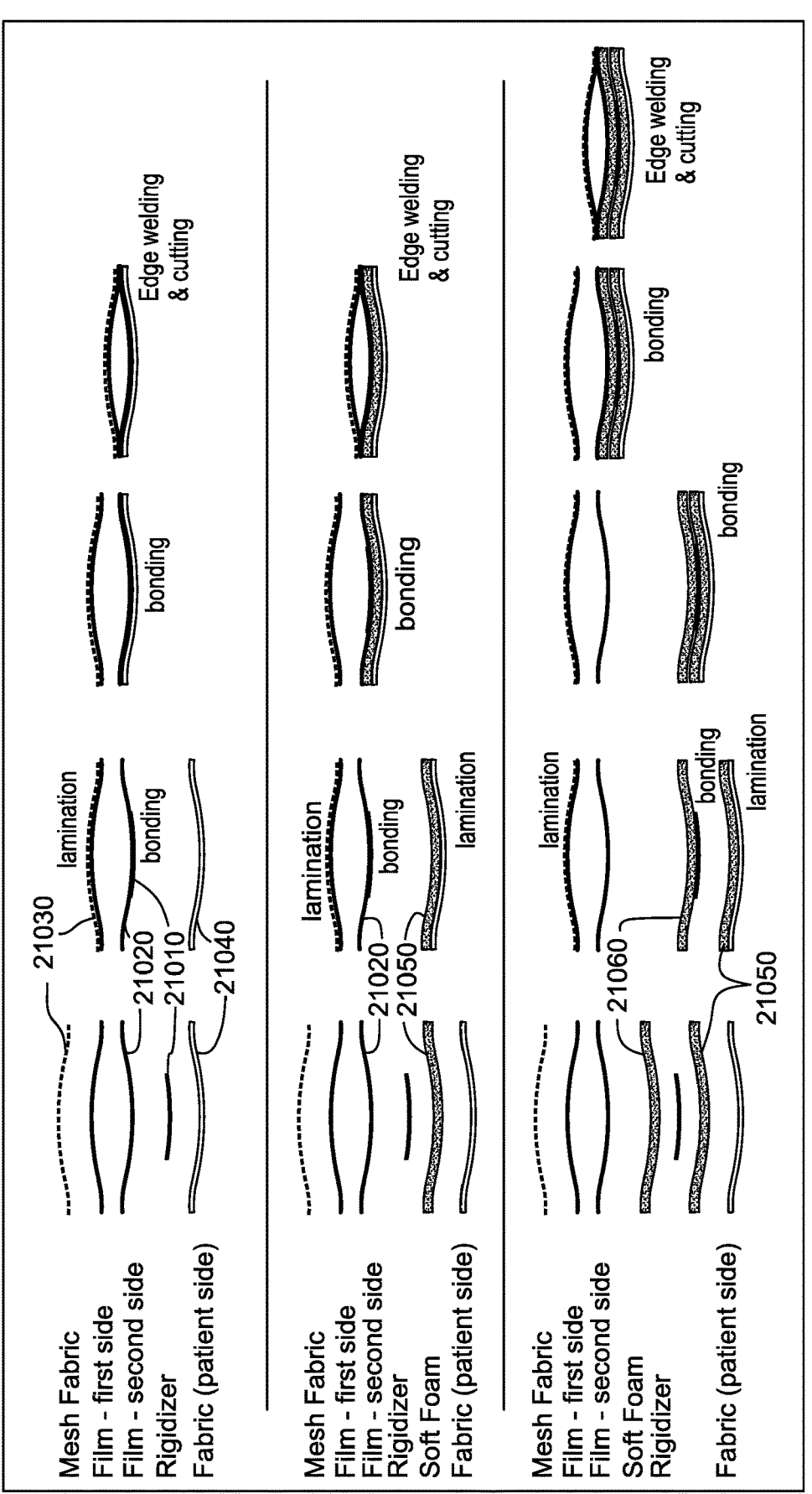

FIG. 21 shows examples of where the rigidiser is positioned within the headgear tubing.

Figure 22:
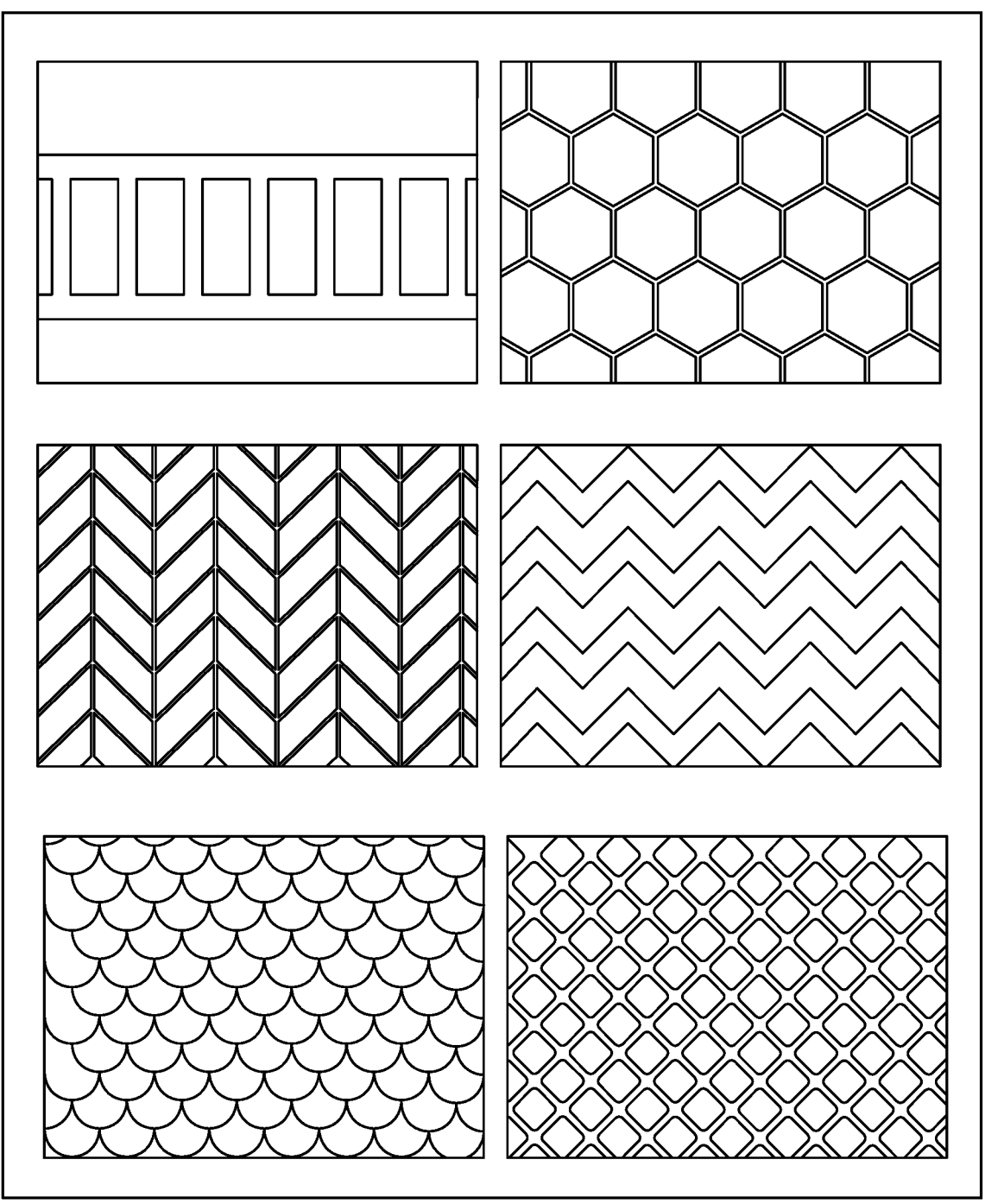

FIG. 22 shows examples of the air pathway patterns which is formable in the inflatable bladder and/or sealforming structure.

Figure 23A:
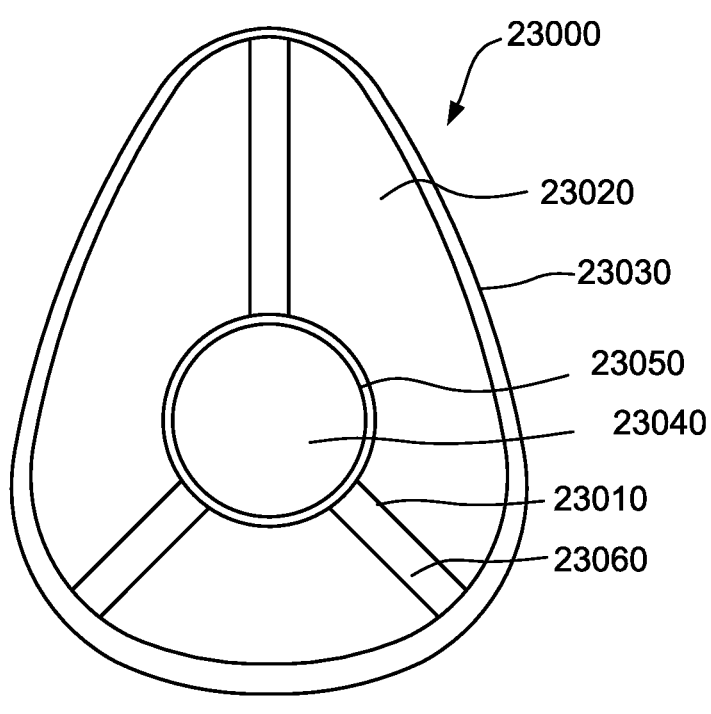

FIG. 23A shows a front view of an embodiment of a plenum chamber with ribs.

Figure 23B:
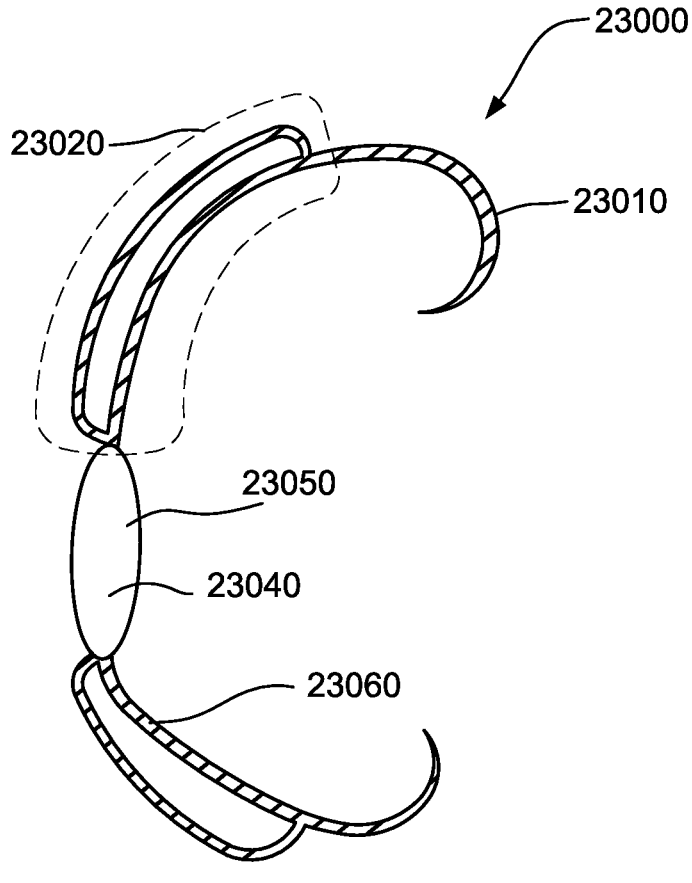

FIG. 23B shows a side view of an embodiment of a plenum chamber with ribs.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 THERAPY

In one form, the present technology comprises a method for treating a respiratory disorder comprising applying positive pressure to the entrance of the airways of a patient 1000.

In one form, the present technology comprises a method of screening a respiratory disorder comprising applying positive pressure to the entrance of the airways of a patient 1000. In one form, the present technology comprises a method of diagnosing a respiratory disorder comprising applying positive pressure to the entrance of the airways of a patient 1000. In one form, the present technology comprises a method of monitoring a respiratory disorder comprising applying positive pressure to the entrance of the airways of a patient 1000. In one form, the present technology comprises a method of ameliorating a respiratory disorder comprising applying positive pressure to the entrance of the airways of a patient 1000. In one form, the present technology comprises a method of preventing a respiratory disorder comprising applying positive pressure to the entrance of the airways of a patient 1000.

The applied positive pressure can be provided via a high pressure source and/or an oxygen source through to the headgear and/or the patient interface as disclosed herein.

In one form, the present technology provides an apparatus used in the screening of a respiratory disorder. In one form, the present technology provides an apparatus used in the diagnosis of a respiratory disorder. In one form, the present technology provides an apparatus used in the monitoring of a respiratory disorder. In one form, the present technology provides an apparatus used in the amelioration of a respiratory disorder. In one form, the present technology provides an apparatus used in the treatment of a respiratory disorder. In one form, the present technology provides an apparatus used in the prevention of a respiratory disorder.

The apparatus can be a medical device which can comprise the headgear and/or the patient interface as disclosed herein.

Examples of the respiratory disorder include, but are not limited to, Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

In certain examples of the present technology, a supply of air at positive pressure is provided to the nasal passages of the patient via one or both nares.

In certain examples of the present technology, mouth breathing is limited, restricted or prevented.

5.2 RESPIRATORY THERAPY SYSTEMS

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000 or 3800.

5.3 PATIENT INTERFACE

A non-invasive patient interface 3000 in accordance with one aspect of the present technology comprises the following functional aspects: a seal-forming structure 3100, and a headgear as disclosed herein. The headgear comprises a tensioning structure 3300. The headgear is suitable for delivering of a supply of pressurised breathable gas to an entrance of a patient's airways.

Other embodiments of the patient interface of the present technology are also shown in FIGS. 8, 9, 10, 11, 12 and 14. Using FIGS. 8A and 8B as an example, the patient interface 8000 comprises a headgear 8010 and a seal-forming structure (hidden). The headgear 8010 comprises a headgear tubing 8060 and a tensioning structure 8020. The headgear tubing 8060 provides a flow of pressurised air from an inlet 8040 of the headgear to an outlet 8030 of the headgear. The inlet 8040 is connected to an air delivery tube 4170 in order for pressurised air to flow into the headgear tubing 8060. The outlet 8030 is positionable adjacent to a patient's nares and/or mouth when in use. The flow of pressurised air is shown by the arrows in FIG. 8B. The pressurised air is directed out from the outlet 8030 via air flow 8110. The tensioning structure 8020 can be connected to the headgear tubing 8060 at any position as long as it is able to provide a tensioning force for securing the headgear to a patient's head. The tensioning structure 8020 can also be integral to the headgear tubing 8060. As shown in this embodiment, the tensioning structure 8020 is connected at a proximal position along the headgear tubing 8060. In this embodiment, the tensioning structure 8020 is positioned such that when in use, it passes superior to an otobasion superior of the patient's head (above the ears).

FIG. 8B shows the air inlet 8040 positioned over a superior region of a patient's head when in use. The superior region refers to the cranial region of the head and which is proximal to the brain. Alternatively, the air inlet 8040 can be positioned any where along the length of the headgear tubing 8060. For example, the air inlet 8040 can be positioned on a lateral side of the patient's head.

FIG. 8C shows a right side view of the headgear tubing 8060. The inner layer 8070 which is in contact with the patient's head when in use is exposed. The inner layer 8070 can be a textile for providing comfort to the patient. As shown, the outer layer may also be constructed from a fabric layer so that the entire headgear tubing 8060 is constructed from the layer 8070. Although in other examples, only the The embodiment illustrated in FIG. 9A is a patient interface 9000 comprising a headgear 9010, a plenum chamber 9110 (hidden) and a seal-forming structure 9090. The plenum chamber 9110 is enveloped within the headgear adjacent to the outlet 9030. In this embodiment, the plenum chamber 9110 is generally not visible after the patient interface is donned by the patient. The plenum chamber 9110 is pressurisable to a therapeutic pressure of at least 6 cmH$_2$O above ambient air pressure. As shown in FIG. 9E, said plenum chamber including a plenum chamber inlet port 9112 sized and structured to receive a flow of air at the therapeutic pressure for breathing by a patient. The plenum chamber inlet port 9112 can be connected to an end of the headgear tubing. The seal-forming structure 9090 is positioned at an inner surface 9070 of the headgear adjacent to the outlet 9030, and is constructed and arranged to form a seal with a region of the patient's face surrounding an entrance to the patient's airways, said seal-forming structure 9090 having a hole therein such that the flow of air at said therapeutic pressure is delivered to at least an entrance to the patient's nares, the seal-forming structure constructed and arranged to maintain said therapeutic pressure in the plenum chamber 9110 throughout the patient's respiratory cycle in use. The patient interface is configured to allow the patient to breathe from ambient through their mouth in the absence of a flow of pressurised air through the plenum chamber inlet port. Alternatively, the patient interface can be configured to leave the patient's mouth uncovered.

As mentioned, the patient interface 9000 can further comprise a plenum chamber inlet port 9112 to allow a continuous flow of pressurised air from an end of the headgear tubing into the plenum chamber 9110. A patient can thus, via at least the nares, breathe in the pressurised air within the plenum chamber 9110. The plenum chamber can be designed to be of any size or shape, and in some examples, can be encased together with the headgear tubing by a fabric (also referred to herein as a textile) or other material.

The air inlet 9040 is laterally displaced above the headgear tubing 9060. The air inlet 9040 is further provided with a casing such that the connection between an air pressure tube and the air inlet is protected from being compressed when in use by the patient. The tensioning structure 9020 widens at one end to integrally connect with substantially the whole length of the headgear tubing 9060. The tensioning structure when formed in this matter, substantially covers the ears of the patient and provides a muffler function against noise disturbance.

Another embodiment of the patient interface 10000 is shown in FIG. 10A to 10C. The patient interface 10000 comprises a headgear 10010. The tensioning structure 10030 is positioned at a distal end position of the headgear tubing, adjacent to and in line with the outlet 10050. Additionally, a retention structure 10040 can be present for providing additional tensioning force in the form of additional support and stabilisation. The retention structure 10040 can connect substantially to the whole length of the headgear tubing 10010, and to a further position along the headgear tubing which is remote from the tensioning structure 10030. The retention structure 10040 can be integral to the headgear tubing and the tensioning structure 10040 such that it substantially cover the otobasion region of the patient's head (including the ears).

FIGS. 11A and 11B illustrates another embodiment of the patient interface 11000. The patient interface 11000 comprises a headgear 11010 and a seal-forming structure 11100. Similar to FIG. 8, the headgear 11010 comprises a tensioning structure 11020 which is positioned such that when in use, it passes superior to an otobasion superior of the patient's head (above the ears).

FIG. 12 illustrates another embodiment of the patient interface 12000. The patient interface 12000 comprises a headgear 12010 and a seal-forming structure 12100. The orifice 12030 is also shown, from which a plenum chamber (not shown) can be attached. When attached, the plenum chamber is fluidly connected to the outlet but sits externally to the headgear. An air delivery tubing 4170 is connectable to an inlet (hidden) of the headgear at one end, the other end of the tubing can be connected to a high pressure air source and/or an oxygen source. The tensioning structure 12020 and retention structure 12040 are connected and integral to the headgear tubing such that it substantially covers the otobasion region of the patient's head (excluding the ears).

In a use configuration (or when in use), the patient interface forms a web covering the patient's head or face. The conduit in the headgear tubing of the headgear is expanded or inflated due to the passage of pressurised air from the air inlet. The headgear tubing when filled with air takes on a three-dimensional configuration which substantially adopts the contours of the patient's head. Air from the inlet passes through the headgear tubing and out from the outlet into a patient's nares and/or mouth. In a collapsed configuration, the headgear tubing is deflated or substantially emptied of air. In this configuration, the headgear is elastically deformable and can be rolled and/or folded for packing/storage.

Another form of the non-invasive patient interface 3000 comprises a seal-forming structure 3100, a plenum chamber 3200, a tensioning structure 3300, a vent 3400, one form of connection port 3600 for connection to air circuit 4170, and a forehead support 3700. In use the seal-forming structure 3100 is arranged to surround an entrance to the airways of the patient so as to maintain positive pressure at the entrance (s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the tensioning structure and the shape of a patient's face.

For example, the seal-forming structure can cover at least one of the nares of the patient, or can cover at least one of the nares and the mouth of the patient.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone. For example, FIG. 8F shows a seal-forming structure 8100 and FIG. 9A shows a seal-forming structure 9090, each of which can be formed from silicone. In other forms, the seal-forming structure is constructed from a foam material. For example, FIG. 11C shows a seal-forming structure 11100 constructed from a foam material. FIG. 12 also shows a patient interface comprising a headgear and a seal-forming structure 12100 constructed from a foam material. In still other examples, the seal-forming structure may be constructed from a textile material.

The seal-forming structure can be removable from the outlet of the headgear. This allows the patient to wash the seal-forming structure for maintaining hygiene, and to replace the seal-forming structure as and when it is required.

In certain forms of the present technology, a system is provided comprising more than one seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

The seal-forming structure can be integrated with the headgear at the outlet thereof. In this regard, the seal-forming structure and the headgear is provided as one product. The seal-forming structure can be constructed and arranged to form a seal with a region of the patient's face surrounding an entrance to the patient's airway for delivery of air flow at a pressure of at least 6 cmH$_2$O above ambient air pressure. Alternatively, the seal-forming structure can be attachable to the headgear at the outlet thereof. A patient is thus able to separately purchase or replace these parts according to their needs.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the tensioning structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the tensioning structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

FIG. 9D shows an example of the seal-forming structure 9090 with sealing mechanism. The seal-forming structure 9090 comprises sealing flanges 9100 which extends around the perimeter of the seal-forming structure 9090.

The seal-forming structure can be an inflatable seal-forming structure. An inflating or ballooning seal type is a type of seal that, when in use, system pressure or air flow delivered to the seal-forming structure acts to urge an inwardly extending flange, skirt or other similar member onto a patient's face to form a substantial seal. Thus, an inflating or ballooning seal type is different from seal types that rely solely upon interface retention forces from headgear to push or deform a cushion against the patient's face with enough force to seal the cushion against the patient's facial features. To provide a suitable inflating or ballooning effect, the seal-forming structure can comprise a soft compliant seal member which is adapted to cover the patient's nares and/or mouth. The seal member can comprise a perimetric edge and a sealing flange that extends inwardly from the perimetric edge. Preferably, the sealing flange extends inwardly from all or substantially all of the perimetric edge. At least a part of the sealing flange forms a sealing portion which contacts the patient's face. The seal-forming structure is also adapted to be in fluid communication with the air inlet. In use, the seal-forming structure is flushed with air from the air inlet, the sealing portion rests against the face of the patient and, under an internal pressure of the inflating seal and a retention pressure of headgear, the sealing portion is pressed against the face of the patient to create an effective seal inward of the perimetric edge. The inflatable seal-forming structure acts to minimize the pressure on the patient's face and distribute pressure and reduce the likelihood of excessive localised pressure distributions.

The inflatable seal-forming structure can be curved in shape to match the contours of a patient's face and extends about the patient's nose, substantially wrapping the patient's nose. The seal-forming structure can extend completely over the side of the patient's nose and may also extend at least partially over the patient's cheeks.

Such inflatable seal-forming structures can be formed from silicone with a Shore A hardness of about 40. Other materials with similar properties may also be used.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the visual obtrusiveness of the patient interface, and help improve compliance with therapy.

FIG. 9E shows a plenum chamber 9110 which is attachable to the patient interface 9000. The plenum chamber 9110 is positionable adjacent to and in fluid communication with the outlet of the headgear. The plenum chamber 9110 can be made of a transparent or translucent material.

FIG. 12 shows an orifice 12030 from which a plenum chamber (not shown) can be attached. As is disclosed herein, the plenum chamber can comprise a vent for facilitating the expulsion of carbon dioxide and excess pressurised air.

The plenum chamber can be provided with an inflatable seal-forming structure as mentioned above. When silicone is used as the material for the inflatable seal-forming structure, the resultant silicone cushion tends to have less stability and the hard plastic frame structure of the plenum chamber is still in contact with the patients' cheeks. Further, as the hard plastic frame structure is relatively heavy, the seal can be easily disturbed. As an alternative, a plenum chamber with a frame structure that is soft, flexible and yet provide enough structural support can be used.

The plenum chamber 23000 can be provided with a frame 23010 and an inflatable bladder 23020 as shown in FIGS. 23A and 23B. The inflatable bladder 23020 can be adapted to connect with the inflatable seal-forming structure 23030, or alternatively be integrally formed with the inflatable seal-forming structure 23030. For example, the plenum chamber can include magnetic means for cooperative engagement with corresponding magnetic means in the inflatable seal-forming structure. The frame 23010 can be a skeletal frame that follows the contours of the plenum chamber 23000. For example, the frame 23010 can comprise at least two ribs, or at least three ribs extending radially from a centrally located valve socket 23040. This skeletal structure provides sufficient rigidization to the seal-forming structure 23030 and the inflatable bladder 23020 without the use of a substantial amount of hard component.

The inflatable bladder can be made of a fabric which is non-porous to air, or silicone. In this way, the bladder can contain air directly fed from a flow generator and inflate or expand.

When the inflatable bladder is expanded using air from the flow generator, the inflatable bladder is adapted such that pressure is distributed evenly and radially to expand the inflatable bladder. The delivery of air into the inflatable bladder can be initiated during a 'set up mode'. The passageway for feeding the air from flow generator can additional be integrated in the headgear or plenum chamber and hence hidden out of view. Alternatively, an external pump (both manual or auto) can be connected to the plenum chamber during initial set up to pump the inflatable bladder for usage. An opening may be incorporated in the plenum chamber to accommodate the external pump.

The air in the bladder can be retained by using at least a one way valve to stop or at least slow down the flow of out flowing air. The one way valve is fittable within a valve socket 23040 in the frame 23010. This ensures that the pressure of therapy does not get affected after the initial pumping. Another one way valve which releases air from the plenum chamber, can be added to the plenum chamber to further regulate the pressure within the plenum chamber.

The connection of the one way valve to the frame can be reinforced using an elbow ring 23050. The elbow ring 23050 can include a connecting means for reversibly attaching the one way valve. This allows the one way valve to be removed and replaced as and when required.

By using the supplied air from device at high pressure, and through a one-way valve, allow for the pressure to build up in the designed air pathway, which will then help to prop up the cushion/conduit, giving it structure as well as support.

A silicone material can be used for forming the plenum chamber and the seal-forming structure. Alternatively, a fabric material can be used. To further improve the air containing capability of the bladder, the material used to form the bladder can be double layered.

The air pathway in the inflatable bladder 23020 and/or the seal-forming structure 23030 can take different shapes and patterns to serve the desired functions. For example, other than just providing support, it can also provide movements in the cushion/conduit to serve the necessary design intent, e.g. extension, twisting, rolling up etc., as long as the pathway is continuous for the air to flow, the whole of the plenum chamber and/or seal-forming structure can be inflated. The pattern will determine how the structure blows up. Some examples of patterns are shown in FIG. 22. These patterns provide selective rigidity and flexibility to the plenum chamber and/or the seal-forming structure. Additionally, the patterns help reduce the lumpiness of the structure and the required amount of air to fill up the structure, in contrast to having a rectangular pocket for air to flow. This reduces the amount of time for the plenum chamber to "deploy".

Different patterns can also be used to provide a 3D configuration after air is pumped in. With the use of patterns, the plenum chamber can be deflated to retain a substantially flat configuration for shipping, and pumped up to adopt a 3D configuration when in use. This allows for a plenum chamber which is compact and portable, and which is easy for patients to store and bring around.

Different patterns of the air structure can serve different purposes depending on the design intent and the location of the structure within the patient interface. For example, as shown in FIG. 22, a ladder shape allows for more flexibility along the lateral direction while the vertical direction will have less flexibility. This shape will be able to give either a flat surface when pumped up, or a curved surface if the plenum chamber has a pre-moulded shape. The ladder shape can have less stretchability than the zig-zag shape. The zig-zag shape will be able to provide flexibility and stretchability in the lateral direction, while also providing some flexibility vertically. The zig-zag shape may allow the plenum chamber to curl up cylindrically when pumped, and the plenum chamber can take up a half conical shape when pumped while being able to be compressed flat when air is removed. A honeycomb or polygonal pattern can be useful in providing an even pressure distribution in the air structure. Each of these may therefore be useful in conical shapes/components. A square wave pattern can provide a slight curl in the plenum chamber. Accordingly, the inflatable bladder of the plenum chamber can comprise a combination of patterns adapted to provide a 3D configuration suitable for use.

To form the air paths (which may be meandering/tortuous) in the inflatable bladder 23020, the bladder can for example be manufactured by gluing or welding separate fabric or silicone layers together. For example, when applied in an air-holding fabric mask (such as a silicone coated-fabric or TPU-lined fabric mask), the layers can be glued/welded together in a selective manner to create the air paths.

The frame in the plenum chamber can comprise radial ribs 23060. FIGS. 23A and 23B shows an example of a frame of the plenum chamber in a front and side view respectively. The plenum chamber can be fitted with a centrally located one way valve (not shown) with at least 3 ribs 23060 extending radially from the one way valve. The distal ends of the ribs is adjacent to the seal-forming structure 23030. This provides some support such that the plenum chamber does not collapse onto the patient's nares and/or mouth when the pressure within the bladder falls.

The plenum chamber can comprise connecting means for attaching to the headgear. The connecting means can be tabs or loops configured to fit into a corresponding connecting means in the headgear. Magnets can also be used.

5.3.3 Headgear

The headgear of the present technology may be held in sealing position in use by at least the headgear tubing.

In one form of the headgear provides a retention force at least sufficient to overcome the effect of the positive pressure in the plenum chamber to lift off the face.

In one form the headgear provides a retention force to overcome the effect of the gravitational force on the patient interface.

In one form the headgear provides a retention force as a safety margin to overcome the potential effect of disrupting forces on the patient interface, such as from tube drag, or accidental interference with the patient interface.

In one form of the present technology, a headgear is provided that is configured in a manner consistent with being worn by a patient while sleeping. In one example the headgear has a low profile, or cross-sectional thickness, to reduce the perceived or actual bulk of the apparatus.

In one form of the present technology, a headgear is provided that is configured so as not to be too large and bulky to prevent the patient from lying in a supine sleeping position with their head on a pillow.

In one form of the present technology, a headgear is provided that is configured so as not to be too large and bulky to prevent the patient from lying in a side sleeping position with their head on a pillow.

Referring to FIG. 8A to 8F, in certain forms of the present technology, a headgear 8010 comprises at least one air inlet 8040 and at least one air outlet 8030. The inlet 8040 and outlet 8030 allow for the flow of air from the inlet to the outlet via headgear tubing 8060 (as indicated by the arrows). The inlet 8040 is positionable to substantially overlie a superior region of a patient's head in an as-used position. As shown in FIG. 2C, the superior region of the patient's head refers to the cranial region of the head and which is proximal to the brain. This region can include the forehead and the scalp. The inlet 8040 can be substantially at the sagittal plane, or proximate the sagittal plane. The inlet 8040 can be also be positioned at an offset from the sagittal plane and overlie a superior region. The outlet 8030 is positionable adjacent to at least one of the patient's nares when in the as-used position. Alternatively, or in addition, the outlet 8030 can be positioned adjacent to the patient's mouth. A flow of pressurised air into the inlet 8040 can be provided via a tubing 8050, to which a high pressure air source is attached at the other end of the tubing 8050.

It should be noted that an oxygen source can also be attached (together with the air source or separately) to the inlet 8040 via a tubing 4170. The attachment of an oxygen source would thus provide for oxygen therapy.

Extending between the inlet 8040 and the outlet 8030 is headgear tubing 8060. The headgear tubing 8060 is positionable to overlie a side region of the patient's head. The headgear tubing 8060 is positionable to be substantially aligned along the coronal plane in an as-used position. The flow of air from the air inlet 8040 to the outlet 8030 within the conduit or tubing 8050 of the headgear tubing 8060 is shown by arrows in FIG. 8B. FIGS. 8D and 8E shows the conduit 8050 that is formable within the headgear tubing 8060. The conduit 8050 is provided by a cavity within a double walled film. In this example, the double walled film is formed by two separate films (8080 and 8090) joined or seamed together at their edges. The edges can be further reinforced by seam tape 8120 to improve the seal and for structural integrity. The double walled film can be laminated with a textile on one or both outer facing sides of the film. In a resting or unused state, the conduit 8050 of the headgear tubing 8060 is not filled with pressurised air and is in a collapsed state (FIG. 8D). When in use, the conduit 8050 of the headgear tubing 8060 can be flushed or filled at least partially with pressurised air and be in an expanded or inflated state (FIG. 8E). The headgear tubing 8060 can transition between an inflated state and a collapsed state through the use of the conduit (or cavity) for supplying pressurised air from an air inlet to the patient's nares and/or mouth. Accordingly, when in use, the conduit 8050 in the headgear tubing 8060 is sufficiently durable to withstand pressurised air of at least 6 cm H$_2$O and of sufficient width and/or thickness in order to deliver a constant and sufficient flow of pressurised air from the air inlet to the patient. In addition to the advantage provided by the re-location of the air inlet from an 'elephant trunk' position, a further advantage is that the inflated headgear tubing avoids compression on the patient's head, which is commonly seen in patient interface with elastic straps. In either state and when in use, the headgear tubing 8060 may be positioned adjacent or proximate to the patient's head. When the headgear tubing is in the collapsed state and when not in use, the headgear tubing is elastically deformable and foldable on itself (i.e. scrunchable).

The headgear 8010 can comprise a headgear tubing 8060 which flares out into a wider portion at the front of the headgear 8010 to "hug" the plenum chamber. This provides better fluid communication from the air outlet to the patient's nares in that the connection between the air outlet and the plenum chamber is not easily dislodged during movement when in use. As the conduit is widened, breathability by the patient is also easier. The widening of the conduit also reduces the pressure at the patient's nares and/or mouth, thus is more comfortable to the patient. It also provides for a more visually appealing headgear. The headgear 8010 also comprises a tensioning structure 8020 for providing additional force to maintain the outlet 8030 in the as-used position. The tensioning structure 8020 can be connected to the headgear tubing 8060 at any point along the length of the headgear tubing 8060, as long as it can provide the additional retention force.

The headgear tubing 8060 can be formed from a composite material. The composite material can comprise a fabric inner layer 8070, which can be adjacent to or in contact with the patient's head when in use. The composite material further comprises a double walled film (8080 and 8090) as shown in FIGS. 8D and 8E. The composite material is further described below.

Another example of headgear tubing 9060 is shown in FIG. 9A, FIG. 9F and FIG. 9G. The composite material of headgear tubing 9060 comprises a double walled film (which may be formed by a first air holding material 9120 and a second air holding material 9130 connected at their respective opposite longitudinal edges for example 9125) that defines an inner cavity or conduit 9140. The first and second air holding material 9120 and 9130 each respectively has inner and outer surfaces. The double-walled film has an outer surface which is formed by the outer surface of the first air holding material 9120a and the outer surface of the second air holding material 9130a). The inner surface of the double walled film is formed by the inner surface of the first air holding material and the inner surface of the second air holding material. The inner surface of the double walled film forms a cavity or conduit through which air can pass through. The double walled film can comprise a first film 9120 forming a first wall and a second film 9130 forming a second wall, which are positioned in a spaced apart configuration such that air can flow between the cavity between the first wall and the second wall. The film 9120 and 9130 is impervious to pressurised air. To this end, the cavity 9140 within the double walled film (formed from first air holding material 9120 and second air holding material 9130) is able to contain pressurised air. In the absence of pressurised air, the cavity 9140 is not filled with pressurised air and is in a collapsed state (FIG. 9F). This collapsed state also includes, embodiments in which a gap is maintained between the inner surfaces of the first and second air holding material in the absence of air flow. The gap can, for example, be formed by providing more material to the first air holding material relative to the second air holding material. When pressurised air is flushed through the cavity, the cavity 9140 is in an inflated state (FIG. 9G). In this way, when the cavity 9140 of the composite material transits between an inflated state to a collapsed state, the headgear tubing 9060 is also able to transition between an inflated state to a collapsed state for supplying pressurised air to the patient.

In some embodiments, a first fabric layer 9150 is connected to the outer side of the first air holding material 9120a. The first fabric layer 9150 can be used as an external surface of the headgear tubing. The first fabric layer 9150 can be a mesh fabric layer. A second fabric layer 9160 is connected to the outer side of the second air holding material 9130a. The second fabric layer 9160 can be used as an internal surface of the headgear tubing, which is in contact with a patient's skin when in use. Accordingly, when used to form the headgear tubing 9060, a smooth finish provided by the second fabric layer 9160 can be in contact with the patient's head when in use, thus providing comfort.

As shown in FIGS. 9F and 9G, the headgear tubing can also comprise a fastening portion 9050 which is described in detail below. The fastening portion 9050 can be formed between a gap in the first air holding material 9120. The fastening portion acts as an air sealing layer such that the cavity is defined by the first and second air holding materials and the air sealing layer (or fastening portion 9050). Other versions in which the first air holding material is continuous (i.e. for example, absent of the fastening portion) is also possible and within the scope of the invention.

As shown in FIG. 9H, the headgear tubing has a length extending in a length axis 9180 generally between the inlet 9040 and the outlet 9030. Airflow through the headgear tubing flows generally along the length axis 9180 between the inlet 9040 and the outlet 9030. The headgear tubing has a first transverse axis 9190 extending generally transversely to the length axis 9180 of the headgear tubing and a second transverse axis 9200 that is perpendicular to the first transverse axis 9190 (and is also generally transverse to the length axis 9180). In the illustrated example, the first transverse axis 9190 may extend between the fastening portion 9050 and the second fabric layer 9160 (see e.g., FIGS. 9F-9H). In other words, the first transverse axis 9190 may intersect (e.g., transversely, perpendicularly, etc.) that patient's skin, in use. The second transverse axis 9200 may extend substantially perpendicular to the first transverse axis 9190 so that the second transverse axis 9200 extends along the patient's skin in use. The second transverse axis 9200 may also extend along a width of a foam 9170 and/or the air folding material 9130 without intersecting both the foam 9170 and the air holding material 9130. Comparing FIG. 9F and FIG. 9G, the headgear tubing is selectively expandable in a first direction (generally along the first transverse axis 9190) compared to a second direction (generally along the second axis 9200). For example, the headgear tubing may expand along the first transverse axis 9190 away from the patient's head. In other words, the first direction may be laterally away from the patient's skin. Expansion directed laterally into the patient's head may be limited by the patient's skin (although some expansion along the first transverse axis 9190 into the patient's head may occur). Alternatively, the headgear tubing expands in the first direction more than the second direction. For example, the headgear tubing may expand in the second direction (e.g., toward the crown of the patient's head (e.g., a region overlaying the parietal bone) and/or toward the mandible) but may expand more in the first direction (e.g., laterally away from the patient's face). This may be achieved by having an asymmetric geometry or by varying the material properties of the headgear tubing. For example, the first and second air holding material 9120 and 9130 can be more stretchable or expandable along the first transverse axis 9190 relative to the second transverse axis 9200. Alternatively, more material can be provided in the first air holding material 9120 relative to the second air holding material 9130 in order to allow the first air holding material to move (in the first direction along the first transverse axis 9190) relative to the second air holding material.

The selective expansion in the first direction over the second direction can be a strained inflation. This can be represented by a sigmoidal curve on a stress-strain plot. In the initial stage, the headgear tubing overcomes its initial stiffness in the first direction generally along the first transverse axis 9190. With an increase in pressured air within the conduit, the conduit "springs to attention" and pressure builds up before the headgear tubing starts to inflate. This can be represented by an initial increase in stress with no increase in strain (plateau region). During the inflation, the stress strain curve flattens out as the pressure within the conduit remains constant while the conduit expands. With a further increase in pressure, the expansion of the conduit slows down and the conduit eventually stops inflating.

Alternatively, the selective inflation in the first direction over the second direction can be a low strain inflation. In this regard, the conduit is suitably sized such that when it is inflated, the stress strain curve is not extended past the plateau region.

In one form of the headgear, the headgear tubing 9060 when in the collapsed state is substantially planar or flat. In another form, when in the collapsed state, the first and second air holding material are not under tensioned such that they are pushed away from each other. When in the inflated state, the pressurised air causes the cross-sectional shape of the headgear tubing to expand to, for example, a semi-circle shape, a dome shape or a lenticular shape, rounded rectangular shape, or elliptical shape. The change in the cross-sectional shape of the headgear tubing can be a result of how the headgear tubing is formed. For example, the double walled film can be formed as a tubular or cylindrical structure. For example, the first and second air holding material that forms the double walled film can be obtained directly by a blow extrusion process using an annular die. In this regard, the first and second air holding material are joined to form a continuous film. The first side of the first air holding material can have a positive curvature while the second side of the second air holding material can have a negative curvature. Accordingly, when the headgear tubing is viewed cross-sectionally, in the presence of a pressurised air, the first side and the second side can separate from each other in a proportional manner. As shown in FIG. 9G, the double walled film 9120 and 9130 can alternatively be formed by adhering or joining two pieces of films at their opposite ends. For example, two pieces of film 9120 and 9130 can be stacked and sewn at opposite ends to form the double walled film. The two pieces of film 9120 and 9130 can be stacked and joined at their opposite ends by radio frequency (RF) welding or ultrasonic lamination. RF welding (also known as High Frequency (HF) welding or Dielectric welding) is a method of joining thin sheets of polar thermoplastic material together. It uses high frequency (13 to 100 MHz) electromagnetic energy to fuse the materials. A rapidly alternating electric field is set up between two metal welding bars. The electric field causes the polar molecules found in some thermoplastics to oscillate and orient themselves with respect to the field. The energy generated by this process causes a temperature increase which results in melting of the materials. Combined with applied pressure from clamping the welding bars, this causes a weld to form.

The first side can have a positive curvature while the second side can have a zero curvature such that when viewed cross-sectionally, the ends of the films meet to form an inner cavity as a semi-circle or as a dome. This can be achieved by providing an excess of film material in the first air holding material 9120 relative to the second air holding material 9130. Alternatively, the first side can have a zero curvature while the second side can have a negative curvature. This can be achieved by only subjecting the second air holding material 9130 under tension such that it is less stretchable than the first air holding material 9120. When inflated, the second air holding material 9130 is not able to further expand and only the first air holding material 9120 can resiliently expand to accommodate the increase in air pressure. If an annular continuous film is used as the first and second air holding material, the second fabric layer 9160 can a tough (absorb energy and plastically deform without fracturing) but flexible material such that the second fabric layer is not stretched when the headgear tubing is inflated. In either cases, a planar portion is maintained on the second fabric layer 9160. The planar portion when inflated allows for a good fit to a patient's head for improved comfort. The planar geometry also allows a patient to sleep on his side without obstruction.

The composite material can further have a flexural modulus of less than 15 N/mm$^2$. In other embodiments, the flexural modulus is less than 14 N/mm$^2$, less than 13 N/mm$^2$, less than 12 N/mm$^2$, less than 11 N/mm$^2$, less than 10 N/mm$^2$, less than 9 N/mm$^2$, less than 8 N/mm$^2$, less than 7 N/mm$^2$, less than 6 N/mm$^2$, less than 5 N/mm$^2$, less than 4 N/mm$^2$, or less than 3 N/mm$^2$. In other embodiments, the flexural modulus is about 5 N/mm$^2$. Accordingly, the headgear tubing, when made from the composite material, can have a flexural modulus of less than 15 N/mm$^2$.

This allows the headgear in the collapsed state (FIG. 9F) to be elastically deformable. In this state, the headgear tubing is foldable on itself. This allows the headgear to be folded into a compact size for storage. This type of structure is also less bulky than previous headgear arrangements, and is easier to use.

When the headgear is in the collapsed state, the width of the headgear tubing along the first transverse axis 9190 has a thickness from about 0.5 mm to about 10 mm, about 0.5 mm to about 8 mm, about 0.5 mm to about 6 mm, about 1 mm to about 6 mm, about 2 mm to about 6 mm, or about 3 mm to about 6 mm. When the headgear is in the inflated state, the width of the headgear tubing along the first transverse axis 9190 has a thickness from about 5 mm to about 40 mm, about 10 mm to about 40 mm, about 15 mm to about 40 mm, about 20 mm to about 40 mm, about 25 mm to about 40 mm, about 30 mm to about 40 mm, or about 35 mm to about 40 mm.

The capacity of the headgear tubing in the first direction along the first transverse axis 9190 to accommodate the inflation of the conduit may be characterised by a flexural modulus. In this regard, when the double walled film is formed from a first air holding material and a second air holding material, the first air holding material may flex away from the second air holding material. In some embodiments, the flexural modulus is less than 15 N/mm². In other embodiments, the flexural modulus is less than 14 N/mm², less than 13 N/mm², less than 12 N/mm², less than 11 N/mm², less than 10 N/mm², less than 9 N/mm², less than 8 N/mm², less than 7 N/mm², less than 6 N/mm², less than 5 N/mm², less than 4 N/mm², or less than 3 N/mm². In other embodiments, the flexural modulus is about 5 N/mm².

The headgear tubing in the second direction along the second transverse axis 9200 has a thickness from about 5 mm to about 30 mm. The headgear tubing in the second direction along the second transverse axis 9200 can have a thickness from about 5 mm to about 50 mm. The thickness of the headgear tubing in the second direction along the second transverse axis 9200 can vary along the length of the headgear tubing. In particular, a greater thickness is desirable at a top portion of the headgear or proximal to the outlet of the headgear for additional stability.

The headgear further comprises a tensioning structure 8020 or 9020. The tensioning structure is for providing a force to maintain the outlet in the as-used position.

The headgear tubing is dimensioned to conform to a contour of the patient's head. When the headgear tubing is in the inflated state, the pressurised air of at least 6 cmH₂O causes the headgear to compress against the patient's head to form a tight fit with the patient's head. The slight pressure prevents the headgear from shifting during use. This further ensures that the seal of the seal-forming structure is not loosened during use. The headgear can also be manufactured in a single size, and when in use with a flow of pressurised air, can conform to the shape of the patient's head, thus being suitable for different head sizes.

The headgear tubing 8060 or 9060 can be made from a composite material that is stretchable. In one form of the present technology, the headgear tubing 9060 has a higher degree of stretchability in at least part of its length axis 9180 than in the second direction along the second transverse axis 9200. The headgear tubing can be more stretchable along at least part of its length axis 9180 than in the second direction along the second transverse axis 9200. For example, the Young's modulus along the length can be lower than the Young's modulus along the second transverse axis 9200. The stretchability is advantageous for conforming to complex and intricate body surfaces. For example, the non-uniform stretching allows for a good fit to the patient's head, by allowing a wider fit curve without sacrificing conduit stiffness. The stretchability can be tested by measuring the force before breaking with two-way stretch.

The headgear tubing can have a tensile modulus (or Young's or elastic modulus) of about 15 N/mm² to about 150 N/mm². In other embodiments, the tensile modulus is about 15 N/mm² to about 120 N/mm², about 15 N/mm² to about 100 N/mm², about 15 N/mm² to about 80 N/mm², or about 15 N/mm² to about 50 N/mm². In other embodiments, the tensile modulus is about 15 N/mm². In some embodiments, the headgear tubing may have a lower tensile modulus along its length axis 9180 than along the first and/or second transverse axes 9190, 9200, for better fit with various head sizes. In other embodiments, the headgear tubing along the second transverse axis 9200 may have a lower tensile modulus compared to that of the headgear tubing along the first transverse axis 9190.

While the flexural modulus and the tensile modulus for the composite material is provided herein, the modulus can be a combination of the material properties of the individual layers making up the composite material. For example, the inventors have found that patient comfort is improved by balancing the longitudinal forces with the tensile strain due to inflation in the transverse direction. In this regard, a difference in the modulus along the length axis 9180 and either or both of the transverse axes 9190, 9200.

Features of another embodiment of a headgear 11010 are illustrated in FIG. 11. The headgear 11010 has an air inlet 11040 and an air outlet 11030. Further details of the air inlet 11040 are shown in FIG. 11D. The inlet 11040 can be connected to an air pressure tubing 4170 which extends toward the posterior region of the patient's head. The first fabric layer 11050 is a mesh material and the second fabric layer 11060 is a breathable fabric material. As seen in FIG. 11C, the second fabric layer 11060 is in excess of the first fabric layer 11050, the excess of which folds over and covers the longitudinal sides of the first fabric layer 11050. The second fabric layer 11060 can be accordingly adhered and/or sewn to the first fabric layer 11050.

Alternatively, as shown in FIG. 11E, different textile composites can be used to make up the headgear tubing. For example, different textile composites can be used to make up the headgear tubing along its length. For example, headgear 11000 can comprise a first fabric layer 11050a which can have a different stiffness relative to first fabric layer 11050b. First fabric layer 11050a is adapted to cover the patient's nares and first fabric layer 11050b is adapted to cover the patient's mouth. Each of first fabric layer 11050a and first fabric layer 11050b can be made up of a plurality of portions so that different pressures can be selectively supplied, thereby having different relative stiffness/flexibility between first fabric layer 11050a and first fabric layer 11050b. For instance, first fabric layer 11050a can be a single portion, while first fabric layer 11050b can comprise two portions. To encourage nose breathing, the stiffness of first fabric layer 11050b can be increased such that its stiffness is higher than first fabric layer 11050a.

Different textile composites can be used to provide first fabric layer 11050a and first fabric layer 11050b. Towards this end, different textile composites can be glued, sewn or welded together along their length to form the headgear. When formed in this way, two or more substantially parallel headgear tubings may be provided to separately provide air to the nares and the mouth of the patient. Different pressurised air can be provided within the conduit of the headgear tubings, and in this way the air pressure to the nares and mouth can be separately modulated for better comfort. Alternatively, the headgear tubings in adjacent textile composites can be in fluid communication such that only one pressurised air source is required. In this configuration, the stiffness or flexibility of the textile composites can be provided by the materials used in, for example, the first fabric layer 11050a and 11050b.

Features of another embodiment of a headgear 12010 are illustrated in FIG. 12. In contrast to the embodiment of FIG. 11, the second fabric layer 12060 does not overlap the first fabric layer 12050. Rather, the first fabric layer 12050 and the second fabric layer 12060 are substantially similar sized and adhered and/or sewn to each other.

The headgear of at least some forms of the present technology provides comfort as well as user desirability. The comfort can be conferred by using materials that are light weight such as fabrics, and by arranging the headgear to have a shape that conforms to the contours of a patient's head. It is also expected that a patient will use the headgear for about 12 to 15 hours a day. To this end, the comfort of the patient can be improved as the headgear is washable. A reusable headgear is also desirable for reducing waste and cost. It is expected that the headgear can be reusable for at least 30 cycles within a 3 month period of use.

To don or doff the headgear, the patient may detach or loosen the tensioning structure (if present) and slidingly fit the headgear onto his head. The air inlet is positioned approximately along the sagittal plane and at the cranial region. The patient then fits the seal-forming structure adjacent to his nares and/or mouth. The tensioning structure is fixed and/or tightened to further secure the headgear to the patient's head. The headgear tubing and/or tensioning structure (or parts thereof) can be stretched sufficiently to allow donning and doffing without significant adjustment. In this way, the patient may not have to re-adjust or detach any parts of the headgear, helping to ensure that any adjustment made by the patient is maintained for successive uses. In other words, the headgear can be adjusted once by the patient, and then remains appropriately adjusted whether or not the headgear is worn by the patient. This may be beneficial because the patient may be better assured that the seal-forming structure will be in the proper location on each successive use after adjustment to a preferred location (e.g., at a preferred angle α1) on an initial use.

5.3.3.1 Fastening Portion

The headgear tubing can further comprise a fastening portion 9050, as illustrated in FIG. 9. The fastening portion 9050 can be on the second fabric layer 9160 or on the first fabric layer 9150. When on the second fabric layer 9160, the fastening portion 9050 is located on the inner surface of the headgear, and thus will be 'hidden' when the headgear is used. Alternatively, when the fastening portion 9050 is on the first fabric layer 9150, the fastening portion is located on an outer surface of the headgear, and thus can be visible when the headgear is used. The fastening portion 9050 is openable to expose the double walled film 9120 and 9130. Accordingly, the patient is able to access the interior of the cavity 9140. This facilitates the cleaning of the cavity 9140 of the headgear, thus providing patient assurance regarding the hygiene of the product.

The fastening portion 9050 is in contact with the headgear tubing 9060 along its length. The fastening portion 9050 can be formed as part of the first fabric layer or the second fabric layer. The fastening portion 9050 can also be formed as part of the doubled walled film. For example, referring to FIGS. 9F and 9G, the fastening portion fluidly connects two pieces of fabric to form a continuous first fabric layer 9150. In combination with the second air holding material 9130, a conduit impervious to air and can accommodate an increase in air pressure is formed. The fastening portion 9050 can also fluidly connect two pieces of air holding material to form a continuous first air holding material 9120. In combination with the second air holding material 9130, a conduit that is impervious to air and that can accommodate an increase in air pressure is formed. The fastening portion 9050 can extend from a first position proximate to the inlet to a second position proximate to the outlet. This allows for a thorough cleaning of the cavity.

Examples of fastening portion include, but are not limited to, zip, tape and hook and loop fastener.

Referring to FIG. 10A, the headgear comprises a fastening portion. The fastening portion is provided as a zip. The fastening portion 10060 when substantially fastened the headgear tubing is shown in FIG. 10B. The fastening portion can be unfastened to expose the cavity and hence the inner surface 10070 of the double walled film of the headgear tubing, as shown in FIG. 10C.

5.3.3.2 Textile Composite of the Headgear Tubing

One form of textile composite (or composite material) is illustrated in FIG. 13A. As mentioned above, in some forms of the present technology, the headgear tubing is formed from a textile which can be a textile composite material, having at least a double walled film having an inner cavity and an outer surface. The composite material can further comprise one or more fabric layers on the first and second sides of the double walled film. As shown in FIG. 13A, the composite material 13000 comprises an inner cavity or conduit 13060, which may be formed by a first air-holding material such as a film 13020 and a second air-holding material such as a film 13030. The air holding material (film 13020 and 13030) is impervious to pressurised air, and as such can hold pressurised air within the inner cavity. The first air holding material (film 13020) has an inner and outer side, the outer side is a first side 13070 of which is outward facing and distal to the inner cavity 13060. A first fabric layer 13010 is connected to the first side 13070. The second air holding material (film 13030) has an inner side and an outer side, the outer side is a second side 13080 of which is outward facing and distal to the inner cavity 13060. A second fabric layer 13040 is connected to the second side 13080. The connection of the first fabric layer 13010 to the film 13020 and the second fabric layer 13040 to the film 13030 can be by lamination or adhesive such as glue (dry, hot melt, reactive). Alternatively, ultrasonic lamination or RF welding may also be used.

The second fabric layer 13040 can be thicker than the first layer 13010. This can improve the comfort for the patient as the second fabric layer can be directly in contact with the patient's head. For example, the fabric may be thick enough to provide a cushioning effect. Examples of the second fabric layer 13040 may be non-woven fabrics or spacer materials which are soft for thermal and moisture comfort.

Alternatively, a foam material 13050 can be sandwiched between the second side 13080 and the second fabric layer 13040. The foam material provides additional comfort to the patient when in use. For further comfort, the thickness of the foam can be varied, or at least two layers of foam material can be used.

The foam material can also be sandwiched between the first side and the first fabric layer. When positioned in this way, the puffiness provided by the foam can prevent blockage of the conduit when the patient is sleeping on his side.

Features of another embodiment of a composite material are illustrated in FIG. 13C. Here, another (third) fabric layer 13090 is incorporated such that it is connected to the second side 13080. In this way, the foam layer 13050 is sandwiched between the second fabric layer 13040 and the further (third) fabric layer 13090. This provides improved connection of the film 13090 to the fabric in contact with the patient's head when in use, as due to the porous and soft nature of the foam, the connection of the film to the foam may be weak, which can result in the patient experiencing the headgear tubing 'moving' when in use.

In one form of the present technology, the headgear tubing and/or the composite material has a flexural modulus of less than 15 N/m². This allows for scrunchability (elastically deformable and foldable) such that the headgear can be folded into a compact size for storage when not in use. By choosing elastic textiles, a one size fits all headgear and/or patient interface can be produced.

When the first fabric layer 9150 is a mesh fabric, the film 9120 attached to the first fabric layer 9150 can have a high transparency. This enables the patient to see through into the cavity such that the patient is able to determine its cleanliness. The film 9130 attached to the second fabric layer 9160 may correspondingly be of low transparency, which limits the visibility of the underlying structure and provides a good background against which the patient can view through the first fabric layer 9150 and film 9120. In this regard, the film 9120 adjacent to the first fabric layer 9150 can have a higher total transmittance compared to that of the film 9130 adjacent to the second fabric layer 9160. The first fabric layer 9150, or at least a portion of the first fabric layer 9150, can have a partially transparent or translucent structure. For example, the partially transparent or translucent structure can be a mesh like structure which provides windows for users to look into the interior through the transparent or translucent portions. Fabrics can be produced with predetermined mesh opening sizes, shapes and patterns to enable optimal viewing of the tubing interior through the layer. Alternatively, a fabric made of high gauge monofilaments can be used, which provides sufficient transparency and/or translucency.

In one form of the present technology, the film has a total transmittance of more than 90%. The high transmittance of the film can provide a "see-through" ability such that the patient can inspect the headgear tubing for cleanliness. This provides assurance to the patient.

For example, the film can be selected from thermoplastic polyurethane. Materials that may provide these properties include those manufactured by the Darlington Corporation known by the trademark DARLEXX®, or the 3M product known by the trademark THINSULATE® or the Polytetrafluoroethylene (PTFE) material known as GORETEX®, or the product known as ATLANTECH™ made by Atlantis Weather Gear Inc.

In one form of the present technology, textiles are used to form the headgear. Textiles can also be used to substantially cover the double walled film 9120 and 9130. For example, the first fabric layer 9150 can be connected to the first side via thermal bonding or glue bonding. The first fabric layer 9150 can be connected to the first side via dotglue bonding. The first fabric layer provides transparency to allow confidence of the cleaniness of the cavity. The first fabric layer can also have a good hand feel. The first fabric layer can have a knit structure selected single jersey, rib, interlock, raschel, or jacquard. In other embodiments, the textile may be opaque or intrinsically transparent material which has a transparency for allowing a patient to see through the material. In other embodiments, the first fabric layer is a mesh fabric layer. Mesh fabric is a type of fabric characterized by its net-like open appearance, and the spaces between the yarns. Mesh is available in a variety of constructions including wovens, knits, laces, or crocheted fabrics. Examples of mesh fabric are A. polyester mesh: This type of fabric is lightweight and it has a noticeable ability to wick moisture. Unlike other types of fabric, polyester mesh does not get bogged down with sweat, and it is highly breathable.

B. nylon mesh: This type of mesh is lightweight but has a higher rigidity than polyester mesh.

C. Tulle: This type of mesh may be made from silk.

D. Power mesh: Power mesh is known for its compression abilities. This type of fabric has an almost entirely sheer appearance. It is named due to its higher elasticity.

E. Powernet: This type of mesh fabric features a relatively dense weave.

The first fabric layer 9150 and second fabric layer 9160 can each be a composite fabric or textile. The composite fabric or textile is a material which is produced from two or more constituent materials. The composite fabric or textile can also have a weave pattern that provides improved strength of the composite fabric or comfort to the patient, for example. Within the finished composite fabric product, the individual components remain separate and distinguishable. The composite fabric can be formed as two or more constituent materials intertwined together as a single sheet or layer of fabric. Alternatively, the composite fabric can comprise two or more layers, each layer comprising a different adjacent fabric. For example, different types of textiles, foam, fiberfill, spacer fabrics, non-woven, knit, and woven can be used. The spacer fabric may be a multifilament spacer fabric. A composite fabric with layers of different materials allows the benefits of the respective materials to be conferred to the headgear.

The second fabric layer 9160 can be connected to the second side via thermal bonding or glue bonding. For example, the second fabric layer 9160 can be connected to the second side via dotglue bonding. The second fabric layer 9160 can be an opaque material. The second fabric layer 9160 can be selected from microfiber yarns, nylon 6,6, peach-skin finish, elastic knitted fabric, two way stretch, non stretch, circular knit fabric, woven fabric, or warp knit fabric.

The second fabric layer 9160 can be further surface-treated with a hydrophobic coating. This prevents the fabric from absorbing sweat from the patient's skin and can thus prolong the film from degradation. The second fabric layer 9160 can also be surface treated with mineral to assist blood circulation. The second fabric layer 9160 can also be surface treated with a hydrophobic and/or oleophilic coating for moisture wicking functionalities.

In one form of the present technology, the second fabric layer 9160 and the first fabric layer 9150 overlap. The second fabric layer 9160 can be annealed by heat bonding or glued to the first fabric layer 9150. Alternatively, the second fabric layer 9160 can be joined or attached to the first fabric layer 9150 by any other means. This can provide additional strengthening to the film to prevent rupture.

The composite material, being textile based, allows for temperature control and moisture management to enhance the comfort level of the patient. The textile also can provide a good hand feel with a soft touch that provides the patient a calm and soothing therapy experience. By choosing elastic textiles, adjustments using, for example, clips can be eliminated. This makes the headgear easier to use to encourage greater compliance with usage of the patient interface. Further, a one size fits all headgear and/or patient interface can be produced and thus reduce manufacturing cost.

In one form of the present technology, FIGS. 9F and 9G shows the headgear tubing and/or the composite material further comprising a foam 9170 sandwiched between the second fabric layer 9160 and the second side of the double walled film 9130. The foam 9170 can be an aerogel (such as silica aerogel or carbon aerogel) or a polyurethane foam such as memory foam or a latex foam. The foam can be a fast recovery (resilient) type or a slow recovery type (memory foam). Alternatively, a soft material like microfiber or non-woven layer may be provided as an alternative to the foam.

The softness can be incorporated into the fabric manufacture itself, by using for example thick soft fabric structure, spacer, or jacquard. The layer may be provided with thermal and moisture management properties (porosity, wicking). This acts as a cushion and provides additional comfort to the patient.

In one form of the present technology, the headgear tubing further comprises another (third) fabric layer. The third fabric layer can be sandwiched between the film 9130 and the second fabric layer 9160. In some embodiments, the foam 9170 is sandwiched between the second fabric layer 9160 and the third fabric layer. The second fabric layer 9160 and the third fabric layer can be made of different types of fabric.

Depending on the presence of the foam 9170, the second fabric layer 9160 can have a thickness to provide for comfort. For example, in the absence of the foam 1970, the second fabric layer 9160 can have an increased thickness relative to the first fabric layer 9150. The second fabric layer 9160 can have a thickness from about 0.1 mm to about 10 mm. The second fabric layer 9160 can be a double faced fabric.

In one form of the present technology, the headgear tubing comprises seam tape. The seam tape can be used to water proof the headgear tubing by sealing connecting and/or adjacent components of the headgear tubing. For example, seam tape can be applied to the longitudinal edges of the first and second air holding materials, and/or to a connection between the air holding material and the fastening portion (if present). For example, FIGS. 8D and 8E illustrate seam tape 8120 applied to the longitudinal edges of the double walled film. The seam tape can comprise a heat activated adhesive on one side which is applied to the double walled film and a waterproof and/or non-porous membrane on the other side. Seam tape can be used to stop water (and/or air) from coming through the seam and needle holes made when sewing the double walled film.

In one form of the present technology, the headgear tubing and/or the composite material has a thickness of about 4 mm to about 2 cm.

5.3.3.3 Rigidiser

Some forms of the present technology aim to avoid or minimize the creation of bends and kinks along the inflatable conduit which might obstruct or restrict airflow during use. For example, as shown in FIG. 14A, when the headgear 14010 is in use and the headgear tubing is bent over the user's head and the conduit is pressurised, the air pressure in the conduit tends to straighten the conduit, but as the conduit has to conform to the user's head, the conduit and hence the headgear may be caused to fold and/or collapse. With increased curvature of a user's head, for example when the user is a child and the curvature of the bend is increased, there can further be a restriction in air flow. This is exhibited as a kink 14020. When the headgear is pulled, the transverse force flattens the layers, restricting air flow. Further, due to the tendency of the inflatable conduit to straighten and correct itself, a good fit (and/or contact) with the user's head throughout the conduit and thus the headgear may not be obtained in all cases.

Accordingly, a rigidiser and/or stiffener can be incorporated into the headgear to overcome or at least ameliorate this problem. To this end, as shown in FIG. 14B, the headgear 14000a comprises a rigidiser or stiffener (hidden) which can maintain a curved and kink-free shape of the headgear when in use. A good inflation with generally smooth curvature and minimal to no folding can be obtained. The headgear is also still flexible and scrunchable after the incorporation of the rigidiser.

The rigidiser can be positioned within the headgear tubing, and can in some embodiments be adhered to an outer surface of the double walled film. For example, and with reference to FIG. 21, the rigidiser 21010 can be positioned adjacent to and contacting the second air holding material 21020. In other embodiments, the rigidiser 21010 is adhered to second air holding material 21020. When the rigidiser 21010 is positioned in closer proximity with the patient's head, it was found that the rigidiser 21010 and hence the headgear is able to conform more closely to the shape of the patient's head. The rigidiser 21010 is preferably sandwiched between the first fabric layer 21030 and second fabric layer 21040. This hides the rigidiser 21010 from the user and provides for a more visually appealing product.

Referring to FIG. 21, the rigidiser 21010 can be positioned adjacent to and contacting a foam 21050, if present. The rigidiser 21010 can be positioned between an outer surface of the double walled film at the second air holding material 21020 and the foam 21050. The foam 21050 can be positioned between the double walled film at the second air holding material 21020 and the second fabric layer 21040. This prevents the hard surface of the rigidiser 21010 from being felt by the patient when in use. Alternatively, the rigidiser 21010 can be positioned within the foam, or sandwiched between two layers of foam (21050 and 21060). This can reduce or eliminate uneven surfaces created by the attachment of the rigidiser 21010 to the outer surface of the double walled film, which can cause disturbance to the airflow.

FIG. 15A shows the components of the headgear tubing 15000 with the rigidiser 15220 in an exploded view. The headgear tubing comprises a double walled film having a first side 15020 and a second side 15030. The rigidiser is positioned between the second side 15030 of the double walled film and the second fabric layer 15040. A first fabric layer 15100 covers the first side 15020 of the double walled film. The rigidiser 15220 comprises a spine structure 15230 which extends substantially along the length of the headgear and protrusions 15240 extending out from the spine structure. The protrusions 15240 are positioned along the spine structure 15230 at about ⅔ of its length. As shown in FIG. 15A, the rigidiser for the right and left side of the headgear is formed as a single unit, with a ring shaped collar structure about at midway the length of the rigidiser 15220.

FIG. 15A shows the rigidiser 15220 traversing the entire length of the headgear tubing 15000. FIGS. 15B and 15C shows other embodiments of the rigidiser attached to a second fabric layer 15040 for illustration purposes. The spine structure 15230 and protrusions 15240 can be formed with different width and length to provide a range of stiffness and support. The length of the spine 15230 can be about ⅔ the length of the headgear tubing.

In FIGS. 15B and 15C, the rigidiser 15220 can have a length which extends at least partly along the headgear tubing. For example, the rigidiser 15220 can traverse at least partly along the length of the headgear and/or patient interface. This provides support and stabilisation for the seal forming structure and/or plenum chamber.

The width of the rigidiser 15220 can be approximately the width of the headgear tubing along the second transverse axis. Alternatively, the width of the rigidiser can be a portion of the width of the headgear tubing along the second transverse axis. For example, the width of the rigidiser 15220 can be less than about 90% the width of the headgear tubing along the second transverse axis, or less than about 80%, about 70%, about 60% or about 50%. In other embodiments, the width is less than about 50% the width of the headgear tubing along the second transverse axis. As shown in FIG. 16C, the width 16280 of the rigidiser can be about ¼ to about ½ the width of the headgear tubing along the second transverse axis. This provides sufficient support to the headgear without significantly increasing the cost of fabrication. Extending the width of the rigidiser to more than ½ the width of the headgear tubing along the second transverse axis can provide greater support while minimizing the presence of kinks and accordingly a high end appeal to the user.

The rigidiser 15220 can comprise a spine structure 15230 which extends at least partly along the headgear and/or patient interface. In this regard, as the spine structure 15230 follows the contours of the inflatable conduit, the spine structure can be straight, curved or bent. The spine structure 15230 can be positioned at a central region along the length of and adjacent to the double walled film. This is advantageous for providing a centralised support to the inflatable conduit.

The spine structure can have a width of about 1 mm to about 10 mm. As shown in FIG. 16C, the width 16270 of the spine structure can be about 5 mm Various widths may be used to obtain different stiffnesses. At regions of the headgear tubing where the curvature is greater and hence more stiffness is required, the width of the spine structure can be increased. In this regard, the spine structure can have a varying width along its length. For example, the spine structure can have a tapered profile, with a thicker width at a region near the air inlet and a thinner width at a region near the plenum chamber. For example, the width can be about 4 mm to about 5 mm at one end and about 2 mm to about 3 mm at the other end.

Further, the cross sectional thickness of the spine structure can vary across the width of the spine structure. For example, the thickness at an end of the lateral sides can be thinner than the central region of the spine structure. In this regard, the spine structure has a curved cross section or a dome cross section. This increases the support that is provided by the rigidiser.

The rigidiser 15220 can also comprise a plurality of protrusions 15240 extending from at least one lateral side of the spine structure. The protrusions 15240 are spaced apart from each other at intervals along a length of the spine structure. For example, the rigidiser can be formed as a fishbone structure.

Each of the protrusions 15240 can have a same length and/or breadth. Alternatively, depending on the position of the protrusions along the spine structure and its position along the length of the headgear tubing, the length and/or breadth of the protrusions can each be different.

The protrusions 15240 can have a shorter length compared to the length of the spine structure. The protrusion length can have a longer length than the width of the spine structure. The protrusions can have a thinner breadth/width compared to the width of the spine structure.

The protrusion 15240 can take various shapes. For example, the protrusion can have a quadrilateral shape. Alternatively, the protrusion can have a curved shape such as a curved spike. The curved shape can be rounded at a tip of the protrusion.

The protrusions 15240 can be positioned at various angles to the spine structure 15230. For example, the protrusions can each have a contact angle (a point of contact of the spine structure) of about 90° to the spine structure. The contact angle as used herein refers to an angle which is 90° or less (acute angle), measured at the point which the protrusion meets with the spine structure. When viewed relative to the collar structure, the acute angle can be forward facing or backward facing. The protrusions can further each have a contact angle of about 20° to about 60°. Preferably, the protrusions are at about 30° to about 50°, or about 35° to about 45°.

The protrusions 15240 can be formed on one lateral side of the spine structure 15230, or at both lateral sides of the spine structure. When formed on both sides of the spine structure, each protrusion on one side of the spine structure can have an opposing protrusion at the other side. The protrusion and opposing protrusion can be symmetrically shaped and/or positioned. For example, the contact angle of the protrusion and opposing protrusion can be the same or similar. Alternatively, the protrusions may be arranged on the two lateral sides of the spine structure such that protrusions on one lateral side is offset along the longitudinal direction relative to protrusions on the other lateral side, giving it an alternating pattern. FIG. 20B shows an example of the offset arrangement of the protrusions.

Some of the protrusions 15240 can be conjoined to provide additional strength and/or support for certain portions of the headgear. For example, FIG. 16 shows the components of the headgear tubing 16000 with the rigidiser 16220. The rigidiser 16220 is sandwiched between a second fabric layer 16040 and a second side 16030 of the double walled film. The first side 16020 of the double walled film is adjacent to a first fabric layer 16100. The rigidiser 16220 comprises a spine 16230 and a plurality of protrusions 16240. The rigidiser 16220 is formed as a single piece extending towards the left and right side of the headgear tubing, with a collar structure 16250 positioned substantially at a centre of its length. The rigidiser 16220 further comprises at least one tab 16260 along a lateral side of the spine structure 16230. In this particular embodiment, two tabs 16260 are installed for connecting to the tensioning structure (not shown) at the right and left side of the headgear 16000.

FIG. 18A shows adjacent protrusions 18240 of the rigidiser 18220 positioned near the inlet of the headgear can be conjoined at 18260 such that the stiffness prevents the inlet from being compressed or folded when in use. Alternatively, some of the protrusions can be replaced with other structural means, such as a tab 18260. When positioned near the tensioning structure, the tab 18260 can be used to provide additional support and prevent contortion when the headgear is under tension.

Alternatively, FIG. 16B shows the tab 16260 connected to the spine 16230, adjacent to and parallel to the protrusions 16240. In this arrangement, the protrusions are not conjoined to form the tab 16260. Rather, the tab 16260 is attached directly to the spine 16230 as a separate member. This allows the tab 16260 to be displaced at an angle to the spine without contorting the spine and the protrusions.

The rigidiser 15220 can further comprise a collar structure 15250. The collar structure 15250 can be positioned at one end of the spine structure. The collar structure is for providing additional rigidity to a region adjacent to the air inlet. This ensures that the breathable air is not obstructed from entering the inflatable conduit, which may occur when the region surrounding the air inlet is compressed as the user turns during sleep. To this end, the collar structure is formed to substantially surround the air inlet. The collar structure can be formed as a curved structure, or can be a straight structure. As long as the collar structure does not impede the air inlet and the flow of air, it can be of any shape.

The rigidiser as disclosed above is described as a support element which traverse through one half of the headgear and/or patient interface. In this regard, two pieces of rigidisers can be incorporated into the headgear and/or patient interface (one for the right side and one for the left side) to provide support for the whole of the device. It would be clear that the rigidiser can also be formed as a single unit for incorporation into the right and left side of the headgear tubing. Towards this end, the rigidiser 16220 can, for example, be formed with a spine structure and the collar being a C-ring structure 16250, positioned substantially at a midpoint along the length of the spine structure. This can be done, for example, by combining two rigidisers as disclosed above at their respective C-ring structures to form a collar structure.

The rigidiser can further comprise at least one tab. When the rigidiser with a tab is formed with the inflatable conduit and the tab is extended outwardly from the inflatable conduit, a tensioning structure can be connected to the tab and thus provides additional support between the inflatable conduit and the tensioning structure. The tab can comprise a slit for connecting to the tensioning structure. The tab can further comprise at least one cutout portion for providing flexibility to the tab. The tab advantageously does not cause flattening of the inflatable conduit (and hence headgear and/or patient interface) when tensioned by the tensioning structure.

The rigidiser is provided as a thin material. The rigidiser can have a thickness of less than about 2 mm, about 1 mm or about 0.5 mm. The rigidiser can have a thickness of about 100 μm to about 2 mm. The thicker the rigidiser, the stiffer it is and hence more support is provided. Preferably, the thickness is about 100 μm or about 1500 μm, about 100 μm or about 1000 μm, about 250 μm or about 500 μm, about 200 μm or about 500 μm, or about 250 μm or about 400 μm.

In one form of the present technology, the rigidiser has a higher degree of stretchability in at least part of its length over the second direction along the second transverse axis. The headgear tubing can be more stretchable in at least part of the length relative to the second direction along the second transverse axis. For example, the Young's modulus in the length can be lower than the Young's modulus in the second direction along the second transverse axis. The stretchability is advantageous for conforming to complex and intricate body surface. For example, the non-uniform stretching allows for a good fit to the patient's head, by allowing a wider fit curve without sacrificing conduit stiffness. The stretchability can be tested by measuring the force before breaking with two-way stretch.

The rigidiser can further comprise a stretchable portion. The stretchable portion can be part of the spine structure. For instance, the stretchable portion can be a zig-zag, square-wave, wavy or serpentine structure. These structures, by way of their design, allows for deformation when pulled along its longitudinal axis. This imparts more stretchability to the rigidiser where needed, for instance on the top and curved portions of the head. FIGS. 20D to 20D-2 show some examples of the stretchable structures on the rigidiser 20000. For example, FIGS. 20D-1 and 20D-2 show the protrusions 20240a on both lateral sides of the spine 20230 can be opposing configuration (see also FIG. 20A). Alternatively, FIG. 20D shows the protrusions 20240b and 20240c can be in an alternating configuration; i.e. a protrusion on one side is laterally spaced relative to an opposing protrusion (see also FIG. 20B). In addition to an elongated structure, the spine 20230a can also be in a zig-zag structure (see e.g., FIG. 20D), a square wave structure (see e.g., FIG. 20D-1), or a sinusoidal structure (see e.g., FIG. 20D-2). This allows the rigidiser to be stretchable. The spine 20230 can be made from a more rigid material relative to the protrusions, or an elastomeric material. For example, FIG. 20C shows a spine 20230 constructed from an elastic material while the protrusions are constructed from a rigid material. Alternatively, the spine 20230 may not be made from an elastomeric material, but may be more flexible than the protrusions.

The headgear tubing can have a tensile modulus (or Young's or elastic modulus) of about 5 N/mm² to about 150 N/mm². In other embodiments, the tensile modulus is about 5 N/mm² to about 120 N/mm², about 5 N/mm² to about 100 N/mm², about 5 N/mm² to about 80 N/mm², about 5 N/mm² to about 50 N/mm², about 10 N/mm² to about 50 N/mm², or about 15 N/mm² to about 50 N/mm². In other embodiments, the tensile modulus is about 15 N/mm². In some embodiments, the headgear tubing may have a lower tensile modulus along the length 9180 as compared to along the first and/or second transverse axes 9190, 9200 for better fit with various head sizes. In other embodiments, headgear tubing along the second transverse axis 9200 may have a lower tensile modulus as compared to the headgear tubing along the first transverse axis 9190.

The rigidiser can be made from a plastic or polymer material. For example, a thermoplastic elastomer like material can be used for its strength, flexibility and stretchability. Nylon, polyamide, polycarbonate, and PC-ABS blends can also be used.

The spine and the protrusions can be made of different materials. The spine structure can be made of a resilient material, for instance an elastomeric material), whereas the protrusions may be made of more rigid materials, for instance plastics. The spine may be made of an elastomeric material, such as thermoplastic elastomer (TPE), thermoplastic polyurethane (TPU) or Silicone rubber, while the protrusions may be made of more rigid polymers like nylon, polyamide, polycarbonate, and PC-ABS blends. The protrusions can also be made of an elastomer which is of a stiffer grade than that of the spine. FIG. 20 shows an embodiment of this configuration. The different materials of the spine and the protrusions can impart different stretchability and/or flexibility, and hence allow for a rigidiser which is resilient while at the same time flexible.

The spine and the protrusions can also be of different thickness. For example, the spine can be thicker than the protrusions by more than about 1 cm, about 2 cm, about 4 cm, about 5 cm, or about 10 cm.

FIG. 17 shows another embodiment of the rigidiser 17220. The rigidiser 17220 comprises a spine structure 17230, a collar structure 17250 and a tab 17260. The width of the spine structure 17230 is about 4-5 mm at a region proximate to the collar structure and about 2-3 mm at a region proximate to the tab 17260. While the spine structure 17230 is shown as a straight structure, a curved spine structure that conforms to the length of the headgear can also be used.

FIG. 18A shows another embodiment of the rigidiser 18220 adhered to a second side 18030 of the double walled film. The spine structure 18230 does not traverse the full length of the side 18030 and thus the headgear. A gap is present between the collar structure 18250 of a rigidiser and a collar structure of an adjacent rigidiser. The collar structure is formed from two C-ring structures. The gap can be adjusted depending on the amount of support required. The width of the rigidiser is about ⅓ the width of the side 18030. Tab 18260 comprises a slit and is formed as a single part with the rigidiser 18220. To this end, some of the protrusions are removed to accommodate the tab 18260.

FIG. 18B shows another embodiment of the rigidiser 18220. In contrast to FIG. 18A, the spine structure 18230 is formed such that it extends the full length of the headgear. Protrusions are formed at about ⅔ the length of the rigidiser 18220. Slots are also formed within the tab 18260. The collar structure 18250 is stiffened with additional support ribs.

FIG. 18C shows an embodiment of the headgear tubing 18000 with a rigidiser 18220 positioned within. As the rigidiser is positioned next to the second fabric layer which is soft and thin, the pattern of the rigidiser can be seen and felt.

FIG. 19 illustrates the principle of the rigidiser 19220 when in use. When the rigidiser is bent (L is bent with respect to the plane of the flat rigidiser away or toward the plane), points 1 and 2 tend to remain in the same plane, while point 3 is in a different plane due to the bend. If the rigidiser 19220 is bonded to a flexible material (film), this property can be used to anchor the centreline while the sides can be lifted up with respect to the centreline during bending. Since the protrusions (fishbones) 19240 are at an angle to the central spine, folds perpendicular to the centreline are not propagated, while allowing for bending flexibility of the rigidiser attached film.

The rigidiser can be formed using techniques such as die-cutting from sheets, injection moulding, direct deposition using fusion and curing paste or using a screen and stencil printing. Selective thermal rigidisation (embossed pattern) and bonding can also be used. The rigidiser can be bonded to the side of the double walled film using heat bond, or heat bonding via an intermediate film. Alternatively, an adhesive layer can be used.

To incorporate the rigidiser into the headgear, the rigidiser can, for example, be bonded onto the side of the double walled film. The first fabric layer and second fabric layer can then be stacked to sandwich the double walled film and the components RF welded together. When tabs are present on the rigidiser, the tabs can be protected with a protective sheet to prevent the tabs from bonding to the double walled film. Slits are then cut on the second fabric layer for the tabs to pass through, and then inserted into grooves in a mould such that when the components are RF welded together, the tabs are not exposed and thus bonded. With reference to FIG. 13A-C, the rigidiser is located at the second side 13080, for example between the second air holding material 13030 and the second fabric layer 13040.

The rigidiser can be optionally further bonded to the second fabric layer, or to the foam material or third fabric layer if present.

5.3.4 Tensioning Structure

The seal-forming structure 3100 of the patient interface 3000 of the present technology may be held in sealing position in use by the tensioning structure 3300.

In one form the tensioning structure is positionable to overlie a posterior region of the patient's head.

In one form the tensioning structure 3300 provides a retention force at least sufficient to overcome the effect of the positive pressure in the plenum chamber 3200 to lift off the face.

In one form the tensioning structure 3300 provides a retention force to overcome the effect of the gravitational force on the patient interface 3000.

In one form the tensioning structure 3300 provides a retention force as a safety margin to overcome the potential effect of disrupting forces on the patient interface 3000, such as from tube drag, or accidental interference with the patient interface.

In one form of the present technology, a tensioning structure 3300 is provided that is configured in a manner consistent with being worn by a patient while sleeping. In one example the tensioning structure 3300 has a low profile, or cross-sectional thickness, to reduce the perceived or actual bulk of the apparatus. In one example, the tensioning structure 3300 comprises at least one strap having a rectangular cross-section. In one example the tensioning structure 3300 comprises at least one flat strap.

In one form of the present technology, a tensioning structure 3300 is provided that is configured so as not to be too large and bulky to prevent the patient from lying in a supine sleeping position with a back region of the patient's head on a pillow.

In one form of the present technology, a tensioning structure 3300 is provided that is configured so as not to be too large and bulky to prevent the patient from lying in a side sleeping position with a side region of the patient's head on a pillow.

In one form of the present technology, a tensioning structure 3300 is provided with a decoupling portion located between an anterior portion of the tensioning structure 3300, and a posterior portion of the tensioning structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the tensioning structure 3300 and disrupting the seal.

In one form of the present technology, a tensioning structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In one form of the present technology, the strap is an elastic band. The strap can be constructed and arranged so that in use at least a portion of an inferior edge thereof passes superior to an otobasion superior of the patient's head and overlays a portion of a parietal bone. Alternatively, the strap can be constructed and arranged so that in use at least a portion of a superior edge thereof passes inferior to an otobasion inferior of the patient's head and overlays a portion of an occipital bone.

In certain forms of the present technology, a tensioning structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the tensioning structure is an elastic structure. The tensioning structure can be made of an elastic material, or an elastic textile. For example, thermoplastic polyurethane (such as J Fiber) can be used. A resilient fabric with a relatively flat load-elongation curve may also be used. Alternatively, a 90% Nylon and 10% Spandex material can be used. Such material allows for stretch, support, cooling and breathability, thus improving the comfort of the patient. Additionally, as the positioning and stabilising structure, being stretch fit, can apply a constant compression force on the patient's head, the headgear can be a one size fits all product.

For example, the tensioning structures 8020 and 9020 in FIG. 8B and FIG. 9A respectively are arranged so that in use, in each case, at least a portion of an inferior edge thereof passes superior to an otobasion superior of the patient's head and overlays a portion of a parietal bone. The tensioning structure 10030 in FIG. 10A and 11020 in FIG. 11A are arranged so that in use at least a portion of a superior edge thereof passes inferior to an otobasion inferior of the patient's head and overlays a portion of an occital bone. The tensioning structure 12020 in FIG. 12 is arranged so that in use the edge thereof passes superior to an otobasion superior of the patient's head and overlays a portion of a parietal bone and also passes inferior to an otobasion inferior of the patient's head and overlays a portion of an occipital bone.

Alternatively, the tensioning structure can be made of the textile composite as disclosed herein. When formed in this manner, the headgear tubing can extend into the tensioning structure such that when the conduit of the headgear tubing is expanded, additional support is provided to a posterior region of a patient's head when in use.

In one form of the present technology, the tensioning structure comprises a first tie, the first tie being constructed and arranged so that in use at least a portion of an inferior edge thereof passes superior to an otobasion superior of the patient's head and overlays a portion of a parietal bone. The first tie can further avoid overlaying the occipital bone.

In another form of the present technology, the first tie is constructed and arranged so that in use at least a portion of a superior edge thereof passes inferior to an otobasion inferior of the patient's head and overlays a portion of a occipital bone.

In another form, the first tie is constructed and arranged so that in use it passes over both an otobasion inferior and otobasion superior of the patient's head and overlays a portion of a parietal bone and a occipital bone.

In one form of the present technology suitable for a nasal-only mask or for a full-face mask, the tensioning structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the tensioning structure includes a third tie that is constructed and arranged to interconnect the first tie and the second tie to reduce a tendency of the first tie and the second tie to move apart from one another.

In certain forms of the present technology, a tensioning structure 3300 comprises a strap that is bendable and e.g. non-rigid. An advantage of this aspect is that the strap is more comfortable for a patient to lie upon while the patient is sleeping.

In certain forms of the present technology, a tensioning structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

In certain forms of the present technology, the tensioning structure 10030 further comprises a retention structure 10040. The retention structure can be a fabric or a textile, for providing additional support and stabilisation. The retention structure 10040 can substantially cover the otobasion region of the patient's head.

In certain forms of the present technology, the tensioning structure is detachable from the headgear and/or patient interface. This facilitates washing for hygiene purposes. The tensioning structure can be attachable to the headgear and/or patient interface via connecting means. For example, female connector (such as tabs) extending out from the headgear can be coupled with a corresponding male connector (such as Velcro) on the tensioning structure. Male connector can also be present on the headgear for coupling with the female connector on the tensioning structure. The connector on the headgear can be anchored to an edge of the inflatable conduit, for example at a region where the first air holding material 9120 and a second air holding material 9130 connected at their opposite ends. Alternatively, the connector on the headgear can be anchored on a surface of the inflatable conduit, for example on the first air holding material 9120a or second air holding material 9130a. Further advantageously, when the connector is anchored on a surface of the inflatable conduit, and especially on a surface in closer proximity to the patient's head, the inflated conduit is not unduly asymmetrically stretched and/or flattened when the tensioning structure is coupled and in use.

5.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 5 to about 100 holes, about 10 to about 90 holes, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel. The vent on a plenum chamber 9110 is also shown in FIG. 9E.

The vent 9080 may be integral with the headgear. For example, the vent 9080 can be positioned proximate to the outlet 9030 of the headgear. The vent 9080 can also be positioned proximate to the plenum chamber 9110. The vent 9080 can be part of the headgear tubing 9060.

In this way, gases exhaled by the patient can exit via the vents to ambient, The vents are appropriately sized and shaped to maintain the therapeutic pressure in the plenum chamber 9110 when in use. Advantageously, by integrating the air vent with the headgear tubing, in addition to expelling carbon dioxide, excessive pressurised air can also be expelled, thus allowing for better regulation and flow of air to the nares of the patient. This combination allows the headgear to be more compact.

5.3.6 Decoupling Structure(s)

In one form the patient interface 3000 includes at least one decoupling structure, for example, a swivel or a ball and socket.

5.3.7 Connection Port

Connection port 3600 allows for connection to the air circuit 4170.

5.3.8 Forehead Support

In one form, the patient interface 3000 includes a forehead support 3700.

5.3.9 Anti-Asphyxia Valve

In one form, the patient interface 3000 includes an anti-asphyxia valve.

5.3.10 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT DEVICE

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document. The RPT device can comprise the headgear and/or the patient interface as disclosed herein.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or 3800.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or 3800.

5.4.1.3 Pressure Generator

In one form of the present technology, a pressure generator 4140 for producing a flow, or a supply, of air at positive pressure is a controllable blower 4142.

For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000 or 3800.

In one form, a signal from a transducer 4270 may be filtered, such as by low-pass, high-pass or band-pass filtering.

5.4.1.4.1 Flow Rate Sensor

A flow rate sensor in accordance with the present technology may be based on a differential pressure transducer, for example, an SDP600 Series differential pressure transducer from SENSIRION.

In one form, a signal generated by the flow rate sensor and representing a flow rate is received by the central controller.

5.4.1.4.2 Pressure Sensor

A pressure sensor in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor and representing a pressure is received by the central controller.

5.4.1.4.3 Motor Speed Transducer

In one form of the present technology a motor speed transducer is used to determine a rotational velocity of the motor 4144 and/or the blower 4142. A motor speed signal from the motor speed transducer may be provided to the therapy device controller 4240. The motor speed transducer may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller.

In one form, the input device may be constructed and arranged to allow a person to select a value and/or a menu option.

5.4.2.3 Central Controller

In one form of the present technology, the central controller is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller is a dedicated electronic circuit.

In one form, the central controller is an application-specific integrated circuit. In another form, the central controller comprises discrete electronic components.

The central controller may be configured to receive input signal(s) from one or more transducers 4270, one or more input devices, and the humidifier 5000.

The central controller may be configured to provide output signal(s) to one or more of an output device, a therapy device controller, a data communication interface, and the humidifier 5000.

In some forms of the present technology, the central controller is configured to implement the one or more methodologies described herein, such as the one or more algorithms which may be implemented with processor-control instructions, expressed as computer programs stored in a non-transitory computer readable storage medium, such as memory. In some forms of the present technology, the central controller may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock that is connected to the central controller.

5.4.2.5 Therapy Device Controller

In one form of the present technology, therapy device controller is a therapy control module that forms part of the algorithms executed by the central controller.

In one form of the present technology, therapy device controller is a dedicated motor control integrated circuit. For example, in one form a MC33035 brushless DC motor controller, manufactured by ONSEMI is used.

5.4.2.6 Protection Circuits

The one or more protection circuits in accordance with the present technology may comprise an electrical protection circuit, a temperature and/or pressure safety circuit.

5.4.2.7 Memory

In accordance with one form of the present technology the RPT device 4000 includes memory, e.g., non-volatile memory. In some forms, memory may include battery powered static RAM. In some forms, memory may include volatile RAM.

Memory 4260 may be located on the PCBA 4202. Memory may be in the form of EEPROM, or NAND flash.

Additionally, or alternatively, RPT device 4000 includes a removable form of memory, for example a memory card made in accordance with the Secure Digital (SD) standard.

In one form of the present technology, the memory acts as a non-transitory computer readable storage medium on which is stored computer program instructions expressing the one or more methodologies described herein, such as the one or more algorithms.

5.4.2.8 Data Communication Systems

In one form of the present technology, a data communication interface is provided, and is connected to the central controller. Data communication interface may be connectable to a remote external communication network and/or a local external communication network. The remote external communication network may be connectable to a remote external device 4286. The local external communication network may be connectable to a local external device.

In one form, data communication interface is part of the central controller. In another form, data communication interface is separate from the central controller, and may comprise an integrated circuit or a processor.

In one form, remote external communication network is the Internet. The data communication interface may use wired communication (e.g. via Ethernet, or optical fibre) or a wireless protocol (e.g. CDMA, GSM, LTE) to connect to the Internet.

In one form, local external communication network utilises one or more communication standards, such as Bluetooth, or a consumer infrared protocol.

In one form, remote external device is one or more computers, for example a cluster of networked computers. In one form, remote external device may be virtual computers, rather than physical computers. In either case, such a remote external device may be accessible to an appropriately authorised person such as a clinician.

The local external device may be a personal computer, mobile phone, tablet or remote control.

5.4.2.9 Output Devices Including Optional Display, Alarms

An output device in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver receives as an input the characters, symbols, or images intended for display on the display, and converts them to commands that cause the display to display those characters, symbols, or images.

5.4.2.9.2 Display

A display is configured to visually display characters, symbols, or images in response to commands received from the display driver. For example, the display may be an eight-segment display, in which case the display driver converts each character or symbol, such as the figure "0", to eight logical signals indicating whether the eight respective segments are to be activated to display a particular character or symbol.

5.5 AIR CIRCUIT

An air circuit 4170 in accordance with an aspect of the present technology is a conduit or a tube constructed and arranged to allow, in use, a flow of air to travel between two components such as RPT device 4000 and the patient interface 3000 or In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000 or 3800.

5.6 HUMIDIFIER

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor 4274 provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 BREATHING WAVEFORMS

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak−0.5 L/s. The total duration of the breath, Ttot, is about 4 s. The person typically breathes at a rate of about 15 breaths per minute (BPM), with Ventilation Vent about 7.5 L/min A typical duty cycle, the ratio of Ti to Ttot, is about 40%.

5.8 SCREENING, DIAGNOSIS, MONITORING SYSTEMS 5.8.1 Polysomnography

FIG. 7A shows a patient 1000 undergoing polysomnography (PSG). A PSG system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

5.8.2 Non-Obtrusive Monitoring System

One example of a monitoring apparatus 7100 for monitoring the respiration of a sleeping patient 1000 is illustrated in FIG. 7B. The monitoring apparatus 7100 contains a contactless motion sensor generally directed toward the patient 1000. The motion sensor is configured to generate one or more signals representing bodily movement of the patient 1000, from which may be obtained a signal representing respiratory movement of the patient.

5.8.3 Respiratory Polygraphy

Respiratory polygraphy (RPG) is a term for a simplified form of PSG without the electrical signals (EOG, EEG, EMG), snore, or body position sensors. RPG comprises at least a thoracic movement signal from a respiratory inductance plethysmogram (movement sensor) on a chest band, e.g. the movement sensor 2040, a nasal pressure signal sensed via a nasal cannula, and an oxygen saturation signal from a pulse oximeter, e.g. the pulse oximeter 2055. The three RPG signals, or channels, are received by an RPG headbox, similar to the PSG headbox 2000.

In certain configurations, a nasal pressure signal is a satisfactory proxy for a nasal flow rate signal generated by a flow rate transducer in-line with a sealed nasal mask, in that the nasal pressure signal is comparable in shape to the nasal flow rate signal. The nasal flow rate in turn is equal to the respiratory flow rate if the patient's mouth is kept closed, i.e. in the absence of mouth leaks.

FIG. 7C is a block diagram illustrating a screening/diagnosis/monitoring device 7200 that may be used to implement an RPG headbox in an RPG screening/diagnosis/monitoring system. The screening/diagnosis/monitoring device 7200 receives the three RPG channels mentioned above (a signal indicative of thoracic movement, a signal indicative of nasal flow rate, and a signal indicative of oxygen saturation) at a data input interface 7260. The screening/diagnosis/monitoring device 7200 also contains a processor 7210 configured to carry out encoded instructions. The screening/diagnosis/monitoring device 7200 also contains a non-transitory computer readable memory/storage medium 7230.

Memory 7230 may be the screening/diagnosis/monitoring device 7200's internal memory, such as RAM, flash memory or ROM. In some implementations, memory 7230 may also be a removable or external memory linked to screening/diagnosis/monitoring device 7200, such as an SD card, server, USB flash drive or optical disc, for example. In other implementations, memory 7230 can be a combination of external and internal memory. Memory 7230 includes stored data 7240 and processor control instructions (code) 7250 adapted to configure the processor 7210 to perform certain tasks. Stored data 7240 can include RPG channel data received by data input interface 7260, and other data that is provided as a component part of an application. Processor control instructions 7250 can also be provided as a component part of an application program. The processor 7210 is configured to read the code 7250 from the memory 7230 and execute the encoded instructions. In particular, the code 7250 may contain instructions adapted to configure the processor 7210 to carry out methods of processing the RPG channel data provided by the interface 7260. One such method may be to store the RPG channel data as data 7240 in the memory 7230. Another such method may be to analyse the stored RPG data to extract features. The processor 7210 may store the results of such analysis as data 7240 in the memory 7230.

The screening/diagnosis/monitoring device 7200 may also contain a communication interface 7220. The code 7250 may contain instructions configured to allow the processor 7210 to communicate with an external computing device 7210 (not shown) via the communication interface 7220. The mode of communication may be wired or wireless. In one such implementation, the processor 7210 may transmit the stored RPG channel data from the data 7240 to the remote computing device. In such an implementation, the remote computing device may be configured to analyse the received RPG data to extract features. In another such implementation, the processor 7210 may transmit the analysis results from the data 7240 to the remote computing device.

Alternatively, if the memory 7230 is removable from the screening/diagnosis/monitoring device 7200, the remote computing device may be configured to be connected to the removable memory 7230. In such an implementation, the remote computing device may be configured to analyse the RPG data retrieved from the removable memory 7230 to extract the features.

5.9 PORTABLE OXYGEN CONCENTRATOR (POC)

Portable oxygen concentrators may take advantage of pressure swing adsorption (PSA). Pressure swing adsorption may involve using one or more compressors to increase gas pressure inside a canister that contains particles of a gas separation adsorbent arranged in a "sieve bed". As the pressure increases, certain molecules in the gas may become adsorbed onto the gas separation adsorbent. Removal of a portion of the gas in the canister under the pressurized conditions allows separation of the non-adsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009-0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapor and other trace gases. If a gas mixture such as air, for example, is passed under pressure through a canister containing a gas separation adsorbent bed that attracts nitrogen more strongly than it does oxygen, part or all of the nitrogen will stay in the bed, and the gas coming out of the canister will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched air. By alternating canisters in a two-canister system, one canister can be separating oxygen while the other canister is being purged (resulting in a continuous separation of the oxygen from the nitrogen). In this manner, oxygen enriched air can be accumulated, such as in a storage container or other pressurizable vessel or conduit coupled to the canisters, for a variety of uses including providing supplemental oxygen to patients.

5.10 RESPIRATORY THERAPY MODES

Various respiratory therapy modes may be implemented by the disclosed respiratory therapy system.

5.10.1 CPAP Therapy

In some implementations of respiratory pressure therapy, the central controller 4230 sets the treatment pressure Pt according to the treatment pressure equation as part of the therapy parameter determination algorithm 4329. The pressure treatment equation (1) being $Pt = A\Pi(\Phi,t) + P_0$ where A is the amplitude, $\Pi(\Phi,t)$ is the waveform template value (in the range 0 to 1) at the current value 0 of phase and t of time, and $P_0$ is a base pressure. In one such implementation, the amplitude A is identically zero, so the treatment pressure Pt (which represents a target value to be achieved by the interface pressure Pm at the current instant of time) is identically equal to the base pressure $P_0$ throughout the respiratory cycle. Such implementations are generally grouped under the heading of CPAP therapy. In such implementations, there is no need for the therapy engine module 4320 to determine phase $\Phi$ or the waveform template $\Pi(\Phi)$.

In CPAP therapy, the base pressure $P_0$ may be a constant value that is hard-coded or manually entered to the RPT device 4000. Alternatively, the central controller 4230 may repeatedly compute the base pressure $P_0$ as a function of indices or measures of sleep disordered breathing returned by the respective algorithms in the therapy engine module 4320, such as one or more of flow limitation, apnea, hypopnea, patency, and snore. This alternative is sometimes referred to as APAP therapy.

FIG. 4E is a flow chart illustrating a method 4500 carried out by the central controller 4230 to continuously compute the base pressure $P_0$ as part of an APAP therapy implementation of the therapy parameter determination algorithm 4329, when the pressure support A is identically zero.

The method 4500 starts at step 4520, at which the central controller 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the central controller 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the central controller 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the central controller 4230 increases the base pressure $P_0$ by a predetermined pressure increment $\Delta P$, provided the resulting treatment pressure Pt would not exceed a maximum treatment pressure Pmax. In one implementation, the predetermined pressure increment $\Delta P$ and maximum treatment pressure Pmax are 1 $cmH_2O$ and 25 $cmH_2O$ respectively. In other implementations, the pressure increment $\Delta P$ can be as low as 0.1 $cmH_2O$ and as high as 3 $cmH_2O$, or as low as 0.5 $cmH_2O$ and as high as 2 $cmH_2O$. In other implementations, the maximum treatment pressure Pmax can be as low as 15 $cmH_2O$ and as high as 35 $cmH_2O$, or as low as 20 $cmH_2O$ and as high as 30 $cmH_2O$. The method 4500 then returns to step 4520.

At step 4560, the central controller 4230 decreases the base pressure $P_0$ by a decrement, provided the decreased base pressure $P_0$ would not fall below a minimum treatment pressure Pmin. The method 4500 then returns to step 4520. In one implementation, the decrement is proportional to the value of $P_0$-Pmin, so that the decrease in $P_0$ to the minimum treatment pressure Pmin in the absence of any detected events is exponential. In one implementation, the constant of proportionality is set such that the time constant $\tau$ of the exponential decrease of $P_0$ is 60 minutes, and the minimum treatment pressure Pmin is 4 $cmH_2O$. In other implementations, the time constant $\tau$ could be as low as 1 minute and as high as 300 minutes, or as low as 5 minutes and as high as 180 minutes. In other implementations, the minimum treatment pressure Pmin can be as low as 0 $cmH_2O$ and as high as 8 $cmH_2O$, or as low as 2 $cmH_2O$ and as high as 6 $cmH_2O$. Alternatively, the decrement in $P_0$ could be predetermined, so the decrease in $P_0$ to the minimum treatment pressure Pmin in the absence of any detected events is linear.

5.10.2 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the therapy parameter determination algorithm 4329 oscillates the treatment pressure Pt between two values or levels in synchrony with the spontaneous respiratory effort of the patient 1000. That is, based on the typical waveform templates $\Pi(\Phi,t)$ described above, the therapy parameter determination algorithm 4329 increases the treatment pressure Pt to $P_0+A$ (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few $cmH_2O$) sometimes referred to as the Expiratory Pressure Relief (EPR). Such forms are sometimes referred to as CPAP therapy with EPR, which is generally thought to be more comfortable than straight CPAP therapy. In CPAP therapy with EPR, either or both of the IPAP and the EPAP may be constant values that are hard-coded or manually entered to the RPT device 4000. Alternatively, the therapy parameter determination algorithm 4329 may repeatedly compute the IPAP and/or the EPAP during CPAP with EPR. In this alternative, the therapy parameter determination algorithm 4329 repeatedly computes the EPAP and/or the IPAP as a function of indices or measures of sleep disordered breathing returned by the respective algorithms in the therapy engine module 4320 in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 $cmH_2O$. The predetermined pressure support value is a setting of the RPT device 4000, and may be set for example by hard-coding during configuration of the RPT device 4000 or by manual entry through the input device 4220.

In other forms of pressure support ventilation therapy, broadly known as servo-ventilation, the therapy parameter determination algorithm 4329 takes as input some currently measured or estimated parameter of the respiratory cycle (e.g. the current measure Vent of ventilation) and a target value of that respiratory parameter (e.g. a target value Vtgt of ventilation) and repeatedly adjusts the parameters of equation (1) to bring the current measure of the respiratory parameter towards the target value. In a form of servo-ventilation known as adaptive servo-ventilation (ASV), which has been used to treat CSR, the respiratory parameter is ventilation, and the target ventilation value Vtgt is computed by the target ventilation determination algorithm 4328 from the typical recent ventilation Vtyp, as described above.

In some forms of servo-ventilation, the therapy parameter determination algorithm 4329 applies a control methodology to repeatedly compute the pressure support A so as to bring the current measure of the respiratory parameter towards the target value. One such control methodology is Proportional-Integral (PI) control. In one implementation of PI control, suitable for ASV modes in which a target ventilation Vtgt is set to slightly less than the typical recent ventilation Vtyp, the pressure support A is repeatedly computed as:

$$A = Gf(Vent - Vtgt)dt \qquad (1)$$

where G is the gain of the PI control. Larger values of gain G can result in positive feedback in the therapy engine module 4320. Smaller values of gain G may permit some residual untreated CSR or central sleep apnea. In some implementations, the gain G is fixed at a predetermined value, such as −0.4 cmH$_2$O/(L/min)/sec. Alternatively, the gain G may be varied between therapy sessions, starting small and increasing from session to session until a value that substantially eliminates CSR is reached. Conventional means for retrospectively analysing the parameters of a therapy session to assess the severity of CSR during the therapy session may be employed in such implementations. In yet other implementations, the gain G may vary depending on the difference between the current measure Vent of ventilation and the target ventilation Vtgt.

Other servo-ventilation control methodologies that may be applied by the therapy parameter determination algorithm 4329 include proportional (P), proportional-differential (PD), and proportional-integral-differential (PID).

The value of the pressure support A computed via equation (2) may be clipped to a range defined as [Amin, Amax]. In this implementation, the pressure support A sits by default at the minimum pressure support Amin until the measure of current ventilation Vent falls below the target ventilation Vtgt, at which point A starts increasing, only falling back to Amin when Vent exceeds Vtgt once again.

The pressure support limits Amin and Amax are settings of the RPT device 4000, set for example by hard-coding during configuration of the RPT device 4000 or by manual entry through the input device 4220.

In pressure support ventilation therapy modes, the EPAP is the base pressure P$_0$. As with the base pressure P$_0$ in CPAP therapy, the EPAP may be a constant value that is prescribed or determined during titration. Such a constant EPAP may be set for example by hard-coding during configuration of the RPT device 4000 or by manual entry through the input device 4220. This alternative is sometimes referred to as fixed-EPAP pressure support ventilation therapy. Titration of the EPAP for a given patient may be performed by a clinician during a titration session with the aid of PSG, with the aim of preventing obstructive apneas, thereby maintaining an open airway for the pressure support ventilation therapy, in similar fashion to titration of the base pressure P$_0$ in constant CPAP therapy.

Alternatively, the therapy parameter determination algorithm 4329 may repeatedly compute the base pressure P$_0$ during pressure support ventilation therapy. In such implementations, the therapy parameter determination algorithm 4329 repeatedly computes the EPAP as a function of indices or measures of sleep disordered breathing returned by the respective algorithms in the therapy engine module 4320, such as one or more of flow limitation, apnea, hypopnea, patency, and snore. Because the continuous computation of the EPAP resembles the manual adjustment of the EPAP by a clinician during titration of the EPAP, this process is also sometimes referred to as auto-titration of the EPAP, and the therapy mode is known as auto-titrating EPAP pressure support ventilation therapy, or auto-EPAP pressure support ventilation therapy.

5.10.3 High Flow Therapy

In other forms of respiratory therapy, the pressure of the flow of air is not controlled as it is for respiratory pressure therapy. Rather, the central controller 4230 controls the pressure generator 4140 to deliver a flow of air whose device flow rate Qd is controlled to a treatment or target flow rate Qtgt that is typically positive throughout the patient's breathing cycle. Such forms are generally grouped under the heading of flow therapy. In flow therapy, the treatment flow rate Qtgt may be a constant value that is hard-coded or manually entered to the RPT device 4000. If the treatment flow rate Qtgt is sufficient to exceed the patient's peak inspiratory flow rate, the therapy is generally referred to as high flow therapy (HFT). Alternatively, the treatment flow rate may be a profile Qtgt(t) that varies over the respiratory cycle.

5.11 GLOSSARY

For the purposes of the present technology disclosure, in certain forms of the present technology, one or more of the following definitions may apply. In other forms of the present technology, alternative definitions may apply.

5.11.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.11.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

As used herein, a "composite" is a material made from two or more constituent materials. The constituent materials can have very different physical or chemical properties that, when combined, can produce a material with characteristics different from the individual components. The individual components remain separate and distinct within the finished structure. For example, the composite can be made up of two or more layers, and can be a multi-layered material, with each layer being a constituent material. The adjacent constituent materials can be of different physical or chemical properties, or can be of the same or similar physical or chemical properties. In a further embodiment, the adjacent constituent materials each have a grain direction, the grain direction of the adjacent constituent materials being offset at an angle relative to each other.

Textile: A flexible material formed from a network of fibres, which may be natural, artificial, or a combination thereof. The fibres (e.g. wool, flax, cotton, hemp, and/or artificial fibres) may be spun into a yarn that is woven, knitted, crocheted, knotted, tatted, felted, and/or braided to form the textile. As used herein, the terms "textile" and "fabric" are interchangeable.

5.11.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

Flexural modulus: (also bending modulus) A property computed as the ratio of stress to strain in flexural deformation, or the tendency for a material to resist bending. Flexural modulus is inversely related to deflection—a lower deflection would result in a higher modulus.

Young's modulus: A mechanical property that measures the stiffness of a solid material. It defines the relationship between stress (force per unit area) and strain (proportional deformation) in a material in the linear elasticity regime of a uniaxial deformation; i.e. under tensile (extension) or compressive (compression) stress.

5.11.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

Inhalation Time (Ti): The duration of the inspiratory portion of the respiratory flow rate waveform.

Exhalation Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.11.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP–EPAP). In some contexts, pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

5.11.4 Anatomy 5.11.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.11.4.2 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.11.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.11.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.11.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.11.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.11.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.11.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.12 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means+/−5-10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.13 REFERENCE SIGNS LIST 8000 patient interface
8010 headgear
8020 tensioning structure
8030 air outlet
8040 air inlet
8050 conduit
8060 headgear tubing
8070 inner layer
8080 film
8090 film
8100 seal-forming structure
8110 air flow
8120 seam tape
9000 patient interface
9010 headgear
9020 tensioning structure
9030 outlet
9040 air inlet
9050 fastening portion
9060 headgear tubing
9070 inner surface
9080 vent
9090 seal-forming structure
9100 sealing flanges
9110 plenum chamber
9112 inlet port
9120 first air holding material
9120a outer surface of first air holding material
9125 connection between edges
9130 second air holding material
9130a outer surface of second air holding material
9140 conduit/cavity
9150 first fabric layer
9160 second fabric layer
9170 foam 9180 length direction
9190 first transverse axis
9200 second transverse axis
10000 patient interface
10010 headgear
10030 tensioning structure
10040 retention structure
10050 outlet
10060 fastening portion
10070 inner surface double wall film
11000 patient interface
11010 headgear
11020 tensioning structure
11030 outlet
11040 inlet
11050 first fabric layer
11060 second fabric layer
11050a first fabric layer
11050b first fabric layer
4170 air pressure tubing
11100 seal-forming structure
12000 patient interface
12010 headgear
12020 tensioning structure
12030 orifice
12040 retention structure
12050 first fabric layer
12060 second fabric layer
4170 tubing
12100 seal-forming structure
13000 composite material
13010 first fabric layer
13020 first air holding material
13030 second air holding material
13040 second fabric layer
13050 foam
13060 cavity
13070 first side
13080 second side
13090 third fabric layer
14000 headgear
14010 headgear tubing
14020 kink
14000a headgear
15000 headgear tubing
15020 first side
15030 second side
15040 second fabric layer
15100 first fabric layer
15220 rigidiser
15230 spine
15240 protrusions
15250 collar
16000 headgear tubing
16020 first side
16030 second side
16040 second fabric layer
16100 first fabric layer
16220 rigidiser
16230 spine
16240 protrusions
16250 collar
16260 tab
16270 width of spine
16280 width of rigidiser
17220 rigidiser
17230 spine 17250 collar
17260 tab
18000 headgear tubing
18030 second side
18220 rigidiser
18230 spine
18240 protrusions
18250 collar
18260 tab
19220 rigidiser
19240 protrusions
20000 rigidiser
20240*a* protrusion opposing
20240*b* protrusion alternating
20240*c* protrusion alternating
20230 spine
20230*a* spine
21010 rigidiser
21020 second air holding material
21030 first fabric layer
21040 second fabric layer
21050 foam
21060 foam
23000 plenum chamber
23010 frame
23020 bladder
23030 seal-forming structure
23040 valve socket
23050 elbow ring
23060 ribs

The invention claimed is:

1. A headgear for providing a force to hold a seal-forming structure in a therapeutically effective position on a patient's head, the seal-forming structure constructed and arranged to form a seal with a region of the patient's face surrounding an entrance to the patient's airways for delivery of a flow of air at a therapeutic pressure of at least 6 cmH$_2$O above ambient air pressure throughout the patient's respiratory cycle in use, the headgear comprising:

at least one air inlet;

at least one air outlet configured to be in fluid communication with the seal-forming structure when the headgear is in use;

headgear tubing extending along a length between the at least one air inlet and the at least one air outlet, the headgear tubing being formed from a composite material; and a tensioning structure for providing a force to maintain the seal-forming structure in the as-used position;

wherein the composite material comprises:

a double walled film including a first air-holding material and a second air-holding material defining an inner cavity between the first air-holding material and the second air-holding material, wherein the double walled film includes an outer surface, the outer surface having a first side on the first air-holding material and a second side on the second air-holding material;

wherein the double walled film is impervious to pressurised air;

wherein a first fabric layer is connected to the first side and a second fabric layer is connected to the second side;

wherein a gap is formed in the first air-holding material and a fastening portion bridges the gap to form an air sealing layer;

wherein the headgear tubing has a first transverse axis extending generally transversely of the headgear tubing along the length, and a second transverse axis generally transverse to the first transverse axis; and wherein the headgear tubing is more expandable in a first direction along the first transverse axis than in a second direction along the second transverse axis.

2. The headgear according to claim 1, wherein the composite material has a flexural modulus of less than 15 N/mm$^2$.

3. The headgear according to claim 1, wherein the headgear tubing is made of a material that is stretchable.

4. The headgear according to claim 1, wherein the headgear tubing is more stretchable along at least part of its length than in the second transverse axis.

5. The headgear according to claim 1, wherein the Young's modulus along the length of the tubing is about 15 N/mm$^2$ to about 150 N/mm$^2$.

6. The headgear according to claim 1, wherein the fastening portion is openable to expose the double walled film.

7. The headgear according to claim 6, wherein the fastening portion is in contact with the headgear tubing along the length.

8. The headgear according to claim 6, wherein the fastening portion extends from a first position proximate to the at least one air inlet to a second position proximate to the at least one air outlet.

9. The headgear according to claim 1, wherein the headgear tubing is flat when in a collapsed state.

10. The headgear according to claim 1, wherein the headgear tubing further comprises an air vent near the at least one air outlet of the headgear.

11. The headgear according to claim 1, wherein the headgear tubing when in an inflated state is arranged to conform to a contour of a patient's head.

12. The headgear according to claim 1, wherein the headgear tubing has a flexural modulus of less than 15 N/mm$^2$.

13. The headgear according to claim 1, wherein the second fabric layer is annealed to the first fabric layer.

14. The headgear according to claim 1, wherein the double walled film has a total transmittance of more than 90%.

15. The headgear according to claim 1, wherein the double walled film is selected from thermoplastic polyurethane.

16. The headgear according to claim 1, wherein the first fabric layer is laminated to the first side via thermal bonding or glue bonding.

17. The headgear according to claim 1, wherein the second fabric layer is laminated to the second side via thermal bonding or glue bonding.

18. The headgear according to claim 1, wherein the first fabric layer is a mesh fabric layer, the mesh fabric layer has a knit structure selected from single jersey, rib, interlock, raschel, or jacquard.

19. The headgear according to claim 1, wherein the second fabric layer is selected from microfiber yarns, nylon 6,6, peach-skin finish, elastic knitted fabric, two way stretch, non stretch, circular knit fabric, woven fabric, or warp knit fabric.

20. The headgear according to claim 1, wherein the second fabric layer is surface treated with a hydrophobic coating.

21. The headgear according to claim 1, wherein the composite material further comprises a foam sandwiched between the second fabric layer and the second side of the double walled film.

22. The headgear according to claim 1, wherein the composite material further comprises a foam sandwiched between the first fabric layer and the first side of the double walled film.

23. The headgear according to claim 1, wherein the headgear tubing is formed from at least two composite materials for providing different stiffness and/or flexibility.

24. The headgear according to claim 1, wherein the tensioning structure is positionable to overlie a posterior region of the patient's head.

25. The headgear according to claim 1, wherein the tensioning structure is an elastic material.

26. The headgear according to claim 1, wherein the tensioning structure is formed from the composite material.

27. The headgear according to claim 1, wherein the at least one air inlet is positionable to overlie a cranial region of the patient's head when in use.

*    *    *    *    *